(12) United States Patent
Nakashima et al.

(10) Patent No.: US 9,868,714 B2
(45) Date of Patent: Jan. 16, 2018

(54) PYRONE COMPOUNDS AND HERBICIDES COMPRISING THE SAME

(71) Applicant: SUMITOMO CHEMICAL COMPANY, LIMITED, Tokyo (JP)

(72) Inventors: Yosuke Nakashima, Tokyo (JP); Yoshinobu Jin, Hyogo (JP)

(73) Assignee: SUMITOMO CHEMICAL COMPANY, Tokyo (JP)

( * ) Notice: Subject to any disclaimer, the term of this patent is extended or adjusted under 35 U.S.C. 154(b) by 132 days.

(21) Appl. No.: 14/433,722

(22) PCT Filed: Oct. 7, 2013

(86) PCT No.: PCT/JP2013/077688
§ 371 (c)(1),
(2) Date: Apr. 6, 2015

(87) PCT Pub. No.: WO2014/058037
PCT Pub. Date: Apr. 17, 2014

(65) Prior Publication Data
US 2015/0274691 A1    Oct. 1, 2015

(30) Foreign Application Priority Data
Oct. 9, 2012    (JP) ................ 2012-223872

(51) Int. Cl.
| | |
|---|---|
| *A01N 43/78* | (2006.01) |
| *A01N 43/40* | (2006.01) |
| *C07D 309/38* | (2006.01) |
| *A01N 43/82* | (2006.01) |
| *C07D 407/12* | (2006.01) |
| *C07D 417/12* | (2006.01) |
| *C07D 409/12* | (2006.01) |
| *C07D 405/12* | (2006.01) |
| *A01N 43/16* | (2006.01) |
| *C07D 405/14* | (2006.01) |
| *C07D 309/36* | (2006.01) |
| *A01N 43/54* | (2006.01) |
| *A01N 43/58* | (2006.01) |
| *A01N 43/60* | (2006.01) |

(52) U.S. Cl.
CPC .......... *C07D 309/38* (2013.01); *A01N 43/16* (2013.01); *A01N 43/40* (2013.01); *A01N 43/54* (2013.01); *A01N 43/58* (2013.01); *A01N 43/60* (2013.01); *A01N 43/78* (2013.01); *A01N 43/82* (2013.01); *C07D 309/36* (2013.01); *C07D 405/12* (2013.01); *C07D 405/14* (2013.01); *C07D 407/12* (2013.01); *C07D 409/12* (2013.01); *C07D 417/12* (2013.01)

(58) Field of Classification Search
None
See application file for complete search history.

(56) References Cited

U.S. PATENT DOCUMENTS

| | | | |
|---|---|---|---|
| 5,393,729 A | 2/1995 | Fischer et al. | |
| 5,977,029 A | 11/1999 | Fischer et al. | |
| 5,994,274 A | 11/1999 | Fischer et al. | |
| 6,005,103 A | 12/1999 | Domagala et al. | |
| 6,071,937 A | 6/2000 | Bretschneider et al. | |
| 6,140,358 A | 10/2000 | Lieb et al. | |
| 6,316,486 B1 | 11/2001 | Lieb et al. | |
| 6,441,030 B1 | 8/2002 | Lieb et al. | |
| 2004/0097558 A1 | 5/2004 | Fischer et al. | |

FOREIGN PATENT DOCUMENTS

| | | |
|---|---|---|
| CN | 1085554 | 4/1994 |
| CN | 1206413 | 1/1999 |
| CN | 1484643 | 3/2004 |

(Continued)

OTHER PUBLICATIONS

International Search Report dated Nov. 21, 2013 in International Application No. PCT/JP2013/077688.
Patent Cooperation Treaty (PCT) International Preliminary Report on Patentability dated Apr. 24, 2015 in International Application No. PCT/JP2013/077688.

(Continued)

*Primary Examiner* — Mina Haghighatian
*Assistant Examiner* — Erin Hirt
(74) *Attorney, Agent, or Firm* — Wenderoth, Lind & Ponack, L.L.P.

(57) ABSTRACT

The present invention provides a compound having an excellent efficacy for controlling weeds. A pyrone compound of formula (I):

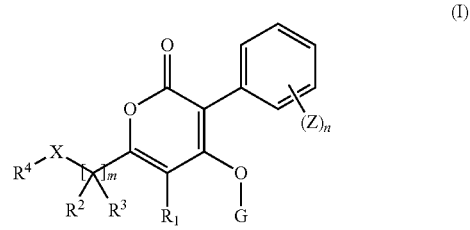

wherein m is 1, 2 or 3; n is an integer of any one of 1 to 5; X represents O, S, S(O) or S(O)$_2$; R$^1$ represents a hydrogen atom or a methyl group; R$^2$ and R$^3$ represents a hydrogen atom, an C$_{1-6}$ alkyl group and the like; R$^4$ represents an C$_{6-10}$ aryl group or a five- to six-membered heteroaryl group; G represents a hydrogen atom and the like; Z represents a halogen atom, a cyano group, a nitro group, a phenyl group, an C$_{1-6}$ alkyl group and the like;
is useful as an active ingredient for herbicides.

6 Claims, No Drawings

(56) References Cited

FOREIGN PATENT DOCUMENTS

| EA | 200900781 | 12/2009 |
|---|---|---|
| JP | 6-220036 | 8/1994 |
| JP | 11-505220 | 5/1999 |
| JP | 11-510481 | 9/1999 |
| JP | 2000-500767 | 1/2000 |
| JP | 2000-507564 | 6/2000 |
| JP | 2002-527429 | 8/2002 |
| SU | 680615 | 8/1979 |
| WO | 89/10922 | 11/1989 |
| WO | 2008/071405 | 6/2008 |
| WO | 2012/165648 | 12/2012 |

OTHER PUBLICATIONS

First Examination Report dated Jan. 11, 2017, in corresponding Australian Patent Application No. 2013330813.
Second Official Action dated Jan. 17, 2017, in corresponding Chinese Patent Application No. 201380064042.5 (with English translation).
Official Action with search report dated Mar. 28, 2016 in Chinese application No. 201380064042.5 (with English translation).
Official Action dated Jun. 29, 2016 in corresponding Chilean patent application No. 2015-00884 (with English translation).
Office Action dated Feb. 13, 2017 in corresponding Chilean Application No. 2015-00884, with English translation.
Office Action dated Aug. 24, 2017 in Russian Application No. 2015117430, with English Translation.

PYRONE COMPOUNDS AND HERBICIDES COMPRISING THE SAME

This application claims priority to and the benefit of Japanese Patent Application No. 2012-223872 filed Oct. 9, 2012, the entire contents of which are incorporated herein by reference.

TECHNICAL FIELD

The present invention relates to pyrone compounds and herbicides comprising the same.

BACKGROUND ART

Heretofore, some compounds that are useful as active ingredients in herbicides for controlling weeds have been developed and some compounds having an efficacy for controlling weeds have been found.

Some pyrone compounds having herbicidal activity have been known (see Patent Documents 1 to 8).

CITATION LIST

Patent Document

Patent Document 1: JP 06-220036 A
Patent Document 2: JP 11-505220 A
Patent Document 3: JP 11-510481 A
Patent Document 4: U.S. Pat. No. 5,977,029
Patent Document 5: U.S. Pat. No. 6,005,103
Patent Document 6: JP 2000-507564
Patent Document 7: JP 2000-500767
Patent Document 8: JP 2002-527429

SUMMARY OF THE INVENTION

An object of the present invention is to provide a compound having an excellent efficacy for controlling weeds.

The present inventors have intensively studied to find that compounds having an excellent efficacy for controlling weeds and as a result, found that a pyrone compound of the following formula (I) has an excellent efficacy for controlling weeds, which thus have completed the present invention.

Specifically, the present invention includes the following [1] to [7].

[1] A pyrone compound of formula (I):

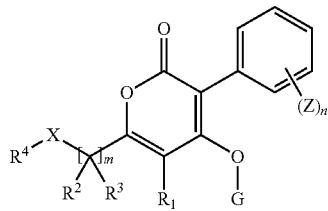

wherein
m is 1, 2 or 3;
n is an integer of any one of 1 to 5;
X represents O, S, S(O) or S(O)$_2$;
$R^1$ represents a hydrogen atom or a methyl group;
$R^2$ and $R^3$ represent independently of each other a hydrogen atom, a halogen atom, an $C_{1-6}$ alkyl group, a $C_{1-6}$ haloalkyl group, a $C_{3-8}$ cycloalkyl group or a $C_{3-8}$ halocycloalkyl group, alternatively $R^2$ and $R^3$ connect each other to represent an $C_{2-5}$ alkylene chain, or $R^2$ and $R^3$ combine each other to represent an $C_{1-3}$ alkylidene group optionally having one or more halogen atoms (with the proviso that when m is 2 or 3, two or three $R^2$ may be same or different to each other and two or three $R^3$ may be same or different to each other);
$R^4$ represents an $C_{6-10}$ aryl group or a five- to six-membered heteroaryl group (with the proviso that the $C_{6-10}$ aryl group and the five- or six-membered heteroaryl group may have optionally one or more substituents selected from the group consisting of a halogen atom, a cyano group, a nitro group, an amino group, an ($C_{1-6}$ alkyl)amino group, an ($C_{1-6}$ alkyl)($C_{1-6}$ alkyl)amino group, a pentafluorothio group, an $C_{1-6}$ alkyl group, an $C_{2-6}$ alkenyl group, an $C_{2-6}$ alkynyl group, an $C_{1-6}$ alkoxy group, an $C_{1-6}$ alkylthio group, an $C_{3-6}$ alkenyloxy group, an $C_{3-6}$ alkynyloxy group, an $C_{6-10}$ aryl group, an $C_{6-10}$ aryloxy group, an $C_{1-6}$ alkylsulfinyl group, an $C_{1-6}$ alkylsulfonyl group, a hydroxyl group, an ($C_{1-6}$ alkyl)carbonyl group, a hydroxycarbonyl group, a ($C_{1-6}$ alkoxy)carbonyl group and an ($C_{6-10}$ aryl)$C_{1-6}$ alkoxy group, and when two or more substituents exist, the substituents may be same or different to each other; and the $C_{1-6}$ alkyl group, the $C_{2-6}$ alkenyl group, the $C_{2-6}$ alkynyl group, the $C_{1-6}$ alkoxy group, the $C_{1-6}$ alkylthio group, the $C_{3-6}$ alkenyloxy group, the $C_{3-6}$ alkynyloxy group, the $C_{6-10}$ aryl group, the $C_{6-10}$ aryloxy group, the $C_{1-6}$ alkylsulfinyl group, the $C_{1-6}$ alkylsulfonyl group, the ($C_{1-6}$ alkyl)carbonyl group, the ($C_{1-6}$ alkoxy)carbonyl group and the ($C_{6-10}$ aryl)$C_{1-6}$ alkoxy group may each have one or more halogen atoms or $C_{1-3}$ haloalkyl groups, and when two or more halogen atoms or $C_{1-3}$ haloalkyl groups exist, the halogen atoms or the $C_{1-3}$ haloalkyl groups may be same or different to each other respectively);
G represents a hydrogen atom or a group of any one of the following formulae:

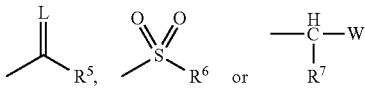

{wherein
L represents an oxygen atom or a sulfur atom;
$R^5$ represents an $C_{1-6}$ alkyl group, a $C_{3-8}$ cycloalkyl group, an $C_{2-6}$ alkenyl group, an $C_{2-6}$ alkynyl group, an $C_{6-10}$ aryl group, an ($C_{6-10}$ aryl)$C_{1-6}$ alkyl group, an $C_{1-6}$ alkoxy group, a $C_{3-8}$ cycloalkoxy group, an $C_{3-6}$ alkenyloxy group, an $C_{3-6}$ alkynyloxy group, an $C_{6-10}$ aryloxy group, an ($C_{6-10}$ aryl) $C_{1-6}$ alkoxy group, an ($C_{1-6}$ alkyl)($C_{1-6}$ alkyl)amino group, an ($C_{3-6}$ alkenyl)($C_{3-6}$ alkenyl)amino group, an ($C_{1-6}$ alkyl) ($C_{6-10}$ aryl)amino group or a five- to six-membered heteroaryl group (with the proviso that these groups may each have one or more halogen atoms, and when two or more halogen atoms exist, the halogen atoms may be same or different to each other; and the $C_{3-8}$ cycloalkyl group, the $C_{6-10}$ aryl group, an aryl moiety of the ($C_{6-10}$ aryl)$C_{1-6}$ alkyl group, the $C_{3-8}$ cycloalkoxy group, the $C_{6-10}$ aryloxy group, an aryl moiety of the ($C_{6-10}$ aryl)$C_{1-6}$ alkoxy group, an aryl moiety of the ($C_{1-6}$ alkyl) ($C_{6-10}$ aryl)amino group and a five- to six-membered heteroaryl group may each have one or more $C_{1-6}$ alkyl groups, and when two or more $C_{1-6}$ alkyl groups exist, the alkyl groups may be same or different to each other);
$R^6$ represents an $C_{1-6}$ alkyl group, an $C_{6-10}$ aryl group or an ($C_{1-6}$ alkyl)($C_{1-6}$ alkyl)amino group (with the proviso that these groups may each have one or more halogen atoms and when two or more halogen atoms exist, the halogen atoms may be same or different to each other; and the $C_{6-10}$ aryl group may have optionally one or more $C_{1-6}$ alkyl groups and when two or more $C_{1-6}$ alkyl groups exist, the alkyl groups may be same or different to each other);

$R^7$ represents a hydrogen atom or an $C_{1-6}$ alkyl group;

W represents an $C_{1-6}$ alkoxy group, an $C_{1-6}$ alkylthio group, an $C_{1-6}$ alkylsulfinyl group or an $C_{1-6}$ alkylsulfonyl group (with the proviso that these groups may each have one or more halogen atoms and when two or more halogen atoms exist, the halogen atoms may be same or different to each other));

Z represents a halogen atom, a cyano group, a nitro group, an $C_{1-6}$ alkyl group, an $C_{2-6}$ alkenyl group, an $C_{2-6}$ alkynyl group, an $C_{1-6}$ alkoxy group, an ($C_{1-6}$ alkyl)carbonyl group, an $C_{1-6}$ alkylthio group, an $C_{6-10}$ aryloxy group, a five- or six-membered heteroaryloxy group, a $C_{3-8}$ cycloalkyl group, an $C_{6-10}$ aryl group or a five- to six-membered heteroaryl group (with the proviso that the $C_{1-6}$ alkyl group, the $C_{2-6}$ alkenyl group, the $C_{2-6}$ alkynyl group, the $C_{1-6}$ alkoxy group, the ($C_{1-6}$ alkyl)carbonyl group and the $C_{1-6}$ alkylthio group may each have one or more halogen atoms, and when two or more halogen atoms exist, the halogen atoms may be same or different to each other; and the $C_{6-10}$ aryl group, the five- to six-membered heteroaryl group, the $C_{6-10}$ aryloxy group and the five- to six-membered heteroaryloxy group may each have one or more substituents selected from the group consisting of a halogen atom, an $C_{1-6}$ alkyl group and a $C_{1-6}$ haloalkyl group, and when two or more substituents exist, the substituents may be same or different to each other; and the $C_{3-8}$ cycloalkyl group may have optionally one or more substituents selected from the group consisting of a halogen atom and an $C_{1-6}$ alkyl group, and when two or more substituents exist, the substituents may be same or different to each other; when n is an integer of 2 or more, Z may be same or different to each other).

[2] The pyrone compound of [1] wherein
m is 2 or 3;
n is an integer of any one of 1 to 3;
$R^1$ represents a hydrogen atom or a methyl group;
$R^2$ and $R^3$ represent independently of each other a hydrogen atom or an $C_{1-3}$ alkyl group, alternatively $R^2$ and $R^3$ connect each other to represent an $C_{2-5}$ alkylene chain (with the proviso that when m is 2 or 3, two or three $R^2$ may be same or different to each other and two or three $R^3$ may be same or different to each other);

$R^4$ represents a phenyl group, a 2-pyridyl group, a 3-pyridyl group, a 4-pyridyl group, a 2-pyrimidinyl group, a 2-pyrazinyl group, a 3-pyridazinyl group, a 3-furyl group, a 2-thienyl group or a 2-thiazolyl group (with the proviso that the phenyl group, the 2-pyridyl group, the 3-pyridyl group, the 4-pyridyl group, the 2-pyrimidinyl group, the 2-pyrazinyl group, the 3-pyridazinyl group, the 3-furyl group, the 2-thienyl group and the 2-thiazolyl group may each have one or more substituents selected from the group consisting of a halogen atom, an $C_{1-3}$ alkyl group, a hydroxyl group, a ($C_{1-3}$ alkyl)carbonyl group, a ($C_{1-3}$ alkoxy)carbonyl group, an $C_{1-3}$ alkoxy group, a $C_{1-3}$ haloalkyl group, an $C_{1-3}$ alkylthio group, a $C_{1-3}$ haloalkylthio group, a cyano group, a nitro group, an amino group, a pentafluorothio group and a $C_{1-3}$ haloalkoxy group, and when two or more substituents exist, the substituents may be same or different to each other; and when two or more substituents exist, the substituents may be same or different respectively);

G represents a hydrogen atom or a group of any one of the following formulae:

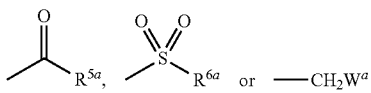

{wherein
$R^{5a}$ represents an $C_{1-6}$ alkyl group, an $C_{6-10}$ aryl group, an $C_{1-6}$ alkoxy group, an $C_{3-6}$ alkenyloxy group, an $C_{3-6}$ alkynyloxy group or an $C_{6-10}$ aryloxy group;
$R^{6a}$ represents an $C_{1-6}$ alkyl group; and
$W^a$ represents an $C_{1-3}$ alkoxy group};

Z represents a halogen atom, an $C_{1-3}$ alkyl group, an $C_{2-6}$ alkenyl group, an $C_{2-6}$ alkynyl group, an $C_{1-3}$ alkoxy group, a $C_{3-8}$ cycloalkyl group, a nitro group, a phenyl group or a five- to six-membered heteroaryloxy group (with the proviso that the $C_{1-3}$ alkyl group, the $C_{2-6}$ alkenyl group, the $C_{2-6}$ alkynyl group and the $C_{1-3}$ alkoxy group may have optionally one or more halogen atoms, and when two or more halogen atoms exist, the halogen atoms may be same or different to each other; and the phenyl group and the five- to six-membered heteroaryloxy group may have optionally one or more substituents selected from the group consisting of a halogen atom, an $C_{1-6}$ alkyl group and a $C_{1-6}$ haloalkyl group, and when two or more substituents exist, the substituents may be same or different to each other).

[3] The pyrone compound of [2] wherein
m is 2;
$R^1$ represents a hydrogen atom or a methyl group;
$R^2$ and $R^3$ represents independently of each other a hydrogen atom, a methyl group or an ethyl group, alternatively $R^2$ and $R^3$ connect each other to represent an ethylene chain (with the proviso that two $R^2$ may be same or different to each other and two $R^3$ may be same or different to each other);

$R^4$ represents a phenyl group, a 2-pyridyl group, a 3-furyl group, a 2-thienyl group, a 2-thiazolyl group or a 2-(1,3,4-triazolyl) group (with the proviso that the phenyl group, the 2-pyridyl group, the 3-furyl group, the 2-thienyl group, the 2-thiazolyl group and the 2-(1,3,4-triazolyl) group have each one or more substituents selected from the group consisting of a chlorine atom, a bromine atom, an iodine atom, a fluorine atom, a methyl group, an ethyl group, an isopropyl group, a tert-butyl group, a methoxy group, a nitro group, an amino group, a cyano group, a hydroxyl group, an acetyl group, a methoxycarbonyl group, a pentafluorothio group, a pentafluoroethyl group, a difluoroethyl group, a heptafluoroisopropyl group, a trifluoromethylthio group, a trifluoromethoxy group and a trifluoromethyl group);

G represents a hydrogen atom, an acetyl group, a propionyl group, a butylcarbonyl group, a benzoyl group, a methylsulfonyl group, a methoxycarbonyl group, an ethoxycarbonyl group, an allyloxycarbonyl group, a phenoxycarbonyl group, a methoxymethyl group or an ethoxymethyl group;

Z represents a methyl group, an ethyl group, a phenyl group, a vinyl group, a cyclopropyl group, a nitro group, a fluorine atom, a chlorine atom, a bromine atom, a methoxy group, a trifluoromethyl group, a 5-trifluoromethyl-2-chloropyridyloxy group or an ethynyl group.

[4] The pyrone compound of any one of [1] to [3] wherein G represents a hydrogen atom.

[5] A herbicide comprising a pyrone compound of any one of [1] to [4] as an active ingredient and an inert carrier.

[6] A method for controlling weeds which comprises applying an effective amount of the pyrone compound of any one of [1] to [4] to weeds or soil where weeds grow.

[7] Use of the pyrone compound of any one of [1] to [4] for controlling weeds.

The compound of the present invention shows an efficacy for controlling weeds and is therefore useful as an active ingredient for herbicides.

DESCRIPTION OF EMBODIMENTS

The compound of the present invention (hereinafter, sometimes referred to as "the present compound") is a pyrone compound of a formula (1):

A pyrone compound of formula (1):

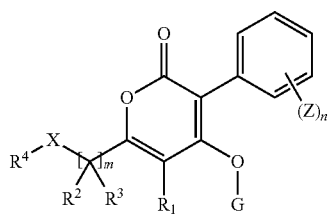

(I)

wherein
m is 1, 2 or 3;
n is an integer of any one of 1 to 5;
X represents O, S, S(O) or S(O)$_2$;
$R^1$ represents a hydrogen atom or a methyl group;
$R^2$ and $R^3$ represent independently of each other a hydrogen atom, a halogen atom, an $C_{1-6}$ alkyl group, a $C_{1-6}$ haloalkyl group, a $C_{3-8}$ cycloalkyl group or a $C_{3-8}$ halocycloalkyl group, alternatively $R^2$ and $R^3$ connect each other to represent an $C_{2-5}$ alkylene chain, or $R^2$ and $R^3$ combine each other to represent an $C_{1-3}$ alkylidene group optionally having one or more halogen atoms (with the proviso that when m is 2 or 3, two or three $R^2$ may be same or different to each other and two or three $R^3$ may be same or different to each other);
$R^4$ represents an $C_{6-10}$ aryl group or a five- to six-membered heteroaryl group (with the proviso that the $C_{6-10}$ aryl group and the five- or six-membered heteroaryl group may have optionally one or more substituents selected from the group consisting of a halogen atom, a cyano group, a nitro group, an amino group, an ($C_{1-6}$ alkyl)amino group, an ($C_{1-6}$ alkyl)($C_{1-6}$ alkyl)amino group, a pentafluorothio group, an $C_{1-6}$ alkyl group, an $C_{2-6}$ alkenyl group, an $C_{2-6}$ alkynyl group, an $C_{1-6}$ alkoxy group, an $C_{1-6}$ alkylthio group, an $C_{3-6}$ alkenyloxy group, an $C_{3-6}$ alkynyloxy group, an $C_{6-10}$ aryl group, an $C_{6-10}$ aryloxy group, an $C_{1-6}$ alkylsulfinyl group, an $C_{1-6}$ alkylsulfonyl group, a hydroxyl group, an ($C_{1-6}$ alkyl)carbonyl group, a hydroxycarbonyl group, a ($C_{1-6}$ alkoxy)carbonyl group and an ($C_{6-10}$ aryl)$C_{1-6}$ alkoxy group, and when two or more substituents exist, the substituents may be same or different to each other; and the $C_{1-6}$ alkyl group, the $C_{2-6}$ alkenyl group, the $C_{2-6}$ alkynyl group, the $C_{1-6}$ alkoxy group, the $C_{1-6}$ alkylthio group, the $C_{3-6}$ alkenyloxy group, the $C_{3-6}$ alkynyloxy group, the $C_{6-10}$ aryl group, the $C_{6-10}$ aryloxy group, the $C_{1-6}$ alkylsulfinyl group, the $C_{1-6}$ alkylsulfonyl group, the ($C_{1-6}$ alkyl)carbonyl group, the ($C_{1-6}$ alkoxy)carbonyl group and the ($C_{6-10}$ aryl) $C_{1-6}$ alkoxy group may each have one or more halogen atoms or $C_{1-3}$ haloalkyl groups, and when two or more halogen atoms or $C_{1-3}$ haloalkyl groups exist, the halogen atoms or the $C_{1-3}$ haloalkyl groups may be same or different to each other respectively);

G represents a hydrogen atom or a group of any one of the following formulae:

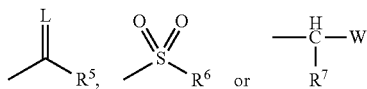

{wherein
L represents an oxygen atom or a sulfur atom;
$R^5$ represents an $C_{1-6}$ alkyl group, a $C_{3-8}$ cycloalkyl group, an $C_{2-6}$ alkenyl group, an $C_{2-6}$ alkynyl group, an $C_{6-10}$ aryl group, an ($C_{6-10}$ aryl)$C_{1-6}$ alkyl group, an $C_{1-6}$ alkoxy group, a $C_{3-8}$ cycloalkoxy group, an $C_{3-6}$ alkenyloxy group, an $C_{3-6}$ alkynyloxy group, an $C_{6-10}$ aryloxy group, an ($C_{6-10}$ aryl) $C_{1-6}$ alkoxy group, an ($C_{1-6}$ alkyl) ($C_{1-6}$ alkyl)amino group, an ($C_{3-6}$ alkenyl) ($C_{3-6}$ alkenyl)amino group, an ($C_{1-6}$ alkyl) ($C_{6-10}$ aryl)amino group or a five- to six-membered heteroaryl group (with the proviso that these groups may each have one or more halogen atoms, and when two or more halogen atoms exist, the halogen atoms may be same or different to each other; and the $C_{3-8}$ cycloalkyl group, the $C_{6-10}$ aryl group, an aryl moiety of the ($C_{6-10}$ aryl)$C_{1-6}$ alkyl group, the $C_{3-8}$ cycloalkoxy group, the $C_{6-10}$ aryloxy group, an aryl moiety of the ($C_{6-10}$ aryl)$C_{1-6}$ alkoxy group, an aryl moiety of the ($C_{1-6}$ alkyl)($C_{6-10}$ aryl)amino group and a five- to six-membered heteroaryl group may each have one or more $C_{1-6}$ alkyl groups, and when two or more $C_{1-6}$ alkyl groups exist, the alkyl groups may be same or different to each other);
$R^6$ represents an $C_{1-6}$ alkyl group, an $C_{6-10}$ aryl group or an ($C_{1-6}$ alkyl)($C_{1-6}$ alkyl)amino group (with the proviso that these groups may each have one or more halogen atoms and when two or more halogen atoms exist, the halogen atoms may be same or different to each other; and the $C_{6-10}$ aryl group may have optionally one or more $C_{1-6}$ alkyl groups and when two or more $C_{1-6}$ alkyl groups exist, the alkyl groups may be same or different to each other);
$R^7$ represents a hydrogen atom or an $C_{1-6}$ alkyl group;
W represents an $C_{1-6}$ alkoxy group, an $C_{1-6}$ alkylthio group, an $C_{1-6}$ alkylsulfinyl group or an $C_{1-6}$ alkylsulfonyl group (with the proviso that these groups may each have one or more halogen atoms and when two or more halogen atoms exist, the halogen atoms may be same or different to each other)};
Z represents a halogen atom, a cyano group, a nitro group, an $C_{1-6}$ alkyl group, an $C_{2-6}$ alkenyl group, an $C_{2-6}$ alkynyl group, an $C_{1-6}$ alkoxy group, an ($C_{1-6}$ alkyl)carbonyl group, an $C_{1-6}$ alkylthio group, an $C_{6-10}$ aryloxy group, a five- or six-membered heteroaryloxy group, a $C_{3-8}$ cycloalkyl group, an $C_{6-10}$ aryl group or a five- to six-membered heteroaryl group (with the proviso that the $C_{1-6}$ alkyl group, the $C_{2-6}$ alkenyl group, the $C_{2-6}$ alkynyl group, the $C_{1-6}$ alkoxy group, the ($C_{1-6}$ alkyl)carbonyl group and the $C_{1-6}$ alkylthio group may each have one or more halogen atoms, and when two or more halogen atoms exist, the halogen atoms may be same or different to each other; and the $C_{6-10}$ aryl group, the five- to six-membered heteroaryl group, the $C_{6-10}$ aryloxy group and the five- to six-membered heteroaryloxy group may each have one or more substituents selected from the group consisting of a halogen atom, an $C_{1-6}$ alkyl group and a $C_{1-6}$ haloalkyl group, and when two or more substituents exist, the substituents may be same or different to each other; and the $C_{3-8}$ cycloalkyl group may have optionally one or more substituents selected from the group consisting of a halogen atom and an $C_{1-6}$ alkyl group, and when two or more substituents exist, the substituents may be same or different to each other; when n is an integer of 2 or more, Z may be same or different to each other).

Hereinafter, the present invention is explained in detail.
The substituent of the present invention is explained.

The "$C_{1-6}$ alkyl group" to be used herein means an alkyl group having one to six carbon atoms, and includes, for example, a methyl group, an ethyl group, a normalpropyl group, an isopropyl group, a normalbutyl group, an isobutyl group, a sec-butyl group, a tert-butyl group, a normalpentyl group, a sec-pentyl group, an isopentyl group, a neopentyl group, a normalhexyl group and an isohexyl group.

The "$C_{1-6}$ haloalkyl group" to be used herein means an $C_{1-6}$ alkyl group substituted with one or more halogen atoms such as a fluorine atom, a chlorine atom, a bromine atom and an iodine atom, and includes, for example, a trifluoromethyl group, a chloromethyl group, a 2,2,2-trichloroethyl group, a 2,2,2-trifluoroethyl group and a 2,2,2-trifluoro-1,1-dichloroethyl group.

The "$C_{3-8}$ cycloalkyl group" to be used herein means a cycloalkyl group having three to eight carbon atoms and includes, for example, a cyclopropyl group, a cyclopentyl group and a cyclohexyl group.

The "$C_{3-8}$ halocycloalkyl group" to be used herein means a $C_{3-8}$ cycloalkyl group substituted with one or more halogen atoms such as a fluorine atom, a chlorine atom, a bromine atom and an iodine atom and includes, for example, a 2-chlorocyclopropyl group and a 4,4-difluorocyclohexyl group.

The "$C_{2-5}$ alkylene chain" to be used herein means an alkylene chain having two to five carbon atoms and includes, for example, an ethylene chain, a propylene chain (i.e., a trimethylene chain), a butylene chain (i.e., a tetramethylene chain) and a pentylene chain (i.e., a pentamethylene chain).

When $R^2$ and $R^3$ connect each other to represent a $C_{2-5}$ alkylene chain, $R^2$ and $R^3$ combine together with the carbon to which $R^2$ and $R^3$ are attached to form a $C_{2-6}$ cycloalkyl group. For example, when $R^2$ and $R^3$ connect each other to represent an ethylene chain, $R^2$ and $R^3$ combine together with the carbon to which $R^2$ and $R^3$ are attached to form a $C_3$ cycloalkyl group, i.e., a cyclopropyl group.

The "$C_{1-3}$ alkylidene chain" to be used herein means an alkylidene chain having one to three carbon atoms and includes, for example, a methylidene group, an ethylidene group and an isopropylidene group.

The "halogen atom" to be used herein includes, for example, a fluorine atom, a chlorine atom, a bromine atom and an iodine atom.

The "$C_{2-6}$ alkenyl group" to be used herein means an alkenyl group having two to six carbon atoms and includes, for example, a vinyl group, an allyl group, a 1-buten-3-yl group and a 3-buten-1-yl group.

The "$C_{2-6}$ alkynyl group" to be used herein means an alkynyl group having two to six carbon atoms and includes, for example, an ethynyl group, a propargyl group and a 2-butynyl group.

The "$C_{1-6}$ alkoxy group" to be used herein means an alkoxy group having one to six carbon atoms and includes, for example, a methoxy group, an ethoxy group, a normalpropyloxy group, an isopropyloxy group, a normalbutoxy group, an isobutoxy group, a sec-butoxy group, a tert-butoxy group, a normalpentyloxy group, a sec-pentyloxy group, an isopentyloxy group, a neopentyloxy group, a normalhexyloxy group and an isohexyloxy group.

The "$C_{1-6}$ alkylthio group" to be used herein means an alkylthio group having one to six carbon atoms and includes, for example, a methylthio group, an ethylthio group and an isopropylthio group.

The "$C_{3-6}$ alkenyloxy group" to be used herein means an alkenyloxy group having three to six carbon atoms and includes, for example, an allyloxy group and a 2-butenyloxy group.

The "$C_{3-6}$ alkynyloxy group" to be used herein means an alkynyloxy group having three to six carbon atoms and includes, for example, a propargyloxy group and a 2-butynyloxy group.

The "($C_{6-10}$ aryl)$C_{1-6}$ alkoxy group" to be used herein means an alkoxy group having one to six carbon atoms substituted with an $C_{6-10}$ aryl group and includes, for example, a benzyloxy group and a phenethyloxy.

The "($C_{6-10}$ aryl)$C_{1-6}$ alkyl group" to be used herein means an $C_{1-6}$ alkyl group substituted with an $C_{6-10}$ aryl group and includes, for example, a benzyl group and a phenethyl group.

The "$C_{3-8}$ cycloalkoxy group" to be used herein means a cycloalkoxy group having three to eight carbon atoms and includes, for example, a cyclopropyloxy group, a cyclopentyloxy group and a cyclohexyloxy group.

The "($C_{1-6}$ alkyl)($C_{1-6}$ alkyl)amino group" to be used herein means an amino group substituted with two $C_{1-6}$ alkyl groups that may be same or different to each other and includes, for example, a dimethylamino group, a diethylamino group and an ethylmethylamino group.

The "($C_{3-6}$ alkenyl)($C_{3-6}$ alkenyl)amino group" to be used herein means an amino group substituted with two $C_{3-6}$ alkenyl groups that may be same or different to each other and includes, for example, a diallylamino group and a di(3-butenyl)amino group.

The "($C_{1-6}$ alkyl)($C_{6-10}$ aryl)amino group" to be used herein means an amino group substituted with an $C_{1-6}$ alkyl group and a $C_{6-10}$ aryl group and includes for example, a methylphenylamino group and an ethylphenylamino group.

The "$C_{1-6}$ alkylsulfinyl group" to be used herein means an alkylsulfinyl group having one to six carbon atoms and includes, for example, a methylsulfinyl group, an ethylsulfinyl group and an isopropylsulfinyl group.

The "$C_{1-6}$ alkylsulfonyl group" to be used herein means an alkylsulfonyl group having one to six carbon atoms and includes, for example, a methylsulfonyl group, an ethylsulfonyl group and an isopropylsulfonyl group.

The "$C_{6-10}$ aryl group" to be used herein means an aryl group having six to ten carbon atoms and includes, for example, a phenyl group and a naphthyl group.

The "five- to six-membered heteroaryl group" to be used herein means an aromatic five- or six-membered heterocyclic group having 1 to 3 heteroatoms selected from a nitrogen atom, an oxygen atom or a sulfur atom and includes, for example, a 2-pyridyl group, a 4-pyridyl group, a 3-furyl group, a pyrimidinyl group, a 3-thienyl group and a 1-pyrazolyl group.

The "$C_{6-10}$ aryloxy group" to be used herein means an aryloxy group having six to ten carbon atoms and includes, for example, a phenoxy group and a naphthyloxy group.

The "five- to six-membered heteroaryloxy group" to be used herein means an aromatic five- or six-membered heterocyclyloxy group having one to three heteroatoms selected from a nitrogen atom, an oxygen atom or a sulfur atom and includes, for example, a 2-pyridyloxy group and a 3-pyridyloxy group.

The "($C_{1-6}$ alkoxy)carbonyl group" to be used herein means a carbonyl group substituted with an $C_{1-6}$ alkoxy group and includes, for example, a methoxycarbonyl group and an ethoxycarbonyl group.

The "($C_{1-6}$ alkyl)amino group" to be used herein means an amino group substituted with an $C_{1-6}$ alkyl group and includes, for example, a monomethylamino group and a monoethylamino group.

The "($C_{1-6}$ alkyl)carbonyl group" to be used herein means a carbonyl group substituted with an $C_{1-6}$ alkyl group and includes, for example, a methylcarbonyl group, an ethylcarbonyl group and an isopropylcarbonyl group.

The "$C_{1-3}$ alkyl group" to be used herein means an alkyl group having one to three carbon atoms and includes, for example, a methyl group, an ethyl group, a normalpropyl group and an isopropyl group.

The "$C_{1-3}$ alkoxy group" to be used herein means an alkoxy group having one to three carbon atoms and includes, for example, a methoxy group, an ethoxy group, a normalpropyloxy group and an isopropyloxy group.

The "$C_{1-3}$ haloalkyl group" to be used herein means a $C_{1-3}$ alkyl group substituted with one or more halogen atoms selected from a fluorine atom, a chlorine atom, a bromine atom or an iodine atom and includes, for example, a trifluoromethyl group, a chloromethyl group, a 2,2,2-trichloroethyl group, a 2,2,2-trifluoroethyl group and a 2,2,2-trifluoro-1,1-dichloroethyl group.

The "$C_{1-3}$ haloalkoxy group" to be used herein means a $C_{1-3}$ alkoxy group substituted with one or more halogen atoms selected from a fluorine atom, a chlorine atom, a bromine atom or an iodine atom and includes, for example, a trifluoromethoxy group, a 2,2,2-trichloroethoxy group, a 3,3-difluoropropyloxy group and a 2,2,2-trifluoroethoxy group.

The "$C_{1-3}$ haloalkylthio group" to be used herein means a $C_{1-3}$ alkylthio group substituted with one or more halogen atoms selected from a fluorine atom, a chlorine atom, a bromine atom or an iodine atom and includes, for example, a trifluoromethylthio group, a chloromethylthio group, a 2,2,2-trichloroethylthio group, a 2,2,2-trifluoroethylthio group and a 2,2,2-trifluoro-1,1-dichloroethylthio group.

For the present compound, the pyrone compounds of the formula (I) and (II) may form agronomically acceptable salts with inorganic bases or organic bases and the present invention may encompass the salt forms of the pyrone compound. The salt includes for example, salts that are formed by mixing the compound with inorganic bases (for example, hydroxides, carbonates, hydrogen carbonates, acetates or hydrides of alkali metals (for example, lithium, sodium and potassium)), hydroxides or hydrides of alkaline-earth metals (for example, magnesium, calcium and barium) and ammonia), organic bases (for example, dimethylamine, triethylamine, piperazine, pyrrolidine, piperidine, 2-phenylethylamine, benzylamine, ethanolamine, diethanolamine, pyridine and collidine) or metal alkoxides (for example, sodium methoxide, potassium tert-butoxide and magnesium methoxide).

When the present compound has one or more asymmetric centers, two or more stereoisomers (for example, enantiomer and diastereomer) may exist. The present compound may encompass all these stereoisomers and a mixture of two or more arbitrary stereoisomers.

Also when the present compound contains geometric isomers due to a double bond and the like, two or more geometric isomers (for example, each E/Z or trans/cis isomer, each S-trans/S-cis isomer and the others) may exist. The present compound may encompass all these geometric isomers and a mixture of two or more arbitrary geometric isomers.

As an embodiment of the present compound, the following compounds are included for example.

a compound wherein m is 2;
a compound wherein n is 3;
a compound wherein m is 2 and n is 3;
a compound wherein X is S;
a compound wherein $R^2$ is a hydrogen atom;
a compound wherein $R^3$ is a hydrogen atom;
a compound wherein a moiety represented by a formula:

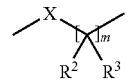

in the formula (I) represents —S—$CH_2CH_2$—, —S—$CH_2CH(CH_3)$—, —S—$CH(CH_3)CH_2$—, —O—$CH_2CH_2$—, —S(O)—$CH_2CH_2$—, —S(O)—$CH_2CH$($CH_3$)—, —S(O)$_2$—$CH_2CH_2$—, —S(O)$_2CH_2CH(CH_3)$—, —S—$CH_2C(CH_3)_2$—, —S—$CH_2C$(cyclopropyl)-, —S—$CH_2CH(C_2H_5)$—, —S—$CH_2$— or —S—$CH_2CH_2CH_2$—;

a compound wherein $R^4$ represents a phenyl group, a 2-pyridyl group, a 3-pyridyl group, a 4-pyridyl group, a 2-pyrimidinyl group, a 2-pyrazinyl group, a 3-pyridazinyl group or a 3-furyl group;

a compound wherein Z is a phenyl group or an $C_{1-6}$ alkyl group optionally having one or more halogen atoms;

a pyrone compound wherein
m is 1, 2 or 3;
n is 1, 2 or 3;
X represents O, S, S(O) or S(O)$_2$;
$R^1$ represents a hydrogen atom;
$R^2$ and $R^3$ represent independently of each other a hydrogen atom or an $C_{1-6}$ alkyl group, alternatively $R^2$ and $R^3$ connect each other to represent an $C_{2-5}$ alkylene chain;
$R^4$ represents an $C_{6-10}$ aryl group or a five- to six-membered heteroaryl group (with the proviso that the $C_{6-10}$ aryl group and the five- to six-membered heteroaryl group may have optionally one or more substituents selected from the group consisting of a halogen atom, a cyano group, a nitro group, a pentafluorothio group, an $C_{1-6}$ alkyl group and an $C_{1-6}$ alkoxy group, and when two or more substituents exist, the substituents may be same or different to each other; and the $C_{1-6}$ alkyl group and the $C_{1-6}$ alkoxy group may have optionally one or more halogen atoms);

G represents a hydrogen atom or a group of any one of the following formulae:

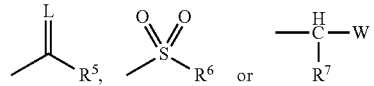

{wherein
L represents an oxygen atom;
$R^5$ represents an $C_{1-6}$ alkyl group, an $C_{1-6}$ alkoxy group, an $C_{3-6}$ alkenyloxy group or an $C_{6-10}$ aryloxy group;
$R^6$ represents an $C_{1-6}$ alkyl group;
$R^7$ represents a hydrogen atom;
W represents an $C_{1-6}$ alkoxy group};
Z represents a halogen atom, a phenyl group, an $C_{1-6}$ alkyl group, an $C_{2-6}$ alkenyl group, an $C_{2-6}$ alkynyl group or a six membered heteroaryloxy group (with the proviso that the phenyl group and the six membered heteroaryloxy group may have optionally one or more substituents selected from the group consisting of a halogen atom and a $C_{1-6}$ haloalkyl group, and when two or more substituents exist, the substituent may be same or different to each other)].

The herbicide of the present invention comprises the present compound and inert carriers (hereinafter, sometimes referred to as "the present herbicide"). The present herbicide can be usually prepared by further adding auxiliary agents for formulation such as surfactants, stickers, dispersers and stabilizers to formulate into wettable powders, water dispersible granules, flowables, granules, dry flowables, emulsifiable concentrates, aqueous solutions, oil solutions, smoking agents, microcapsules and the others. The present herbicide usually contains the present compound in 0.1 to 80% by weight.

The inert carrier includes a solid carrier, a liquid carrier and a gaseous carrier.

Examples of the solid carrier include clays (for example, kaolin, diatomaceous earth, synthetic hydrated silicon dioxide, Fubasami clay, bentonite and acid clay), talcs or the other inorganic minerals (for example, sericite, quartz powder, sulfur powder, activated charcoal, calcium carbonate and hydrated silica) in the form of fine powders or particulates, and examples of the liquid carries include water, alcohols (for example, methanol and ethanol), ketones (for example, acetone and methyl ethyl ketone), aromatic hydrocarbons (for example, benzene, toluene, xylene, ethylbenzene and methyl naphthalene), aliphatic hydrocarbons (for example, n-hexane, cyclohexane and kerosene), esters (for example, ethyl acetate and butyl acetate), nitriles (for example, acetonitrile and isobutyronitrile), ethers (for example, dioxane and diisopropylether), acid amides (for example, N,N-dimethyl formamide and dimethylacetamide), halogenated hydrocarbons (for example, dichloroethane, trichloro ethylene and carbon tetrachloride) and the others.

Examples of the surfactants include alkyl sulfates, alkyl sulfonates, alkyl aryl sulfonates, alkyl aryl ethers and polyoxyethylenated compounds thereof, polyethylene glycol ethers, polyol esters and sugar alcohol derivatives Examples of other auxiliary agents for formulation include stickers and dispersers, specifically casein, gelatin, polysaccharides (for example, starch, gum arabic, cellulose derivatives and alginic acid), lignin derivatives, bentonite, sugars, water-soluble synthetic polymers (for example, polyvinyl alcohol, polyvinyl pyrrolidone and polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, fatty acids or fatty acid esters thereof and the others.

The method for controlling weeds of the present invention comprises applying an effective amount of the present compound to weeds or to a soil where weeds grow (hereinafter, sometimes referred as to "the present weeds controlling method"). In the method for controlling weeds of the present invention, the present herbicide is usually used. The method of application comprises, for example, a foliage treatment of the weeds using the present herbicide, a treatment of the soil surface where the weeds grow, and a soil incorporation treatment of the soil where the weeds grow. In the present weeds controlling method, the present compound is applied in amount of usually 1 to 5,000 g and preferably 10 to 1,000 g per 10,000 m² of area to be controlled weeds.

The present compound can be applied to an agricultural land and the others where "plant" as below-mentioned is cultivated.

"Plant":
Crops:
corn, rice, wheat, barley, rye, oat, *sorghum*, cotton, soybean, peanut, buckwheat, beet, rapeseed, sunflower, sugar cane, tobacco, hop, and the others;
Vegetables:
solanaceous vegetables (for example, eggplant, tomato, pimento, pepper and potato),
cucurbitaceous vegetables (for example, cucumber, pumpkin, zucchini, water melon and melon),
cruciferous vegetables (for example, Japanese radish, white turnip, horseradish, kohlrabi, Chinese cabbage, cabbage, leaf mustard, broccoli and cauliflower),
asteraceous vegetables (for example, burdock, crown daisy, artichoke and lettuce),
liliaceous vegetables (for example, green onion, onion, garlic and asparagus),
ammiaceous vegetables (for example, carrot, parsley, celery and parsnip),
chenopodiaceous vegetables (for example, spinach and Swiss chard),
lamiaceous vegetables (for example, *Perilla frutescens*, mint and basil),
strawberry, sweet potato, *Dioscorea japonica*, colocasia and the others;
Fruits:
pomaceous fruits (for example, apple, pear, Japanese pear, Chinese quince and quince),
stone fleshy fruits (for example, peach, plum, nectarine, *Prunus mume*, cherry fruit, apricot and prune),
*citrus* fruits (for example, *Citrus unshiu*, orange, lemon, lime and grapefruit),
nuts (for example, chestnut, walnuts, hazelnuts, almond, pistachio, cashew nuts and macadamia nuts),
berry fruits (for example, blueberry, cranberry, blackberry and raspberry),
grape, kaki persimmon, olive, Japanese plum, banana, coffee, date palm, coconuts, oil palm and the others;
Trees other than fruit trees:
tea, mulberry,
flowering plant (for example, dwarf azalea, camellia, hydrangea, sasanqua, *Illicium anisatum*, cherry trees, tulip tree, crape myrtle and fragrant olive),
roadside trees (for example, ash, birch, dogwood, *Eucalyptus, Ginkgo biloba*, lilac, maple, *Quercus*, poplar, Judas tree, *Liquidambar formosana*, plane tree, zelkova, Japanese arborvitae, fir wood, hemlock, juniper, *Pinus, Picea, Taxus cuspidate*, elm and Japanese horse chestnut), Sweet viburnum, *Podocarpus macrophyllus*, Japanese cedar, Japanese cypress, croton, Japanese spindletree and *Photinia glabra*);
Others:
flowers (for example, rose, carnation, *chrysanthemum, Eustoma, gypsophila, gerbera*, marigold, *salvia, petunia, verbena*, tulip, aster, gentian, lily, pansy, cyclamen, orchid, lily of the valley, lavender, stock, ornamental cabbage, *primula*, poinsettia, *gladiolus*, cattleya, daisy, cymbidium and *begonia*),
bio-fuel plants (for example, jatropha, safflower, Camelina, switch grass, *Miscanthus giganteus, Phalaris arundinacea, Arundo donax*, Kenaf (*Hibiscus cannabinus*), cassava (*Manihot esculenta*), willow (Salicaceae), etc.), and ornamental foliage plants, and the others.

The "crops" include genetically modified crops.

The present compound can be mixed or combined with other herbicides, phytotoxicity reducing agents, plant growth regulators, pesticides, miticides, nematicides, fungicides and/or synergists.

Examples of the active ingredient as the herbicides include the followings:

(1) Phenoxy Aliphatic Acid Herbicides
    2,4-PA, MCP, MCPB, phenothiol, mecoprop, fluroxypyr, triclopyr, clomeprop, naproanilide and the others;
(2) Benzoic Acid Herbicides
    2,3,6-TBA, dicamba, clopyralid, picloram, aminopyralid, quinclorac, quinmerac and the others;
(3) Urea Herbicides
    diuron, linuron, chlortoluron, isoproturon, fluometuron, isouron, tebuthiuron, methabenzthiazuron, cumyluron, daimuron, methyl-daimuron and the others;
(4) Triazine Herbicides
    atrazine, ametoryn, cyanazine, simazine, propazine, simetryn, dimethametryn, prometryn, metribuzin, triaziflam, indaziflam and the others;
(5) Bipyridinium Herbicides
    paraquat, diquat and the others;
(6) Hydroxybenzonitrile Herbicides
    bromoxynil, ioxynil and the others;
(7) Dinitroaniline Herbicides
    pendimethalin, prodiamine, trifluralin and the others;
(8) Organophosphorous Herbicides
    amiprofos-methyl, butamifos, bensulide, piperophos, anilofos, glyphosate, glufosinate, glufosinate-P, bialaphos and the others;
(9) Carbamate Herbicides
    di-allate, tri-allate, EPTC, butylate, benthiocarb, esprocarb, molinate, dimepiperate, swep, chlorpropham, phenmedipham, phenisopham, pyributicarb, asulam and the others;
(10) Acid Amide Herbicides
    propanil, propyzamide, bromobutide, etobenzanid and the others;
(11) Chloroacetanilide Herbicides
    acetochlor, alachlor, butachlor, dimethenamid, propachlor, metazachlor, metolachlor, pretilachlor, thenylchlor, pethoxamid and the others;
(12) Diphenyl Ether Herbicides
    acifluorfen-sodium, bifenox, oxyfluorfen, lactofen, fomesafen, chlomethoxynil, aclonifen and the others;
(13) Cyclic Imide Herbicide
    oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, benzfendizone, bencarbazone, saflufenacil and the others;
(14) Pyrazole Herbicides
    benzofenap, pyrazolate, pyrazoxyfen, topramezone, pyrasulfotole and the others;
(15) Triketone Herbicides
    isoxaflutole, benzobicyclon, sulcotrione, mesotrione, tembotrione, tefuryltrione, bicyclopyrone and the others;
(16) Aryloxyphenoxypropionic Acid Herbicides
    clodinafop-propargyl, cyhalofop-butyl, diclofop-methyl, fenoxaprop-ethyl, fluazifop-butyl, haloxyfop-methyl, quizalofop-ethyl, metamifop and the others;
(17) Trione Oxyme Herbicides
    alloxydim-sodium, sethoxydim, butroxydim, clethodim, cloproxydim, cycloxydim, tepraloxydim, tralkoxydim, profoxydim and the others;
(18) Sulfonylurea Herbicides
    chlorsulfuron, sulfometuron-methyl, metsulfuron-methyl, chlorimuron-ethyl, tribenuron-methyl, triasulfuron, bensulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl-sodium, foramsulfuron, mesosulfuron-methyl, trifloxysulfuron, tritosulfuron, orthosulfamuron, flucetosulfuron, propyrisulfuron, metazosulfuron, iofensulfuron-sodium and the others;
(19) Imidazolinone Herbicides
    imazamethabenz-methyl, imazamox, imazapic, imazapyr, imazaquin, imazethapyr and the others;
(20) Sulfonamide Herbicides
    flumetsulam, metosulam, diclosulam, florasulam, cloransulam-methyl, penoxsulam, pyroxsulam and the others;
(21) Pyrimidinyloxy Benzoic Acid Herbicides
    pyrithiobac-sodium, bispyribac-sodium, pyriminobac-methyl, pyribenzoxim, pyriftalid, pyrimisulfan, triafamone and the others; and
(22) Other Systematic Herbicides
    bentazone, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, pyraclonil, pyroxasulfone, thiencarbazone-methyl, aminocyclopyrachlor, ipfencarbazone, methiozolin, fenoxasulfone and the others.

Examples of the active ingredient as the phytotoxicity reducing agents include the followings:
    benoxacor, cloquintocet-mexyl, cyometrinil, dichlormid, fenchlorazole-ethyl, fenclorim, flurazole, furilazole, mefenpyr-diethyl, MG191, oxabetrinil, allidochlor, isoxadifen-ethyl, cyprosulfamide, fluxofenim, 1,8-naphthalic anhydride, AD-67 and the others.

Examples of the active ingredient as the plant growth regulators include the followings:
    hymexazol, paclobutrazol, uniconazole-P, inabenfide, prohexadione-calcium, aviglycine, 1-naphthalene acetamide, abscisic acid, indolebutyric acid, ethychlozate, ethephon, cloxyfonac, chlormequat, dichlorprop, gibberellins, prohydrojasmon, benzyladenine, forchlorfenuron, maleic hydrazide, calcium peroxide, mepiquat-chloride, 4-CPA (4-chlorophenoxyacetic acid) and the others.

Examples of the active ingredient as the pesticides include the followings:
(1) Organophosphorous Compound
    acephate, butathiofos, chlorethoxyfos, chlorfenvinphos, chlorpyrifos, chlorpyrifos-methyl, cyanophos (abbrev: CYAP), diazinon, dichlofenthion (abbrev: ECP), dichlorvos (abbrev: DDVP), dimethoate, dimethylvinphos, disulfoton, EPN, ethion, ethoprophos, etrimfos, fenthion (abbrev: MPP), fenitrothion (abbrev: MEP), fosthiazate, formothion, isofenphos, isoxathion, malathion, mesulfenfos, methidathion (abbrev: DMTP), monocrotophos, naled (abbrev: BRP), oxydeprofos (abbrev: ESP), parathion, phosalone, phosmet (abbrev: PMP), pirimiphos-methyl, pyridafenthion, quinalphos, phenthoate (abbrev: PAP), profenofos, propaphos, prothiofos, pyraclorfos, salithion, sulprofos, tebupirimfos, temephos, tetrachlorvinphos, terbufos, thiometon, trichlorphon (abbrev: DEP), vamidothion, phorate, cadusafos and the others;
(2) Carbamate Compounds
    alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb (abbrev: MIPC), metolcarb, methomyl, methiocarb, oxamyl, pirimicarb, propoxur (abbrev: PHC), XMC, thiodicarb, xylylcarb, aldicarb and the others;
(3) Pyrethroid Compounds
    acrinathrin, allethrin, beta-cyfluthrin, bifenthrin, cycloprothrin, cyfluthrin, cyhalothrin, cypermethrin, empenthrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, profluthrin, dimefluthrin, 2,3,5,6-tetrafluoro-4-(methoxymethyl)benzyl 2,2-dimethyl-3-(2-cyano-1-propenyl)cyclopropanecarboxylate, 2,3,5,6-tetrafluoro-4-(methoxymethyl)benzyl 2,2,3,3-tetramethylcyclopropanecarboxylate, protrifenbute and the others;

(4) Nereis Toxin Compounds
cartap, bensultap, thiocyclam, monosultap, bisultap;

(5) Neonicotinoid Compounds and the Others;
imidacloprid, nitenpyram, acetamiprid, thiamethoxam, thiacloprid, dinotefuran, clothianidin and the others;

(6) Benzoylurea Compounds
chlorfluazuron, bistrifluron, diflubenzuron, fluazuron, flucycloxuron, flufenoxuron, hexaflumuron, lufenuron, novaluron, noviflumuron, teflubenzuron, triflumuron and the others;

(7) Phenylpyrazole Compounds
acetoprole, ethiprole, fipronil, vaniliprole, pyriprole, pyrafluprole and the others;

(8) Bt Toxins
live spores and crystal toxins originated from *Bacillus thuringiensis* and a mixture thereof;

(9) Hydrazine Compounds
chromafenozide, halofenozide, methoxyfenozide, tebufenozide and the others;

(10) Organochlorine Compounds
aldrin, dieldrin, chlordane, DDT, dienochlor, endosulfan, methoxychlor and the others; and

(11) Other Pesticide Active Ingredients
machine oil, nicotine-sulfate; avermectin-B, bromopropylate, buprofezin, chlorphenapyr, cyromazine, DCIP (dichlorodiisopropyl ether), D-D (1,3-Dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, aluminium phosphide, arsenous oxide, benclothiaz, calcium cyanamide, calcium polysulfide, DSP, flonicamid, flurimfen, formetanate, hydrogen phosphide, metam-ammonium, metam-sodium, methyl bromide, potassium oleate, spiromesifen, Sulfoxaflor, sulfur, metaflumizone, spirotetramat, pyrifluquinazone, spinetoram, chlorantraniliprole, tralopyril, diafenthiuron and the others.

A compound of formula (A):

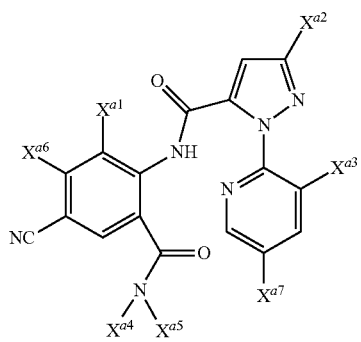

wherein)

$X^{a1}$ represents a methyl group, a chlorine atom, a bromine atom or a fluorine atom, $X^{a2}$ represents a fluorine atom, a chlorine atom, a bromine atom, a $C_1$-$C_4$ haloalkyl group or a $C_1$-$C_4$ haloalkoxy group, $X^{a3}$ represents a fluorine atom, a chlorine atom or a bromine atom, $X^{a4}$ represents an optionally substituted $C_1$-$C_4$ alkyl group, an optionally substituted $C_3$-$C_4$ alkenyl group, an optionally substituted $C_3$-$C_4$ alkynyl group, an optionally substituted $C_3$-$C_5$ cycloalkylalkyl group or a hydrogen atom, $X^{a5}$ represents a hydrogen atom or a methyl group, $X^{a6}$ represents a hydrogen atom, a fluorine atom or a chlorine atom, and $X^{a7}$ represents a hydrogen atom, a fluorine atom or a chlorine atom.

A compound of formula (B):

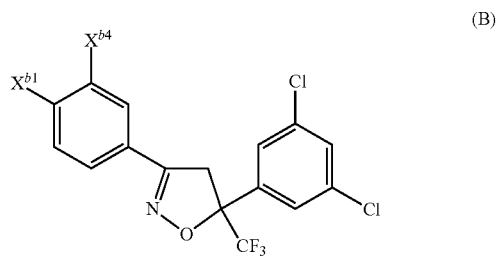

wherein $X^{b1}$ represents a $X^{b2}$—NH—C(=O) group, a $X^{b2}$—C(=O)—NH—CH$_2$ group, a $X^{b3}$—S(O) group, an optionally substituted pyrrol-1-yl group, an optionally substituted imidazol-1-yl group, an optionally substituted pyrazol-1-yl group or an optionally substituted 1,2,4-triazol-1-yl group, $X^{b2}$ represents an optionally substituted $C_1$-$C_4$ haloalkyl group such as a 2,2,2-trifluoroethyl group or an optionally substituted $C_3$-$C_6$ cycloalkyl group such as a cyclopropyl group, $X^{b3}$ represents an optionally substituted $C_1$-$C_4$ alkyl group such as a methyl group, and $X^{b4}$ represents a hydrogen atom, a chlorine atom, a cyano group or a methyl group.

A compound of formula (C):

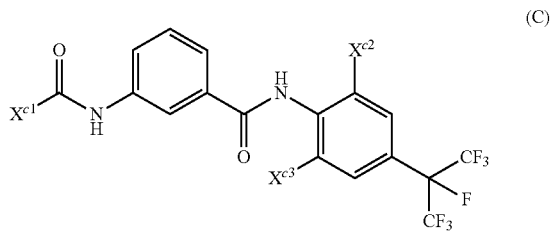

wherein $X^{c1}$ represents an optionally substituted $C_1$-$C_4$ alkyl group such as a 3,3,3-trifluoropropyl group, an optionally substituted $C_1$-$C_4$ alkoxy group such as a 2,2,2-trichloroethoxy group, an optionally substituted phenyl group such as a 4-cyanophenyl group or an optionally substituted pyridyl group such as a 2-chloro-3-pyridyl group, $X^{c2}$ represents a methyl group or a trifluoromethylthio group, and $X^{c3}$ represents a methyl group or a halogen atom.

Examples of the active ingredient as the miticides include the followings:

acequinocyl, amitraz, benzoximate, bifenazate, bromopropylate, chinomethionat, chlorobenzilate, CPCBS (chlorfenson), clofentezine, cyflumetofen, kelthane (which is also referred to as dicofol), etoxazole, fenbutatin oxide, fenothiocarb, fenpyroximate, fluacrypyrim, halfenprox, hexythiazox, propargite (abbrev: BPPS), polynactins, pyridaben, pyrimidifen, tebufenpyrad, tetradifon, spirodiclofen, spiromesifen, spirotetramat, amidoflumet, cyenopyrafen and the others.

Examples of the active ingredient as the nematicides include the followings:

DCIP, fosthiazate, levamisol, methyisothiocyanate, morantel tartarate, imicyafos and the others.

Examples of the active ingredient as the fungicides include the followings:

(1) Polyhaloalkylthio Compounds captan, folpet and the others;

(2) Organophosphorous Compounds

IBP, EDDP, tolclofos-methyl and the others;

(3) Benzimidazole Compounds benomyl, carbendazim, thiophanate-methyl, thiabendazole and the others;

(4) Carboxyamide Compounds carboxin, mepronil, flutolanil, thifluzamid, furametpyr, boscalid, penthiopyrad and the others;

(5) Dicarboxyimide Compounds procymidone, iprodione, vinclozolin and the others;

(6) Acylalanine Compounds metalaxyl and the others;

(7) Azole Compounds triadimefon, triadimenol, propiconazole, tebuconazole, cyproconazole, epoxiconazole, prothioconazole, ipconazole, triflumizole, prochloraz, penconazole, flusilazole, diniconazole, bromuconazole, difenoconazole, metconazole, tetraconazole, myclobutanil, fenbuconazole, hexaconazole, fluquinconazole, triticonazole, bitertanol, imazalil, flutriafol and the others;

(8) Morpholine Compounds dodemorph, tridemorph, fenpropimorph and the others;

(9) Strobilurin Compounds azoxystrobin, kresoxim-methyl, metominostrobin, trifloxystrobin, picoxystrobin, pyraclostrobin, fluoxastrobin, dimoxystrobin and the others;

(10) Antibiotics validamycin A, blasticidin S, kasugamycin, polyoxin and the others;

(11) Dithiocarbamate Compounds mancozeb, maneb, thiuram and the others; and

(12) Other Fungicidal Active Ingredients fthalide, probenazole, isoprothiolane, tricyclazole, pyroquilon, ferimzone, acibenzolar S-methyl, carpropamid, diclocymet, fenoxanil, tiadinil, diclomezine, teclofthalam, pencycuron, oxolinic acid, TPN, triforine, fenpropidin, spiroxamine, fluazinam, iminoctadine, fenpiclonil, fludioxonil, quinoxyfen, fenhexamid, silthiofam, proquinazid, cyflufenamid, bordeaux mixture, dichlofluanid, cyprodinil, pyrimethanil, mepanipyrim, diethofencarb, pyribencarb, famoxadone, fenamidone, zoxamide, ethaboxam, amisulbrom, iprovalicarb, benthiavalicarb, cyazofamid, mandipropamid, metrafenone, fluopiram, bixafen and the others.

Examples of the active ingredient as the synergists include the followings:

piperonyl butoxide, sesamex, sulfoxide, N-(2-ethylhexyl)-8,9,10-trinorborn-5-ene-2,3-dicarboximide (MGK 264), N-declyimidazole), WARF-antiresistan, TBPT, TPP, IBP, PSCP, methyl iodide ($CH_3I$), t-phenylbutenone, diethylmaleate, DMC, FDMC, ETP, ETN and the others.

Examples of the subjects to be controlled by the present herbicide include the followings:

Weeds:

*Digitaria ciliaris, Eleusine indica, Setaria viridis, Setaria faberi, Setaria glauca, Echinochloa crus-galli, Panicum dichotomiflorum, Panicum texanum, Brachiaria platyphylla, Brachiaria plantaginea, Brachiaria decumbens, Sorghum halepense, Andropogon sorghum, Cynodon dactylon, Avena fatua, Lolium multiflorum, Alopecurus myosuroides, Bromus tectorum, Bromus sterilis, Phalaris minor, Apera spicaventi, Poa annua, Agropyron repens, Cyperus iria, Cyperus rotundus, Cyperus esculentus, Portulaca oleracea, Amaranthus retroflexus, Amaranthus hybridus, Amaranthus palmeri, Amaranthus rudis, Abutilon theophrasti, Sida spinosa, Fallopia convolvulus, Polygonum scabrum, Persicaria pennsylvanica, Persicaria vulgaris, Rumex crispus, Rumex obtusifolius, Fallopia japonica, Chenopodium album, Kochia scoparia, Polygonum longisetum, Solanum nigrum, Datura stramonium, Ipomoea purpurea, Ipomoea hederacea, Ipomoea hederacea* var. *integriuscula, Ipomoea lacunosa, Convolvulus arvensis, Lamium purpureum, Lamium amplexicaule, Xanthium pensylvanicum, Helianthus annuus, Matricaria perforata* or *inodora, Matricaria chamomilla, Chrysanthemum segetum, Matricaria matricarioides, Ambrosia artemisiifolia, Ambrosia trifida, Erigeron canadensis, Artemisia princeps, Solidago altissima, Conyza bonariensis, Sesbania exaltata, Cassia obtusifolia, Desmodium tortuosum, Trifolium repens, Pueraria lobata, Vicia angustifolia, Commelina communis, Commelina benghalensis, Galium aparine, Stellaria media, Raphanus raphanistrum, Sinapis arvensis, Capsella bursapastoris, Veronica persica, Veronica hederifolia, Viola arvensis, Viola tricolor, Papaver rhoeas, Myosotis scorpioides, Asclepias syriaca, Euphorbia helioscopia, Chamaesyce nutans, Geranium carolinianum, Erodium cicutarium, Equisetum arvense, Leersia japonica, Echinochloa oryzicola, Echinochloa crus-galli* var. *formosensis, Leptochloa chinensis, Cyperus difformis, Fimbristylis miliacea, Eleocharis acicularis, Scirpus juncoides, Scirpus wallichii, Cyperus serotinus, Eleocharis kuroguwai, Bolboschoenus koshevnikovii, Schoenoplectus nipponicus, Monochoria vaginalis, Lindernia procumbens, Dopatrium junceum, Rotala indica, Ammannia multiflora, Elatine triandra, Ludwigia epilobioides, Sagittaria pygmaea, Alisma canaliculatum, Sagittaria trifolia, Potamogeton distinctus, Oenanthe javanica, Callitriche palustris, Lindernia micrantha, Lindernia dubia, Eclipta prostrata, Murdannia keisak, Paspalum distichum, Leersia oryzoides* and the others;

Aquatic Plants:

*Alternanthera philoxeroides, Limnobium spongia, Ceratopteris* (*Salvinia* sp.), *Pistia stratiotes, Hydrotyle verticillata* (*Hydrocotyle* sp.), filamentous algae (*Pithophora* sp., *Cladophora* sp.), *Ceratophyllum demersum*, duckweed (*Lemna* sp.), *Cabomba caroliniana, Hydrilla verticillata, Najas guadalupensis*, pond weeds (*Potamogeton crispus, Potamogeton illinoensis, Potamogeton pectinatus* and the like), watermeals (*Wolffia* sp.), watermillfoils (*Myriophyllum spicatum, Myriophyllum heterophyllum* and the like), *Eichhornia crassipes* and the others;

Moss, Liverworts, Hornworts;

*Cyanobacterium;*

Fern;

Sucher of perennial plants (such as pomaceous fruits, stone fleshy fruits, berry fruits, nuts, *citrus* fruits, hop and grape).

The present compound can be prepared for example, according to the below-mentioned process.

Process 1

The present compound of formula (1a) wherein represents a hydrogen atom can be prepared by reacting a compound of formula (2a) and a compound of formula (3) in the presence of a base.

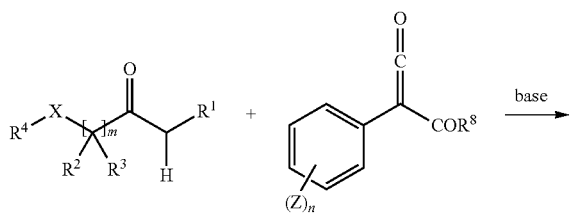

(2a)            (3)

→

(1a)

[wherein, $R^1$, $R^2$, $R^3$, $R^4$, X, n, m and Z are the same as defined above; $R^8$ represents a halogen atom (such as a fluorine atom, a chlorine atom, a bromine atom, an iodine atom), preferably a chlorine atom]

The reaction is usually carried out in a solvent. Examples of the solvent to be used in the reaction include aromatic hydrocarbons such as benzene, toluene and xylene; ethers such as diethyl ether, diisopropylether, dioxane, tetrahydrofuran and dimethoxyethane; halogenated hydrocarbons such as dichloromethane, chloroform and 1,2-dichloroethane; amides such as dimethylformamide and dimethylacetamide; sulfones such as sulfolane; and mixed solvents thereof, and preferably include aromatic hydrocarbons such as xylene.

Examples of the base to be used in the reaction includes alkaline metal amides such as lithium diisopropylamide, sodium bis(trimethylsilyl)amide, lithium bis(trimethylsilyl)amide and potassium bis(trimethylsilyl)amide; organic bases such as triethylamine, tripropylamine, pyridine, dimethylaminopyridine, 1,8-diazabicyclo[5.4.0]-7-undecene and N,N-diisopropylethylamine; metal alkoxides such as potassium tert-butoxide; and alkali metal hydrides such as sodium hydride, and preferably alkaline metal amides such as lithium diisopropylamide.

The amount used of the base used in the reaction is usually within a range of 1 to 10 molar equivalents and preferably within a range of 1 to 2 molar equivalents as opposed to 1 mole of the compound of formula (2a). The amount used of the compound of formula (3) used in the reaction is usually within a range of 1 to 3 molar equivalents as opposed to 1 mole of the compound of formula (2).

The reaction temperature is usually within a range of −80 to 200° C. The reaction period of the reaction is usually within a range of 10 minutes to 30 hours.

The completion of the reaction can be confirmed by sampling a part of the reaction mixtures followed by performing analytical means such as thin-layer chromatography and high-performance liquid chromatography. When the reaction is completed, for example, the reaction mixtures are acidified with an acid, are mixed with water, and are extracted with an organic solvent, and the resulting organic layers are treated (for example, drying and concentration) to obtain the compound of formula (1a).

The compound of formula (2a) is a known compound, or may be prepared from a known compound, and may be prepared, for example, according to the process described in Tetrahedron letter 28 (1987) 2893-2894, Tetrahedron letter 47 (2006) 5869-5873, Tetrahedron letter 42 (1986) 6071-6095, JP 63-146856 or similar processes thereto.

Process 2

The present compound of formula (1a) wherein G represents a hydrogen atom can be prepared also by reacting a compound of formula (2b) and a compound of formula (3) in the presence of a base.

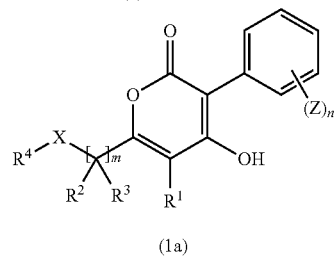

(2b)            (3)

→

(1a)

[wherein, $R^1$, $R^2$, $R^3$, $R^4$, $R^8$, X, n, m and Z are the same as defined above; $R^9$, $R^{10}$ and $R^{11}$ represent independently of each other a methyl group, an ethyl group, a t-butyl group, a diisopropyl group or a phenyl group, and preferably a methyl group]

The reaction is usually carried out in a solvent. Examples of the solvent to be used in the reaction include aromatic hydrocarbons such as benzene, toluene and xylene; ethers such as diethyl ether, diisopropylether, dioxane, tetrahydrofuran and dimethoxyethane; halogenated hydrocarbons such as dichloromethane, chloroform and 1,2-dichloroethane; amides such as dimethylformamide and dimethylacetamide; sulfones such as sulfolane; and mixed solvents thereof, and preferably include aromatic hydrocarbons such as xylene.

The amount used of the compound of formula (3) used in the reaction is usually within a range of 1 to 3 molar equivalents as opposed to 1 mole of the compound of formula (2b).

The reaction temperature is usually within a range of −60 to 200° C. The reaction period of the reaction is usually within a range of 10 minutes to 30 hours.

The completion of the reaction can be confirmed by sampling a part of the reaction mixtures followed by performing analytical means such as thin-layer chromatography and high-performance liquid chromatography. When the reaction is completed, for example, the reaction mixtures are acidified with an acid, are mixed with water, and are extracted with an organic solvent, and the resulting organic layers are treated (for example, drying and concentration) to obtain the compound of the formula (1a).

Process 3

The present compound of formula (1b) wherein G represents a group other than a hydrogen atom can be prepared by reacting a compound of formula (1a) and a compound of formula (4).

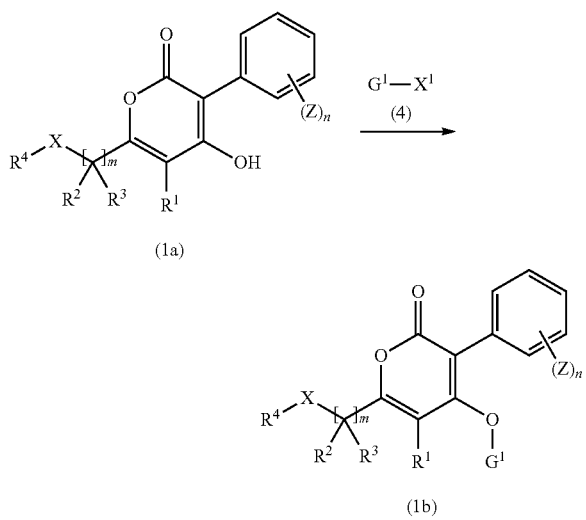

[wherein $G^1$ represents a group of any one of the formulae:

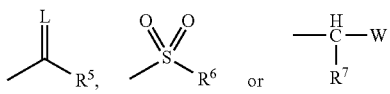

(wherein L, $R^5$, $R^6$, $R^7$ and W are the same as defined above);

$X^1$ represents a halogen atom (for example, a chlorine atom, a bromine atom, an iodine atom and the like) or an $C_{1-3}$ alkylsulfonyloxy group optionally substituted with one or more halogen atoms (for example, a methylsulfonyloxy group, a trifluoromethylsulfonyloxy group) or a group of a formula: $OG^1$ (with the proviso that when $G^1$ represents a group of formula:

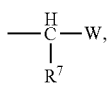

$X^1$ represents a halogen atom or an $C_{1-3}$ alkylsulfonyloxy group optionally substituted with one or more halogen atoms); and $R^1$, $R^2$, $R^3$, $R^4$, X, n, m and Z are the same as defined above]

The reaction can be carried in a solvent. Examples of the solvent to be used includes aromatic hydrocarbons such as benzene and toluene; ethers such as diethyl ether, diisopropylether, dioxane, tetrahydrofuran and dimethoxyethane; halogenated hydrocarbons such as dichloromethane, chloroform and 1,2-dichloroethane; amides such as dimethylformamide and dimethylacetamide; sulfoxides such as dimethyl sulfoxide; sulfones such as sulfolane; and mixed solvents thereof.

Examples of the compound of formula (4) to be used in the reaction include carboxylic halides such as acetyl chloride, propionyl chloride, isobutyryl chloride, pivaloyl chloride, benzoyl chloride and cyclohexanecarboxylic acid chloride; carboxylic anhydrides such as acetic anhydride and trifluoroacetic anhydride; halides of carbonate half ester such as methyl chloroformate, ethyl chloroformate and phenyl chloroformate; carbamic halides such as dimethylcarbamoyl chloride; sulfonic halides such as methanesulfonyl chloride and p-toluenesulfonyl chloride; sulfonic anhydrides such as methanesulfonic anhydride and trifluoromethanesulfonic anhydride; alkyl halogenoalkyl ethers such as chloromethyl methyl ether and ethyl chloromethyl ether.

The amount used of the compound of formula (4) used in the reaction is usually within a range of 1 molar equivalent or more and preferably within a range of 1 to 3 molar equivalents as opposed to 1 mole of the compound of formula (1a).

The reaction is usually carried out in the presence of a base. Examples of the base to be used in the reaction include organic bases such as triethylamine, tripropylamine, pyridine, dimethylaminopyridine, 1,8-diazabicyclo[5.4.0]-7-undecene; and inorganic bases such as sodium hydroxide, potassium hydroxide, calcium hydroxide, sodium carbonate, potassium carbonate, sodium hydrogen carbonate, calcium carbonate and sodium hydride. The amount used of the base is usually within a range of 0.5 to 10 molar equivalents and preferably within a range of 1 to 5 molar equivalents as opposed to 1 mole of the compound of formula (1a).

The reaction temperature is usually within a range of −30 to 180° C. and preferably within a range of −10 to 50° C. The reaction period of the reaction is usually within a range of 10 minutes to 30 hours.

The completion of the reaction can be confirmed by sampling a part of the reaction mixtures followed by performing analytical means such as thin-layer chromatography and high-performance liquid chromatography. When the reaction is completed, for example, the reaction mixtures are mixed with water and are extracted with an organic solvent, and the resulting organic layers are treated (for example, drying and concentration) to obtain the compound of formula (1b).

The compound of formula (4) is a known compound, or may be prepared from a known compound.

Process 4

The present compound wherein X represents S(O) can be prepared by oxidizing a compound wherein X represents S. When an alkylthio group, an alkylsulfinyl group (the alkylthio group or the alkylsulfinyl group may have optionally one or more halogen atoms or $C_{1-3}$ haloalkyl groups, and when two or more halogen atoms or $C_{1-3}$ haloalkyl groups exist, the halogen atoms or the $C_{1-3}$ haloalkyl groups may be same or different to each other respectively), these groups may be oxidized.

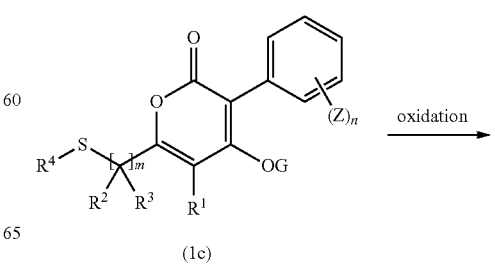

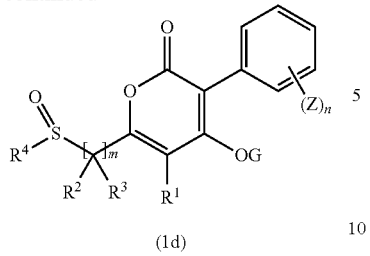

(1d)

[wherein $R^1$, $R^2$, $R^3$, $R^4$, G, n, m and Z are the same as defined above]

An oxidizing agent is used in the reaction. Examples of the oxidizing agent includes hydrogen peroxide; peracids such as peracetic acid, perbenzoic acid and m-chloroperbenzoic acid; sodium periodate, ozone, selenium dioxide, chromic acid, dinitrogen tetraoxide, acetyl nitrate, iodine, bromine, N-bromosuccinimide and iodosylbenzene. The oxidizing agent is used usually within a range of 0.8 to 1.2 molar equivalents as opposed to 1 mole of the compound of formula (1c).

The reaction is carried out in a solvent. Examples of the solvent to be used in the reaction include saturated hydrocarbons such as hexane, heptane, octane and cyclohexane; aromatic hydrocarbons such as benzene, toluene, xylene, chlorobenzene and dichlorobenzene; halogenated hydrocarbons such as dichloromethane, chloroform, 1,2-dichloroethane and carbon tetrachloride; alcohols such as methanol, ethanol and propanol; nitriles such as acetonitrile; amides such as dimethylformamide and dimethylacetamide; sulfones such as sulfolane; organic acids such as acetic acid and propionic acid; and mixed solvents thereof.

The reaction temperature is usually within a range of −50 to 100° C. and preferably within a range of 0 to 50° C.

The reaction period of the reaction is usually within a range of 10 minutes to 10 hours. The completion of the reaction can be confirmed by analyzing a part of the reaction mixtures on analytical means such as thin-layer chromatography and high-performance liquid chromatography. When the reaction is completed, for example, the reaction mixtures are mixed with water and are extracted with an organic solvent, and the resulting organic layers are treated (for example, drying and concentration) to obtain the compound of formula (1d).

Process 5

The present compound wherein X represents $S(O)_2$ can be prepared by oxidizing a compound wherein X represents S or S(O). When an alkylthio group, an alkylsulfinyl group, a haloalkylthio group and/or a haloalkylsulfinyl group is/are contained at any position other than X in a compound of a formula (1e), these groups may be oxidized.

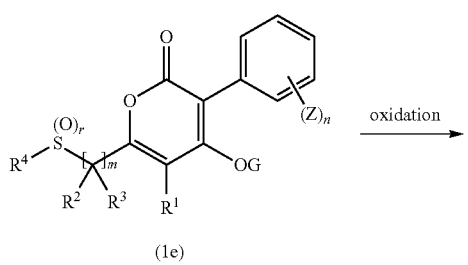

(1e)

r = 0
r = 1

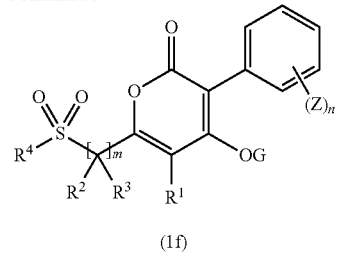

(1f)

[wherein r is 0 or 1, and $R^1$, $R^2$, $R^3$, $R^4$, G, n, m and Z are the same as defined above]

The reaction is usually carried out in a solvent. Examples of the solvent to be used in the reaction include saturated hydrocarbons such as hexane, heptane, octane and cyclohexane; aromatic hydrocarbons such as benzene, toluene, xylene, chlorobenzene and dichlorobenzene; halogenated hydrocarbons such as dichloromethane, chloroform, 1,2-dichloroethane and carbon tetrachloride; alcohols such as methanol, ethanol and propanol; nitriles such as acetonitrile; amides such as dimethylformamide and dimethylacetamide; sulfones such as sulfolane; organic acids such as acetic acid and propionic acid; water; and mixed solvents thereof.

An oxidizing agent is used in the reaction. Examples of the oxidizing agent include hydrogen peroxide; peracids such as peracetic acid, perbenzoic acid and m-chloroperbenzoic acid; sodium metaperiodate, ozone, selenium dioxide, chromic acid, dinitrogen tetraoxide, acetyl nitrate, iodine, bromine, N-bromosuccinimide, iodosylbenzene, a combination of hydrogen peroxide and tungsten catalyst, a combination of hydrogen peroxide and vanadium catalyst, and potassium permanganate.

When the compound of formula (1e) wherein r is 0 is used, the amount used of the oxidizing agent is usually within a range of 2 to 10 molar equivalents and preferably within a range of 2 to 4 molar equivalents opposed to 1 mole of the compound. Also when the compound of formula (1e) wherein r is 1 is used, the amount used of the oxidizing agent is usually within a range of 1 to 10 molar equivalents and preferably within a range of 1 to 3 molar equivalents as opposed to 1 mole of the compound.

The reaction temperature is usually within a range of 0 to 200° C. and preferably 20 to 150° C. The reaction period of the reaction is usually within a range of 30 minutes to 10 hours.

The completion of the reaction can be confirmed by analyzing a part of the reaction mixtures on analytical means such as thin-layer chromatography and high-performance liquid chromatography. When the reaction is completed, for example, the reaction mixtures are mixed with water and are extracted with an organic solvent, and the resulting organic layers are treated (for example, drying and concentration) to obtain the compound of formula (1f).

Process 6

The present compound of formula (1b) can be prepared by reacting a compound of formula (9g) and a compound of formula (8).

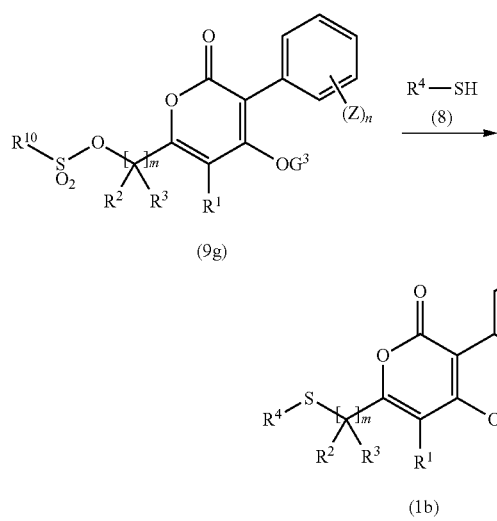

(9g)

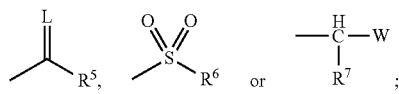

(1b)

[wherein $G^3$ represents a hydrogen atom or a group of any one of the formulae:

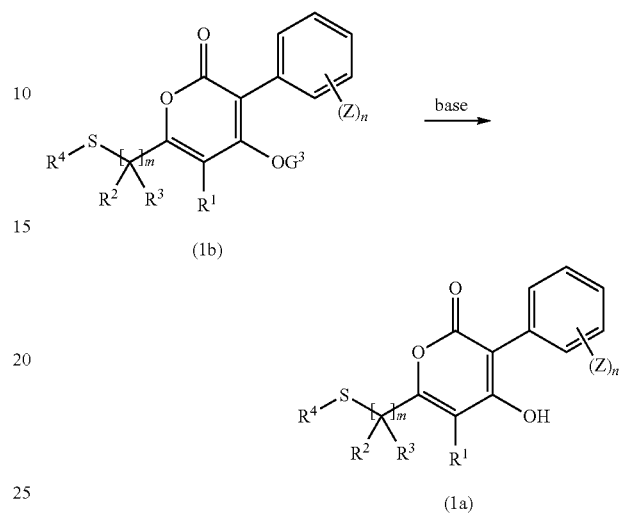

and L, $R^5$, $R^6$, $R^7$ and W are the same as defined above);

$R^{10}$ represents an $C_{1-6}$ alkyl group or an $C_{6-10}$ aryl group (with the proviso that the $C_{1-6}$ alkyl group and the $C_{6-10}$ aryl group may have optionally one or more halogen atoms, and when two or more halogen atoms exist, the halogen atoms may be same or different to each other; and the $C_{6-10}$ aryl group may have optionally one or more $C_{1-6}$ alkyl groups and when two or more $C_{1-6}$ alkyl groups exist, the alkyl groups may be same or different to each other; and $R^1$, $R^2$, $R^3$, $R^4$, n, m and Z are the same as defined above]

The reaction is usually carried out in a solvent. Examples of the solvent include ethers such as diethyl ether, diisopropylether, dioxane, tetrahydrofuran and dimethoxyethane; halogenated hydrocarbons such as dichloromethane, chloroform and 1,2-dichloroethane; amides such as dimethylformamide and dimethylacetamide; and mixed solvents thereof. The amount used of the compound of formula (8) to be used in the reaction is usually within a range of 1 molar equivalent or more and preferably within a range of 1 to 5 molar equivalents as opposed to 1 mole of the compound of formula (9g).

The reaction temperature is usually within a range of −60 to 180° C. and preferably within a range of −10 to 100° C. The reaction period of the reaction is usually within a range of 10 minutes to 30 hours.

The completion of the reaction can be confirmed by analyzing a part of the reaction mixtures on analytical means such as thin-layer chromatography and high-performance liquid chromatography. When the reaction is completed, for example, an acid is added to the reaction mixtures, and the reaction mixtures are then mixed with water and are extracted with an organic solvent, and the resulting organic layers are treated (for example, drying and concentration) to obtain the compound of formula (1b).

Process 7

The present compound of formula (1a) can be prepared by hydrolyzing the compound of formula (1b) in the presence of a base.

[wherein $R^1$, $R^2$, $R^3$, $R^4$, n, m, Z and $G^3$ are the same as defined above]

The reaction is usually carried out in a solvent. Examples of the solvent include ethers such as diethyl ether, diisopropylether, dioxane, tetrahydrofuran and dimethoxyethane; alcohols such as methanol and ethanol; amides such as dimethylformamide and dimethylacetamide; and mixed solvents thereof.

Examples of the base to be used in the reaction include lithium hydroxide, sodium hydroxide, potassium hydroxide, sodium methoxide and sodium ethoxide. The amount used of the base is usually within a range of 1 to 10 molar equivalents and preferably within a range of 1 to 5 molar equivalents as opposed to 1 mole of the compound of formula (1b).

The reaction temperature is usually within a range of −60 to 180° C. and preferably within a range of −10 to 100° C. The reaction period of the reaction is usually within a range of 10 minutes to 30 hours.

The completion of the reaction can be confirmed by analyzing a part of the reaction mixtures on analytical means such as thin-layer chromatography and high-performance liquid chromatography. When the reaction is completed, for example, after an acid is added to the reaction mixtures, the reaction mixtures are mixed with water and are extracted with an organic solvent and the resulting organic layers are treated (for example, drying and concentration) to obtain the compound of the formula (1a).

The compounds that are prepared according to the above-mentioned processes 1 to 7 may be isolated and/or purified by other known means such as concentration, concentration under reduced pressure, extraction, re-extraction, crystallization, recrystallization and chromatography.

Reference Process 1

The present compound of formula (2b) can be prepared, for example, by reacting the compound of formula (2a) and the compound of formula (5) in the presence of a base.

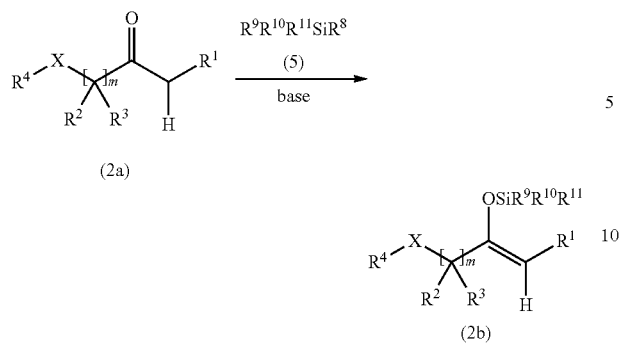

(2a)

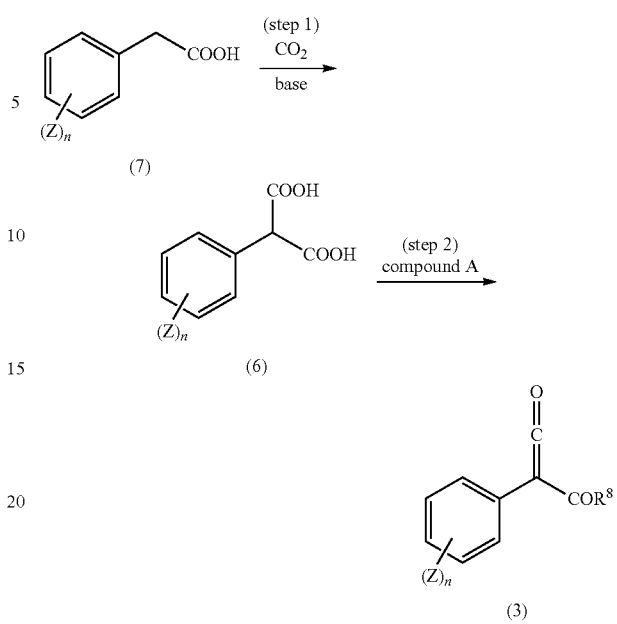

[wherein, $R^1$, $R^2$, $R^3$, $R^4$, $R^8$, $R^9$, $R^{10}$, $R^{11}$, X, n and m are the same as defined above]

The reaction is usually carried out in a solvent. Examples of the solvent to be used in the reaction include aromatic hydrocarbons such as benzene, toluene and xylene; ethers such as diethyl ether, diisopropylether, dioxane, tetrahydrofuran and dimethoxyethane; halogenated hydrocarbons such as dichloromethane, chloroform and 1,2-dichloroethane; amides such as dimethylformamide and dimethylacetamide; sulfones such as sulfolane; and mixed solvents thereof.

The amount used of the compound of formula (5) used in the reaction is usually within a range of 1 molar equivalent or more and preferably within a range of 1 to 3 molar equivalents as opposed to 1 mole of the compound of formula (2a).

Examples of the base to be used in the reaction includes alkaline metal amides such as lithium diisopropylamide, sodium bis(trimethylsilyl)amide, lithium bis(trimethylsilyl) amide and potassium bis(trimethylsilyl)amide; organic bases such as triethylamine, tripropylamine, pyridine, dimethylaminopyridine, 1,8-diazabicyclo[5.4.0]-7-undecene and N,N-diisopropylethylamine; metal alkoxides such as potassium tert-butoxide; and alkali metal hydrides such as sodium hydride, and preferably alkaline metal amides such as lithium diisopropylamide.

The amount used of the base used in the reaction is usually within a range of 1 to 10 molar equivalents and preferably within a range of 1 to 2 molar equivalents as opposed to 1 mole of the compound of formula (2a).

The reaction temperature is usually within a range of −80 to 180° C. and preferably within a range of −80 to 50° C. The reaction period of the reaction is usually within a range of 10 minutes to 30 hours.

The completion of the reaction can be confirmed by sampling a part of the reaction mixtures followed by performing analytical means such as thin-layer chromatography and high-performance liquid chromatography. When the reaction is completed, for example, the reaction mixtures are acidified with an acid, are mixed with water, and are extracted with an organic solvent, and the resulting organic layers are treated (for example, drying and concentration) to obtain the compound of formula (2b).

The compound of formula (5) is a known compound, or may be prepared from a known compound.

Reference Process 2

The compound of formula (3) can be prepared according to the below-mentioned process.

[wherein, $R^8$, Z and n are the same as defined above]

(Step 1)

The reaction is usually carried out in a solvent. Examples of the solvent to be used in the reaction include aromatic hydrocarbons such as benzene, toluene and xylene; ethers such as diethyl ether, diisopropylether, dioxane, tetrahydrofuran and dimethoxyethane; halogenated hydrocarbons such as dichloromethane, chloroform and 1,2-dichloroethane; amides such as dimethylformamide and dimethylacetamide; sulfones such as sulfolane; and mixed solvents thereof.

The amount used of carbon dioxide used in the reaction is usually within a range of 1 molar equivalent or more and preferably within a range of 3 to 10 molar equivalents as opposed to 1 mole of the compound of formula (7).

Examples of the base to be used in the reaction includes alkaline metal amides such as lithium diisopropylamide, sodium bis(trimethylsilyl)amide, lithium bis(trimethylsilyl) amide and potassium bis(trimethylsilyl)amide; organic bases such as dimethylaminopyridine, 1,8-diazabicyclo [5.4.0]-7-undecene and N,N-diisopropylethylamine; metal alkoxides such as potassium tert-butoxide; and alkali metal hydrides such as sodium hydride, and preferably organic lithium such as butyl lithium.

The amount used of the base used in the reaction is usually within a range of 2 to 10 molar equivalents and preferably within a range of 2 to 5 molar equivalents as opposed to 1 mole of the compound of formula (7).

The reaction temperature is usually within a range of −80 to 50° C. The reaction period of the reaction is usually within a range of 10 minutes to 30 hours.

The completion of the reaction can be confirmed by sampling a part of the reaction mixtures followed by performing analytical means such as thin-layer chromatography and high-performance liquid chromatography. When the reaction is completed, for example, the reaction mixtures are mixed with water, and are extracted with an organic solvent, and the resulting organic layers are treated (for example, drying and concentration) to obtain the compound of formula (6).

The compound of formula (7) is a known compound, or may be prepared from a known compound.

(Step 2)

The compound of formula (3) can be prepared by reacting the compound of formula (6) and the compound A.

Examples of the compound A include thionyl chloride, phosphorus tribromide and phosphorus triiodide.

The reaction is usually carried out in a solvent. Examples of the solvent to be used in the reaction include aromatic hydrocarbons such as benzene, toluene and xylene; ethers such as diethyl ether, diisopropylether, dioxane, tetrahydrofuran and dimethoxyethane; halogenated hydrocarbons such as dichloromethane, chloroform and 1,2-dichloroethane; amides such as dimethylformamide and dimethylacetamide; sulfones such as sulfolane; and mixed solvents thereof.

The amount used of the compound A used in the reaction is usually within a range of 2 molar equivalents or more and preferably within a range of 5 to 10 molar equivalents as opposed to 1 mole of the compound of formula (6).

The reaction temperature is usually within a range of −30 to 150° C. The reaction period of the reaction is usually within a range of 10 minutes to 30 hours.

The completion of the reaction can be confirmed by sampling a part of the reaction mixtures followed by concentrating the reaction mixtures under reduced pressure and performing analytical means such as nuclear magnetic resonance instrument on the resulting organic materials. When the reaction is completed, for example, the reaction mixtures are treated (for example, concentration under reduced pressure) to obtain the compound of formula (3).

Reference Process 3

The compound of formula (9g) can be prepared by reacting a compound of formula (10g) and a compound of formula (35).

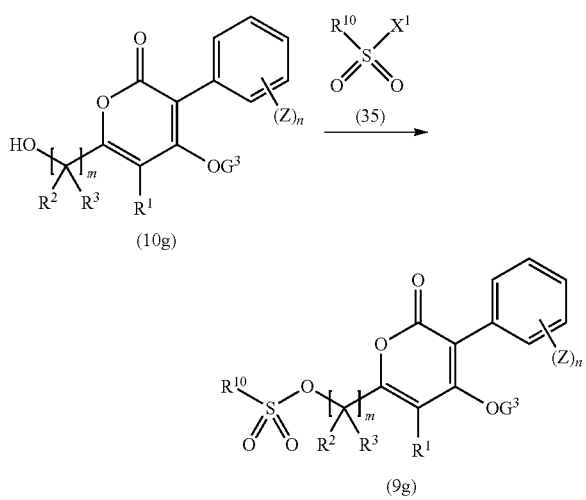

[wherein, $R^{10}$, $X^1$, $R^1$, $R^2$, $R^3$, n, m, $G^3$ and Z are the same as defined above]

The reaction is usually carried out in a solvent. Examples of the solvent to be used in the reaction include aromatic hydrocarbons such as benzene and toluene; ethers such as diethyl ether, diisopropylether, dioxane, tetrahydrofuran and dimethoxyethane; halogenated hydrocarbons such as dichloromethane, chloroform and 1,2-dichloroethane; amides such as dimethylformamide and dimethylacetamide; sulfoxides such as dimethyl sulfoxide; sulfones such as sulfolane; and mixed solvents thereof.

Examples of the compound of formula (35) to be used in the reaction include sulfonic halides such as methanesulfonyl chloride and p-toluenesulfonyl chloride; and sulfonic anhydrides such as methanesulfonic anhydride and trifluoromethanesulfonic anhydride. The amount used of the compound of formula (35) to be used in the reaction is usually within a range of 1 molar equivalent or more and preferably within a range of 1 to 3 molar equivalents as opposed to 1 mole of the compound of formula (10g).

The reaction is usually carried out in the presence of a base. Examples of the base to be used in the reaction includes organic bases such as triethylamine, tripropylamine, pyridine, dimethylaminopyridine, 1,8-diazabicyclo[5.4.0]-7-undecene; and inorganic bases such as sodium hydroxide, potassium hydroxide, calcium hydroxide, sodium carbonate, potassium carbonate, sodium hydrogen carbonate, calcium carbonate and sodium hydride. The amount used of the base is usually within a range of 0.5 to 10 molar equivalents and preferably within a range of 1 to 5 molar equivalents as opposed to 1 mole of the compound of formula (10g).

The reaction temperature is usually within a range of −30 to 180° C. and preferably within a range of −10 to 50° C. The reaction period of the reaction is usually within a range of 10 minutes to 30 hours.

The completion of the reaction can be confirmed by analyzing a part of the reaction mixtures by thin-layer chromatography and high-performance liquid chromatography and the like.

When the reaction is completed, for example, the reaction mixtures are mixed with water, and are extracted with an organic solvent, and the resulting organic layers are treated (for example, drying and concentration) to obtain the compound of formula (9g).

The compound of formula (35) is a known compound, or may be prepared from a known compound.

Reference Process 4

The compound of formula (10g) can be prepared by reacting a compound of formula (11g) in the presence of a metal.

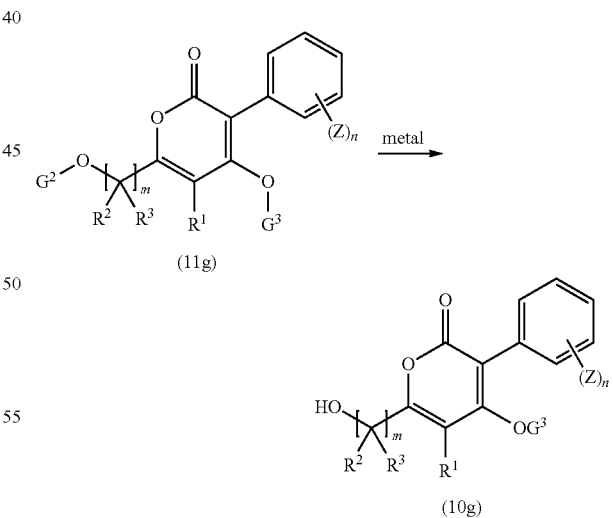

[wherein $G^2$ represents a benzyl group or a para-methoxybenzyl group and $R^1$, $R^2$, $R^3$, n, m, $G^3$ and Z are the same as defined above]

The reaction is usually carried out in a solvent. Examples of the solvent include aromatic hydrocarbons such as benzene and toluene; ethers such as diethyl ether, diisopropylether, dioxane, tetrahydrofuran and dimethoxyethane; alcohols such as methanol and ethanol; esters such as ethyl acetate; and mixed solvents thereof.

Examples of the metal to be used in the reaction include palladium and platinum. The amount used of the metal to be used in the reaction is usually within a range of 0.01 molar equivalents or more and preferably within a range of 0.01 to 0.5 molar equivalents as opposed to 1 mole of the compound of formula (23).

The reaction temperature is usually within a range of −30 to 180° C. and preferably within a range of −10 to 50° C. The reaction period of this reaction is usually within a range of 10 minutes to 30 hours.

The completion of the reaction can be confirmed by analyzing a part of the reaction mixtures on analytical means such as thin-layer chromatography and high-performance liquid chromatography. When the reaction is completed, for example, the reaction mixtures are filtered through Celite (registered trademark) and the resulting filtrates are treated (for example, concentration under reduced pressure) to obtain the compound of formula (10g).

Reference Process 5

The compound of formula (11g) can be prepared by reacting a compound of formula (12g) and a compound of formula: $G^3$-$X^1$ in the presence of a base.

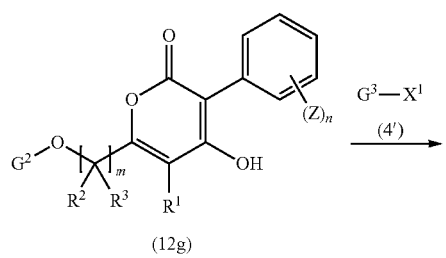

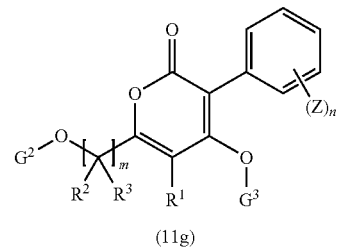

[wherein, $R^1$, $R^2$, $R^3$, n, m, $G^2$, $G^3$, $X^1$ and Z are the same as defined above]

The reaction is usually carried out in a solvent. Examples of the solvent include aromatic hydrocarbons such as benzene and toluene; ethers such as diethyl ether, diisopropylether, dioxane, tetrahydrofuran and dimethoxyethane; alcohols such as methanol and ethanol; esters such as ethyl acetate; and mixed solvents thereof.

Examples of the compound of formula: $G^3$-$X^1$ to be used in the reaction include carboxylic halides such as acetyl chloride, propionyl chloride, isobutyryl chloride, pivaloyl chloride, benzoyl chloride and cyclohexanecarboxylic acid chloride; carboxylic anhydrides such as acetic anhydride and trifluoroacetic anhydride; halides of carbonate ester such as methyl chloroformate, ethyl chloroformate and phenyl chloroformate; carbamic halides such as dimethylcarbamoyl chloride; sulfonic halides such as methanesulfonyl chloride and p-toluenesulfonyl chloride; sulfonic anhydrides such as methanesulfonic anhydride and trifluoromethanesulfonic anhydride; alkyl halogenoalkyl ethers such as chloromethyl methyl ether and ethyl chloromethyl ether.

The amount used of the compound of formula: $G^3$-$X^1$ to be used in the reaction is usually within a range of 1 molar equivalent or more and preferably within a range of 1 to 3 molar equivalents as opposed to 1 mole of the compound of formula (12g).

Examples of the base to be used in the reaction includes organic bases such as triethylamine, tripropylamine, pyridine, dimethylaminopyridine, 1,8-diazabicyclo[5.4.0]-7-undecene; and inorganic bases such as sodium hydroxide, potassium hydroxide, calcium hydroxide, sodium carbonate, potassium carbonate, sodium hydrogen carbonate, calcium carbonate and sodium hydride.

The amount used of the base is usually within a range of 0.5 to 10 molar equivalents and preferably within a range of 1 to 5 molar equivalents as opposed to 1 mole of the compound of formula (12g).

The reaction temperature is usually within a range of −30 to 180° C. and preferably within a range of −10 to 50° C. The reaction period of this reaction is usually within a range of 10 minutes to 30 hours.

The completion of the reaction can be confirmed by analyzing a part of the reaction mixtures on analytical means such as thin-layer chromatography and high-performance liquid chromatography. When the reaction is completed, for example, the reaction mixtures are mixed with water, and are extracted with an organic solvent, and the resulting organic layers are treated (for example, drying and concentration) to obtain the compound of formula (11g).

The compound of formula: $G^3$-$X^1$ is a known compound, or may be prepared from a known compound.

Reference Process 6

The compound of formula (12g) can be prepared by reacting a compound of formula (13g) and a compound of formula (3) in the presence of a base.

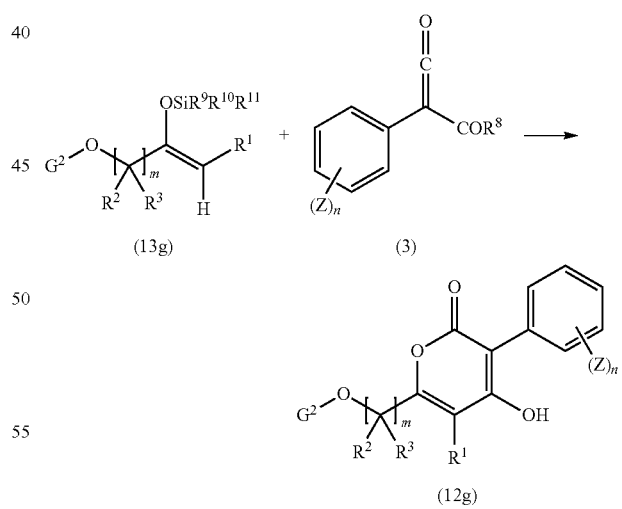

[wherein, $G^2$, $R^1$, $R^2$, $R^3$, $R^8$, X, n, m and Z are the same as defined above; and $R^9$, $R^{10}$ and $R^{11}$ represent independently of each other a methyl group, an ethyl group, a t-butyl group, a diisopropyl group or a phenyl group, and preferably a methyl group]

The reaction is usually carried out in a solvent. Examples of the solvent to be used in the reaction include aromatic hydrocarbons such as benzene, toluene and xylene; ethers such as diethyl ether, diisopropylether, dioxane, tetrahydrofuran and dimethoxyethane; halogenated hydrocarbons such as dichloromethane, chloroform and 1,2-dichloroethane; amides such as dimethylformamide and dimethylacetamide; sulfones such as sulfolane; and mixed solvents thereof, and preferably aromatic hydrocarbons such as xylene.

The amount used of the compound of formula (3) to be used in the reaction is usually within a range of 1 to 3 molar equivalents as opposed to 1 mole of the compound of formula (13g).

The reaction temperature is usually within a range of −60 to 200° C. The reaction period of this reaction is usually within a range of 10 minutes to 30 hours.

The completion of the reaction can be confirmed by sampling a part of the reaction mixtures followed by performing analytical means such as thin-layer chromatography and high-performance liquid chromatography. When the reaction is completed, for example, the reaction mixtures are acidified with an acid, are mixed with water, and are extracted with an organic solvent, and the resulting organic layers are treated (for example, drying and concentration) to obtain the compound of formula (12g).

Reference Process 7

The compound of formula (13g) can be prepared by reacting a compound of formula (14g) and a compound of formula (5) in the presence of a base.

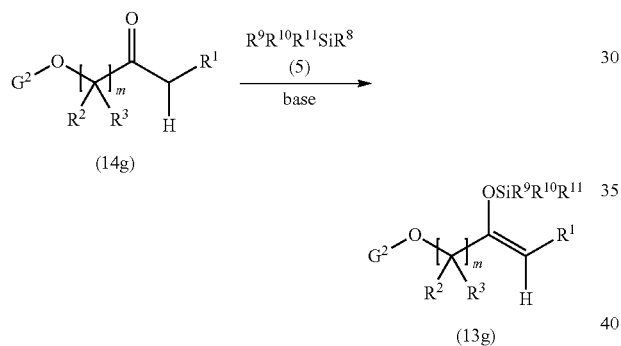

[wherein $R^1$, $R^2$, $R^3$, $R^8$, $R^9$, $R^{10}$, $R^{11}$, X, n, $G^2$ and m are the same as defined above]

The reaction is usually carried out in a solvent. Examples of the solvent to be used in the reaction include aromatic hydrocarbons such as benzene, toluene and xylene; ethers such as diethyl ether, diisopropylether, dioxane, tetrahydrofuran and dimethoxyethane; halogenated hydrocarbons such as dichloromethane, chloroform and 1,2-dichloroethane; amides such as dimethylformamide and dimethylacetamide; sulfones such as sulfolane; and mixed solvents thereof.

The amount used of the compound of formula (5) to be used in the reaction is usually within a range of 1 molar equivalent or more and preferably within a range of 1 to 3 molar equivalents as opposed to 1 mole of the compound of formula (14g).

Examples of the base to be used in the reaction includes alkaline metal amides such as lithium diisopropylamide, sodium bis(trimethylsilyl)amide, lithium bis(trimethylsilyl)amide and potassium bis(trimethylsilyl)amide; organic bases such as triethylamine, tripropylamine, pyridine, dimethylaminopyridine, 1,8-diazabicyclo[5.4.0]-7-undecene and N,N-diisopropylethylamine; metal alkoxides such as potassium tert-butoxide; and alkali metal hydrides such as sodium hydride, and preferably alkaline metal amides such as lithium diisopropylamide.

The amount used of the base to be used in the reaction is usually within a range of to 1 to 10 molar equivalents and preferably within a range of 1 to 2 molar equivalents as opposed to 1 mole of the compound of formula (14g).

The reaction temperature is usually within a range of −80 to 180° C., and preferably within a range of −80 to 50° C. The reaction period of this reaction is usually within a range of 10 minutes to 30 hours.

The completion of the reaction can be confirmed by sampling a part of the reaction mixtures followed by performing analytical means such as thin-layer chromatography and high-performance liquid chromatography. When the reaction is completed, for example, the reaction mixtures are mixed with water, and are extracted with an organic solvent, and the resulting organic layers are treated (for example, drying and concentration) to obtain the compound of formula (13g).

The compound of formula (5) is a known compound, or may be prepared from a known compound.

Some examples of the present compounds that can be prepared according to the above-mentioned processes are shown below. Hereinafter, the compound of formula (a-b) means the present compound (a-b).

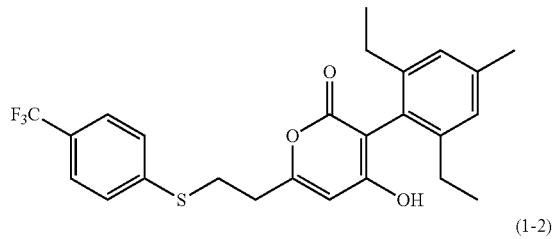
(1-1)

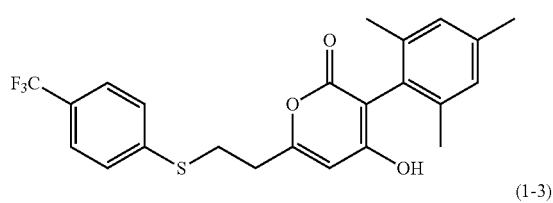
(1-2)

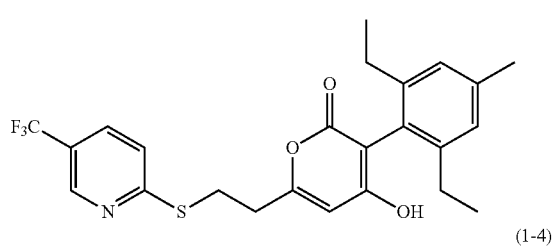
(1-3)

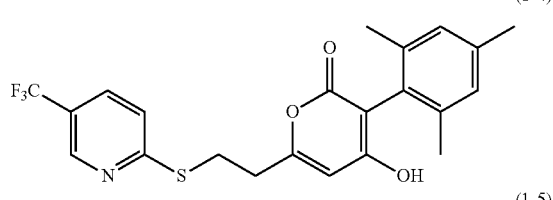
(1-4)

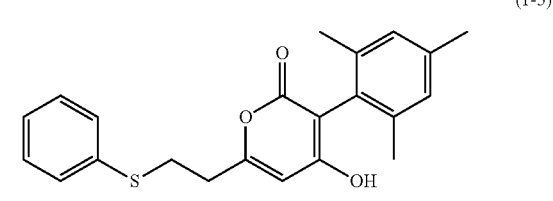
(1-5)

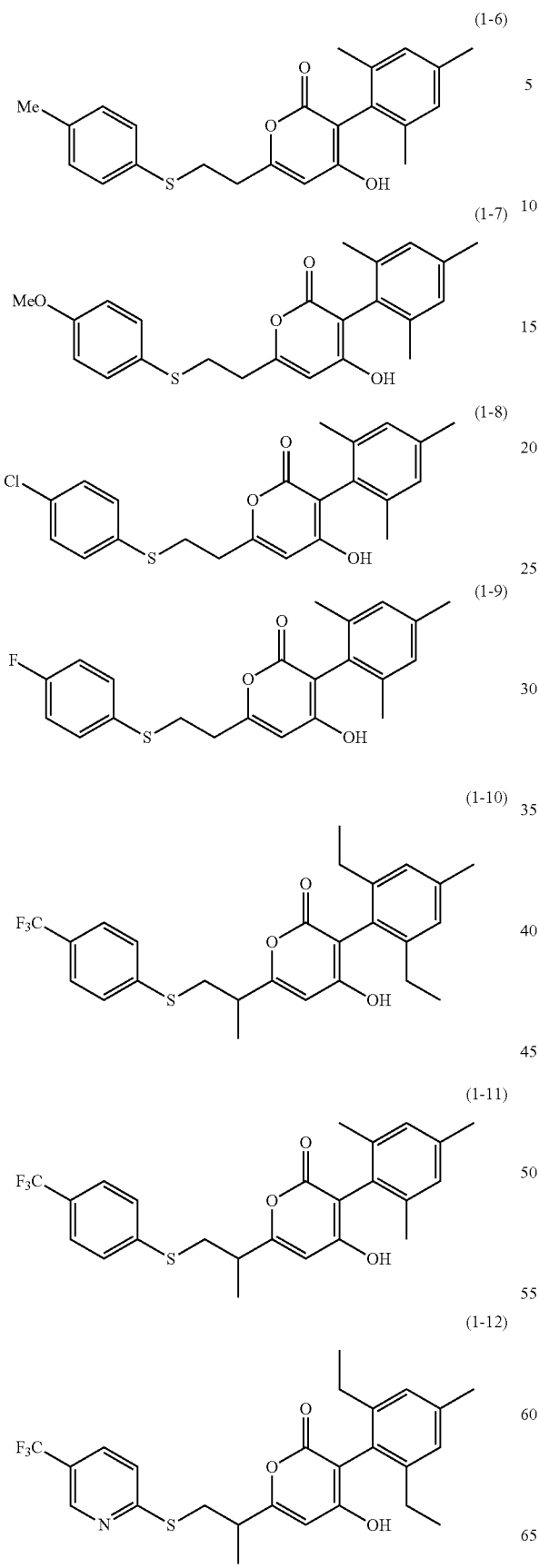
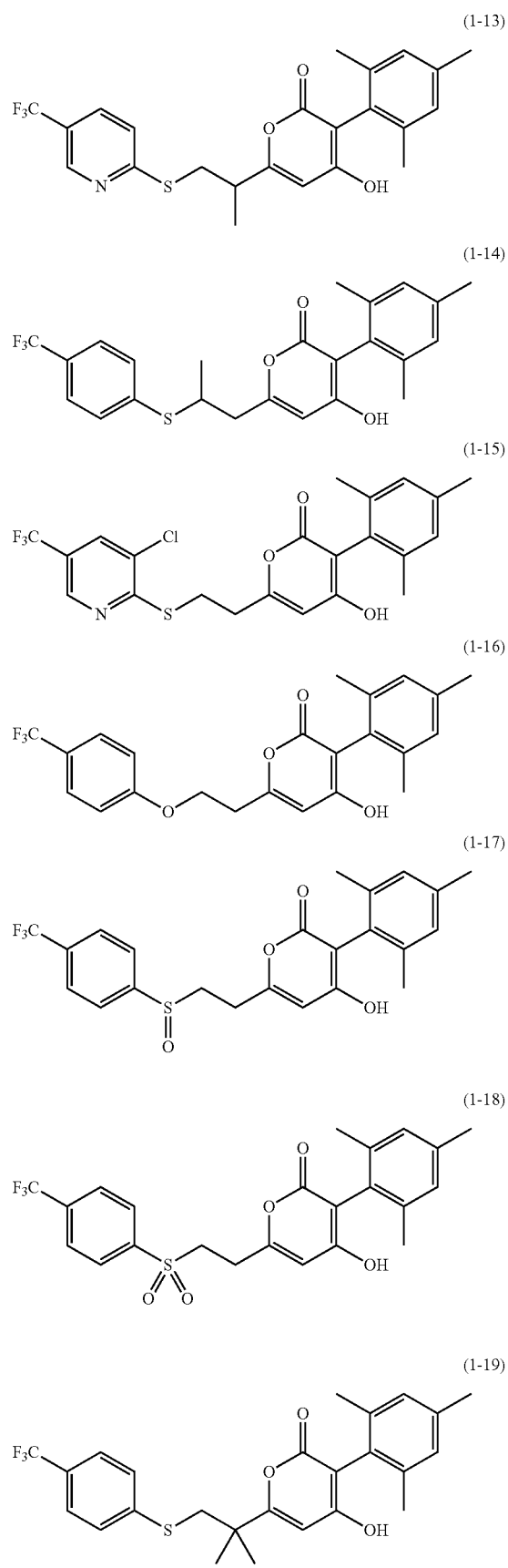

-continued
(1-20)
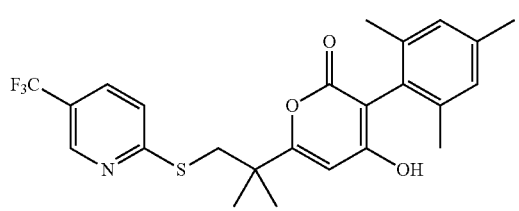
(1-21)
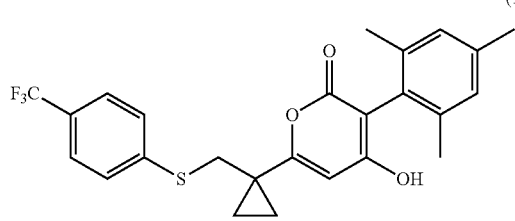
(1-22)
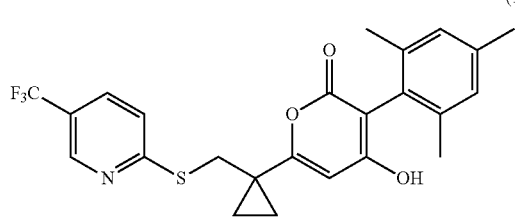
(1-23)
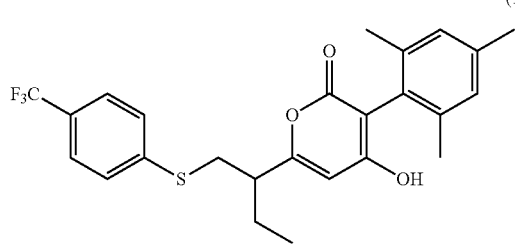
(1-24)
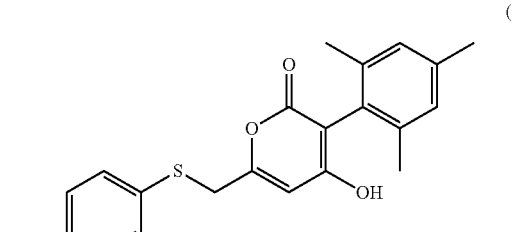
(1-25)
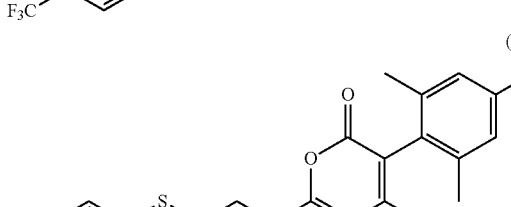
(1-26)
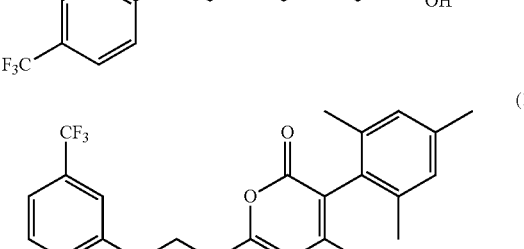
-continued
(1-27)
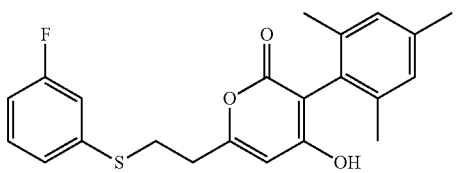
(1-28)
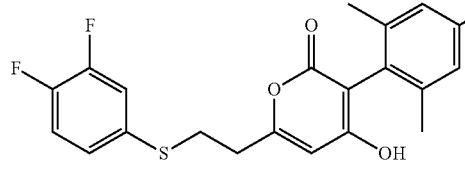
(1-29)
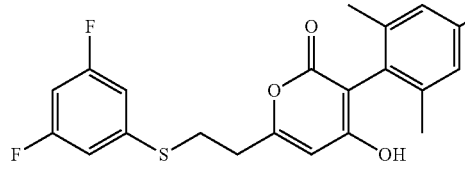
(1-30)
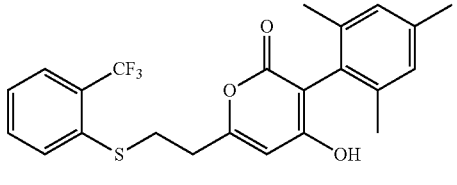
(1-31)
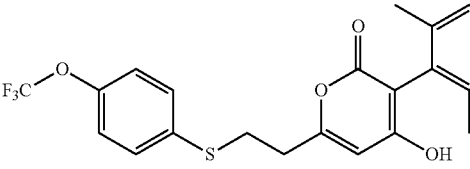
(1-32)
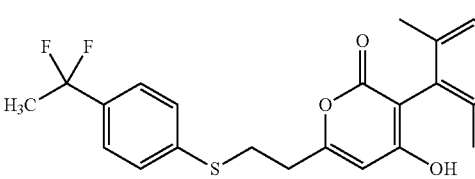
(1-33)
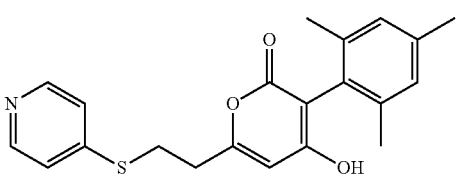
(1-34)
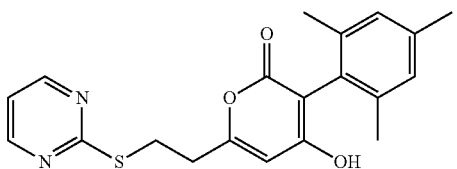
(1-35)
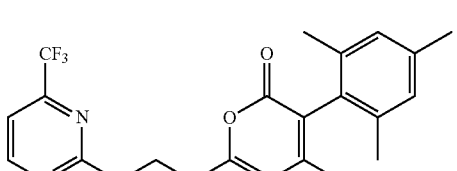

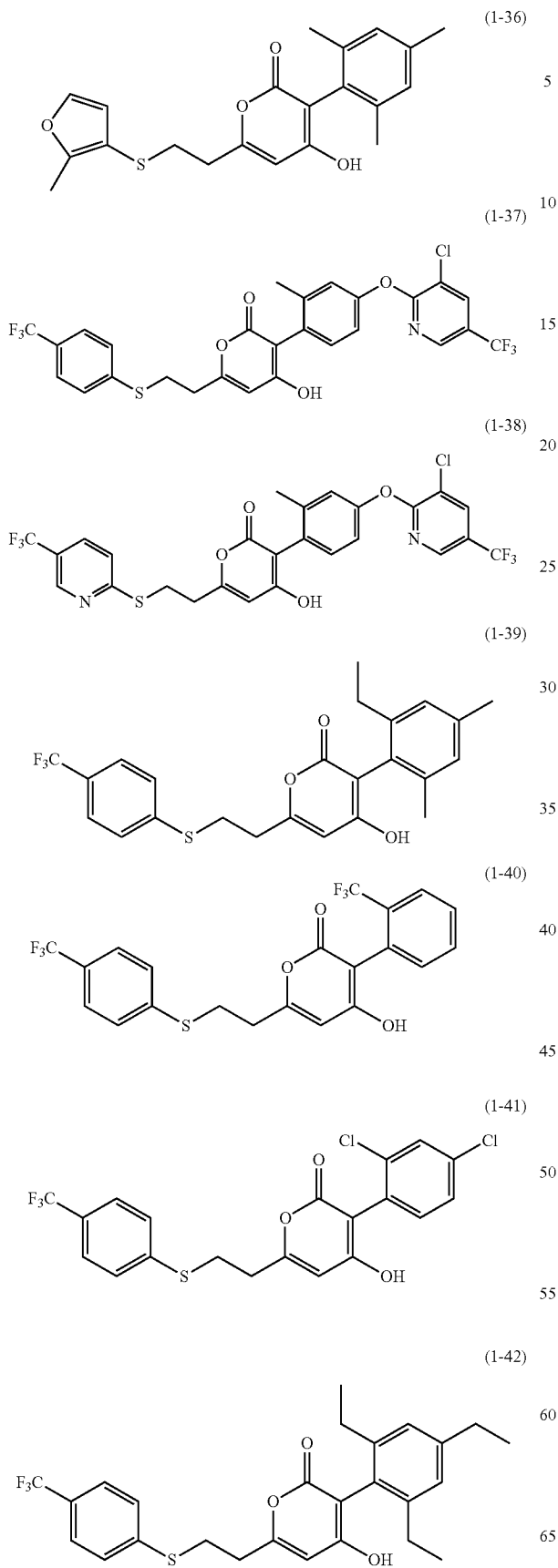

-continued
(1-49)
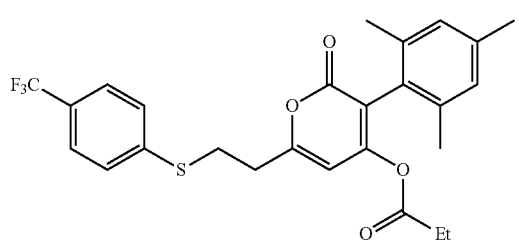
(1-50)
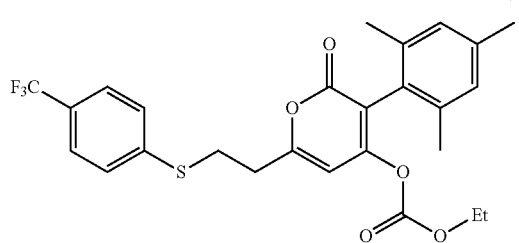
(1-51)
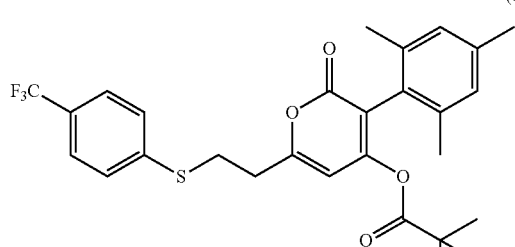
(1-52)
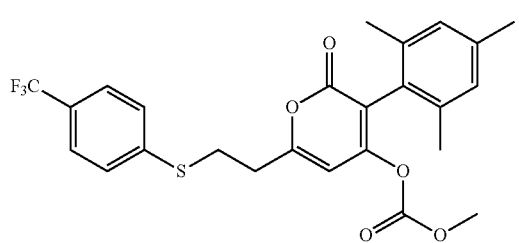
(1-53)
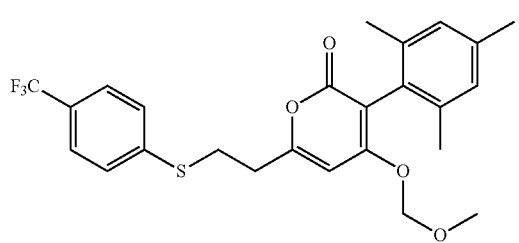
(1-54)
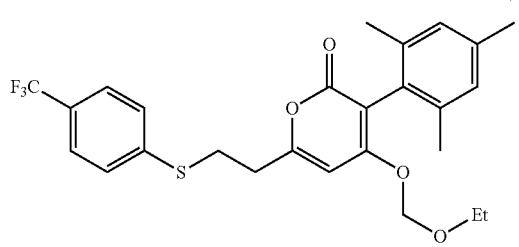
-continued
(1-55)
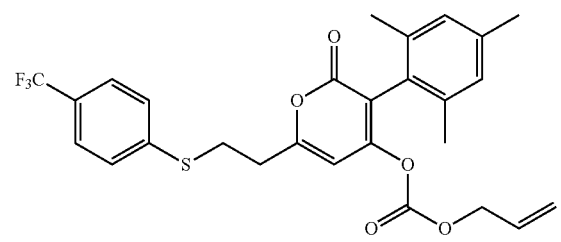
(1-56)
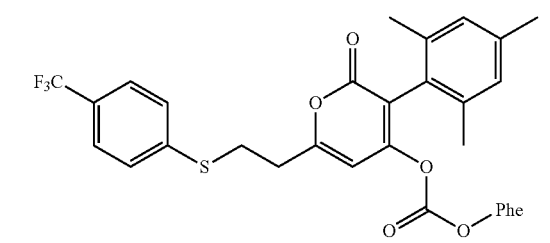
(1-57)
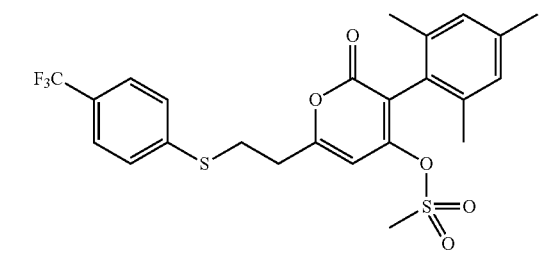
(1-58)
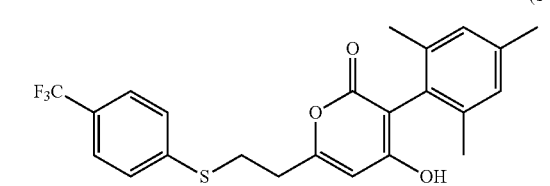
(1-59)
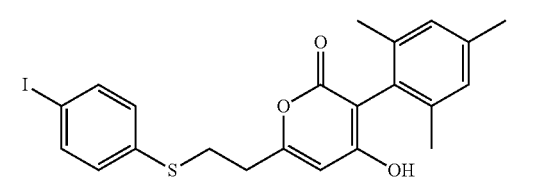
(1-60)
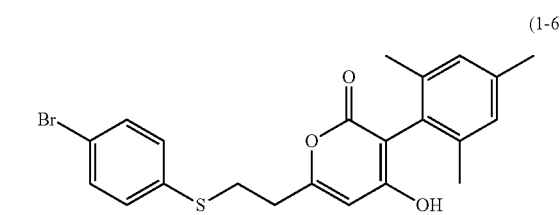
(1-61)
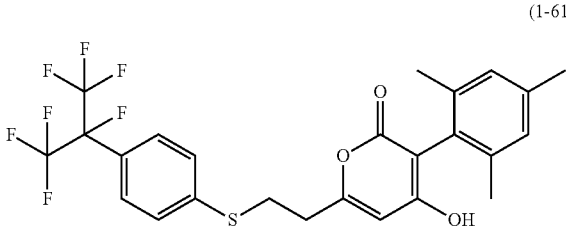

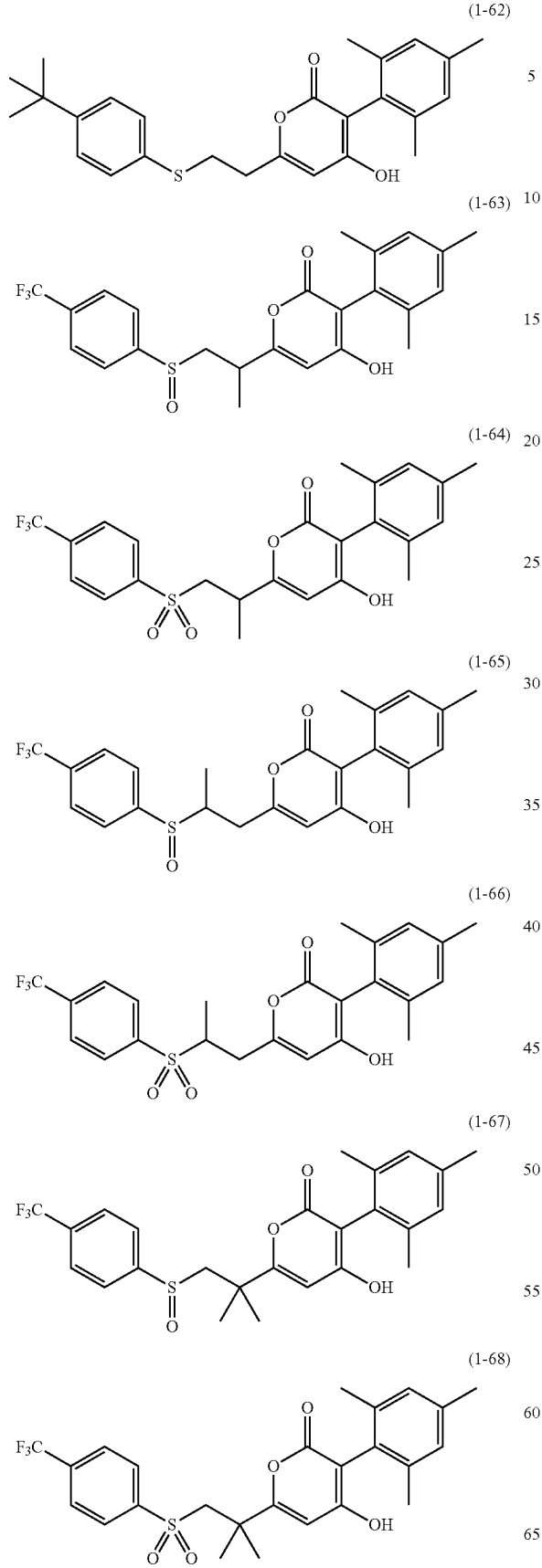
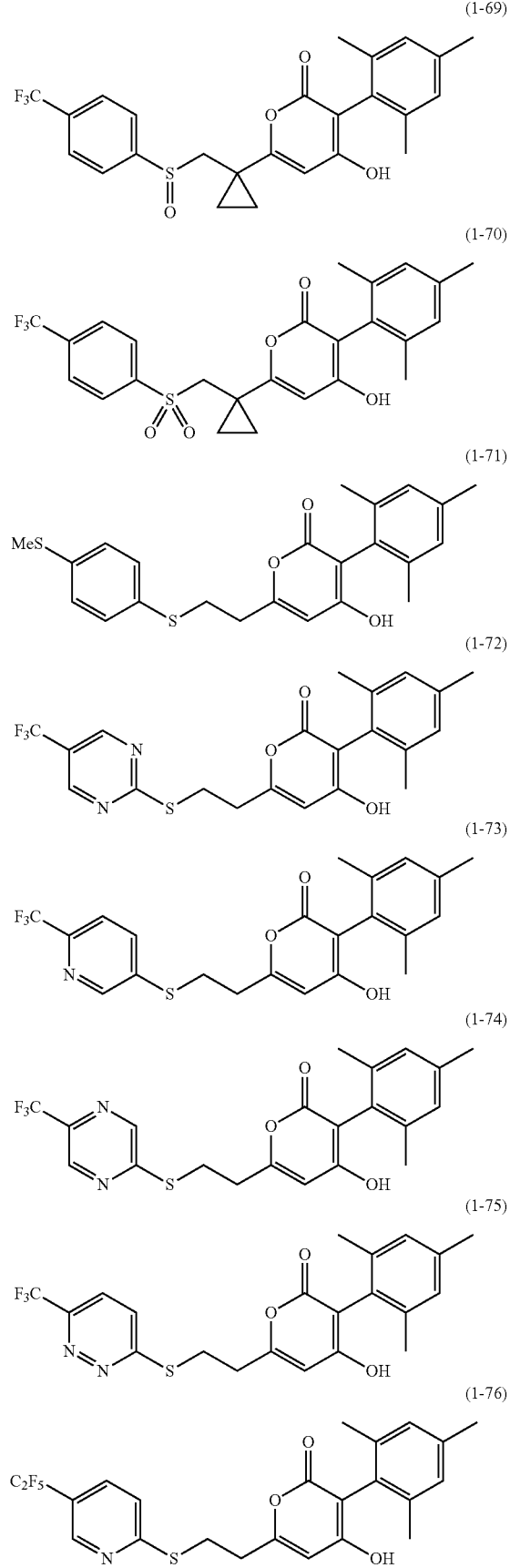

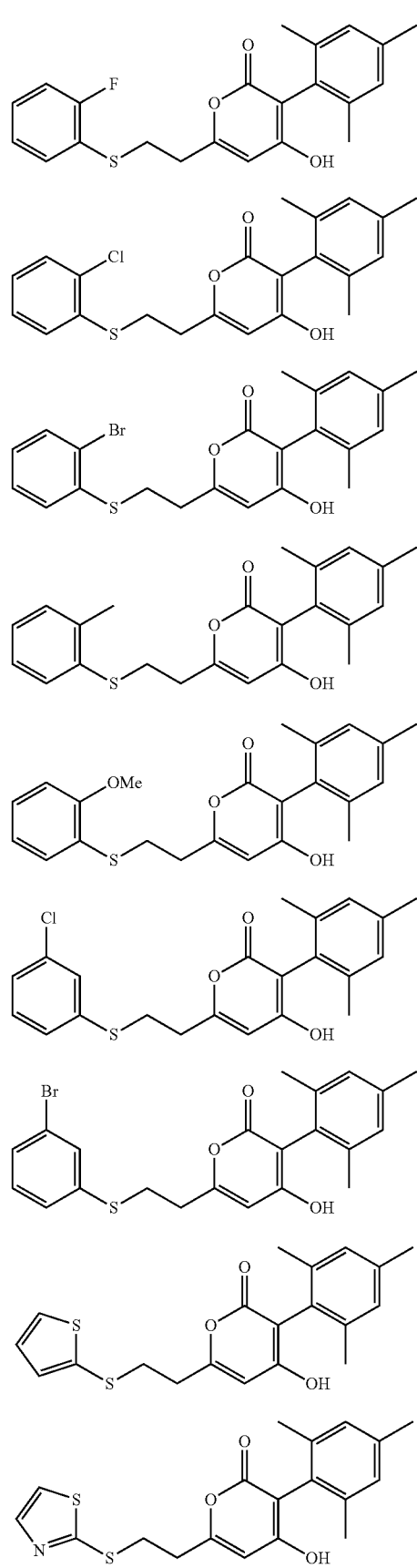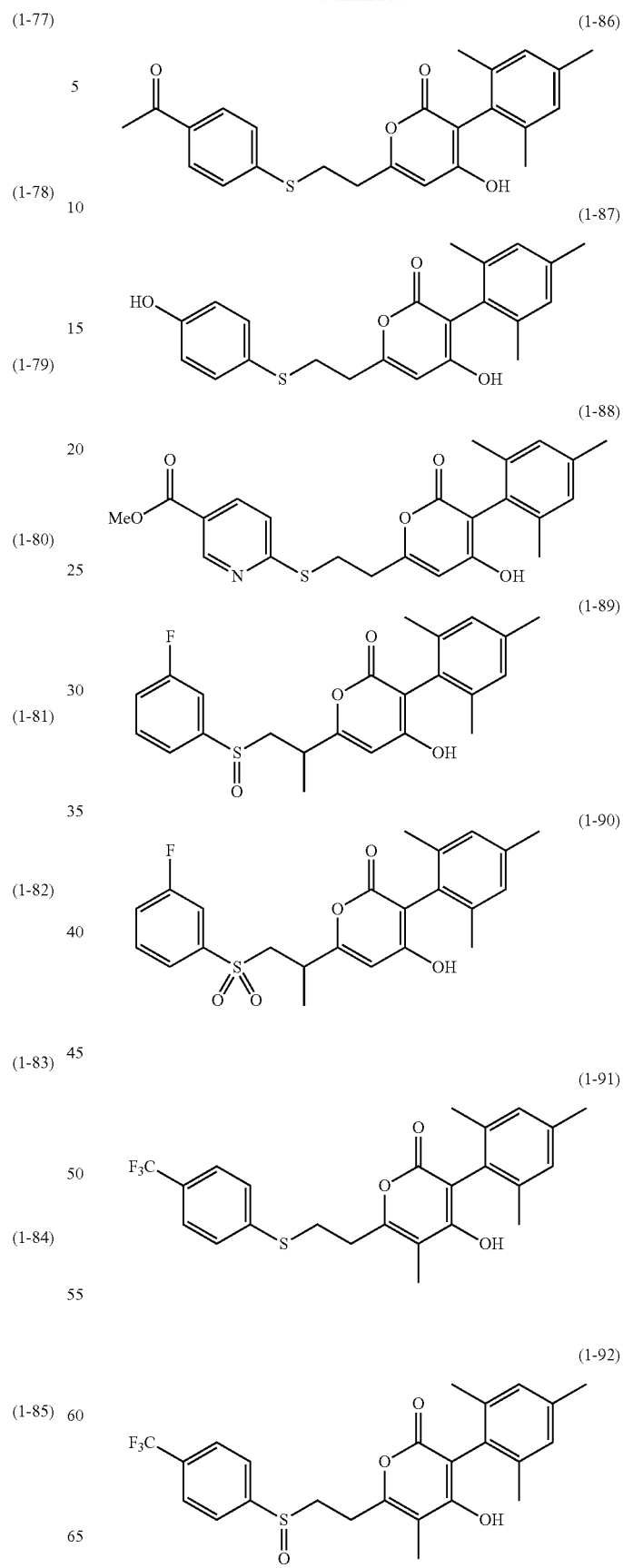

(1-93)
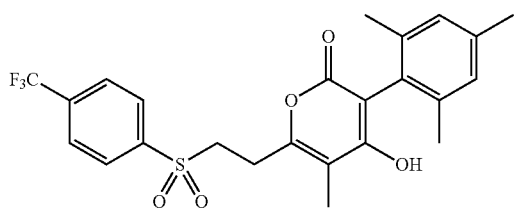
(1-94)
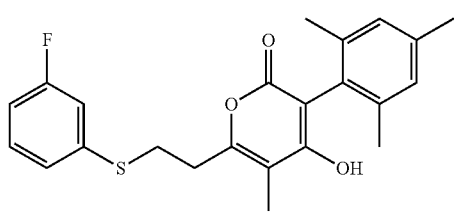
(1-95)
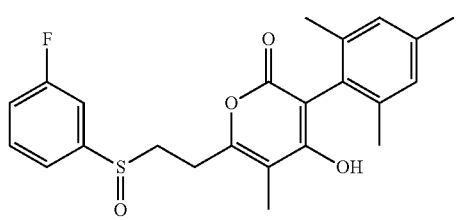
(1-96)
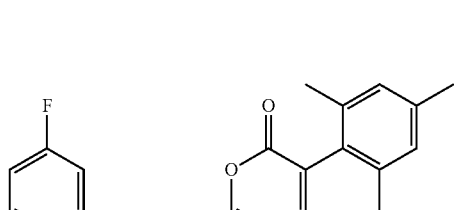
(1-97)
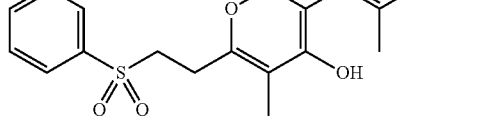
(1-98)
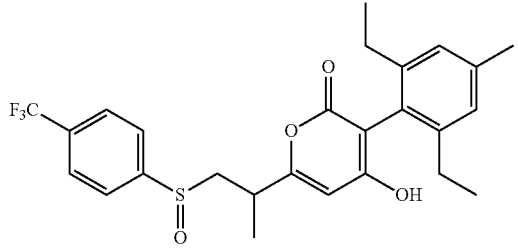
(1-99)
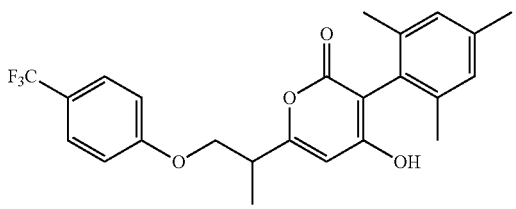
(1-100)
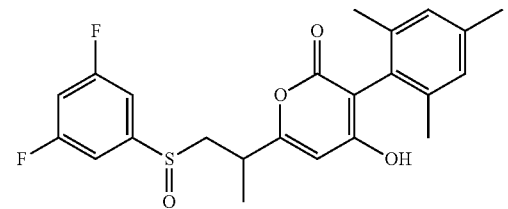
(1-101)
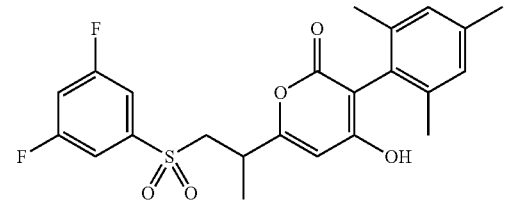
(1-102)
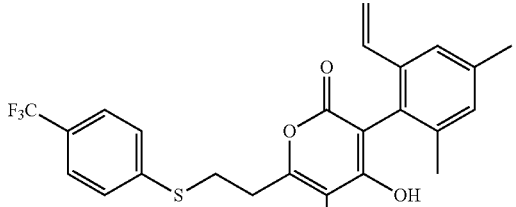
(1-103)
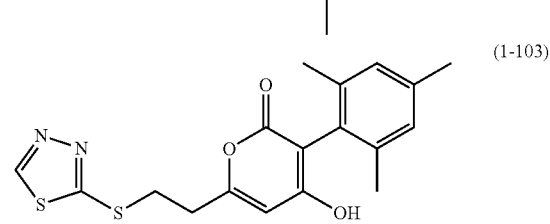
(1-104)
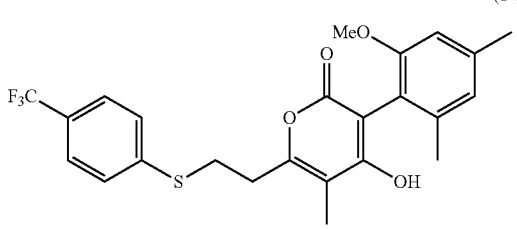
(1-105)
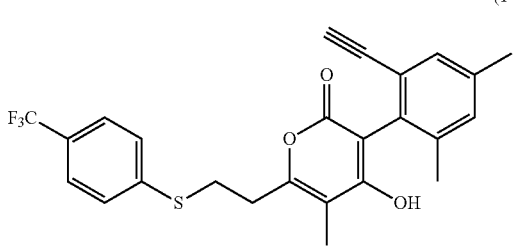

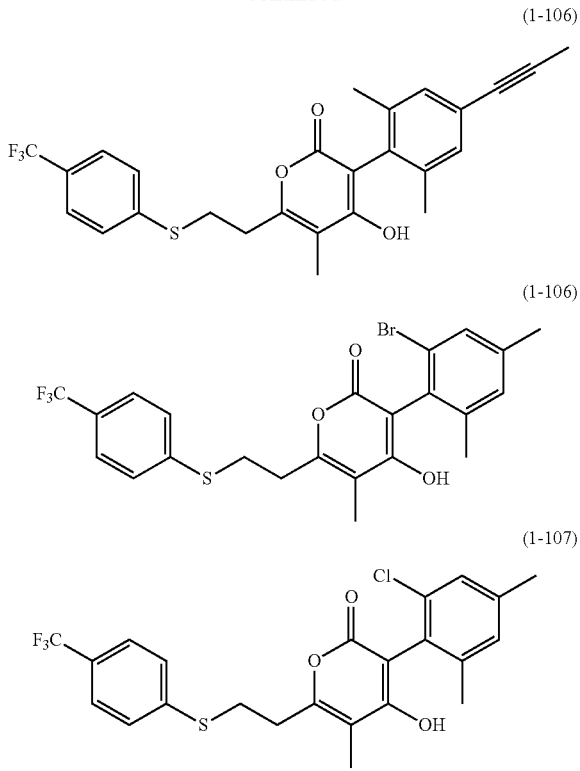

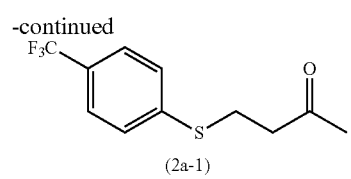

EXAMPLES

The present invention is described below in more detail with Preparation Examples, Formulation Examples and Test Examples, but the present invention should not be construed to be limited thereto.

The "room temperature" (hereinafter sometimes abbreviated to as "RT") described in Preparation Example means usually 10 to 30° C. $^1$H NMR means a proton nuclear magnetic resonance spectrum and Tetramethyl silane is used as an internal standard and chemical shift (δ) is expressed in ppm.

The following abbreviations are sometimes used in Preparation Example.

CDCl$_3$: Deuterated chloroform, s: singlet, d: doublet, t: triplet, q: quartet, m: multiplet, J: coupling constant, Me: methyl group, TMS: trimethylsilyl group; Phe: phenyl group, DIPEA: diisopropylethylamine, petether: petroleum ether.

Preparation Example 1-1: Preparation of the Compound of Formula (1-1)

<Preparation of a Compound of Formula 2a-1>

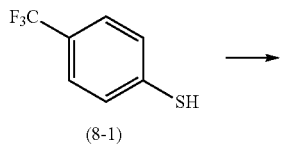

At RT, a compound of formula (8-1) 1.5 g and tetrahydrofuran 8 ml were mixed and then stirred. The resulting mixtures were cooled to 0° C., and thereto were then added 3-butene-2-one 1 ml and triethylamine 0.1 g drop wise. The resulting mixtures were stirred under ice-cooling for 3 hours. To the resulting reaction mixtures were then added water. The resulting mixtures were extracted with tert-butyl methyl ether. The organic layer was washed with water and dried over anhydrous Na$_2$SO$_4$ and concentrated under reduced pressure to afford the compound of formula (2a-1) 1.9 g.

$^1$H NMR (CDCl$_3$)

δ ppm: 7.53 (2H, d), 7.36 (2H, d), 3.20 (2H, t), 2.81 (2H, t), 2.18 (3H, s)

<Preparation of a Compound of Formula 6-1>

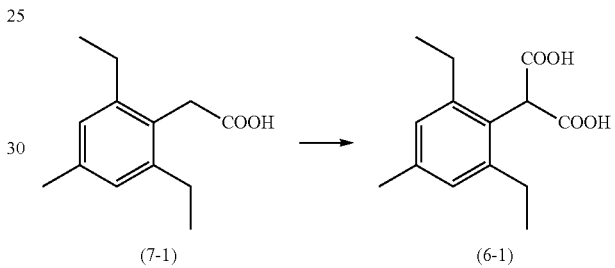

Under nitrogen atmosphere, at RT, a compound of formula (7-1) 5.0 g was dissolved in tetrahydrofuran 80 ml. The resulting solutions were cooled to −78° C. and thereto was added n-butyl lithium (1.63 M hexane solution) 36.6 ml under nitrogen atmosphere. The reaction solutions were then stirred at −30° C. under nitrogen atmosphere for about 1 hour and cooled to −78° C. again. Thereto was added dry ice 16 g under nitrogen atmosphere. The resulting solutions were raised to 0° C. under ice-cooling and stirred for about 2 hours. The resulting reaction solutions were then added to 2N aqueous hydrochloric acid solution 80 ml under ice-cooling. The organic layer was extracted with chloroform and washed with saturated saline and dried over anhydrous Mg$_2$SO$_4$. The resulting organic layer was concentrated under reduced pressure and filtered to give the residue. To the resulting residue was added hexane to precipitate some solids. The precipitated solids were washed with hexane and concentrated under reduced pressure to afford the compound of formula (6-1) 5 g.

$^1$H NMR (d-DMSO)

δ ppm: 6.87 (2H, s), 4.85 (1H, s), 2.60-2.55 (4H, m), 2.22 (3H, s), 1.10-1.07 (6H, m)

<Preparation of a Compound of Formula 2c-1>

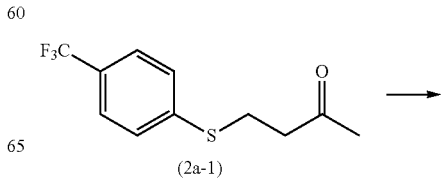

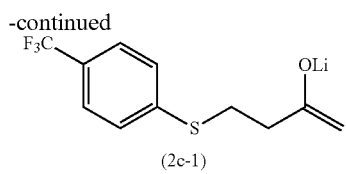

(2c-1)

Under nitrogen atmosphere, diisopropyl amine 0.3 ml was diluted with tetrahydrofuran 15 ml and the resulting solutions were cooled to −78° C. and thereto was added n-butyl lithium (1.63 M hexane solution) 1.3 ml drop wise. The reaction solutions were then stirred at 0° C. under nitrogen atmosphere for about 10 minutes and cooled to −78° C. again. Thereto was added a solution of the compound of formula <2a-1> 500 mg in tetrahydrofuran about 5 ml slowly drop wise and the resulting mixtures were stirred at −78° C. for 30 minutes to afford a solution of the compound of formula (2c-1) in tetrahydrofuran.

<Preparation of a Compound of Formula 1-1>

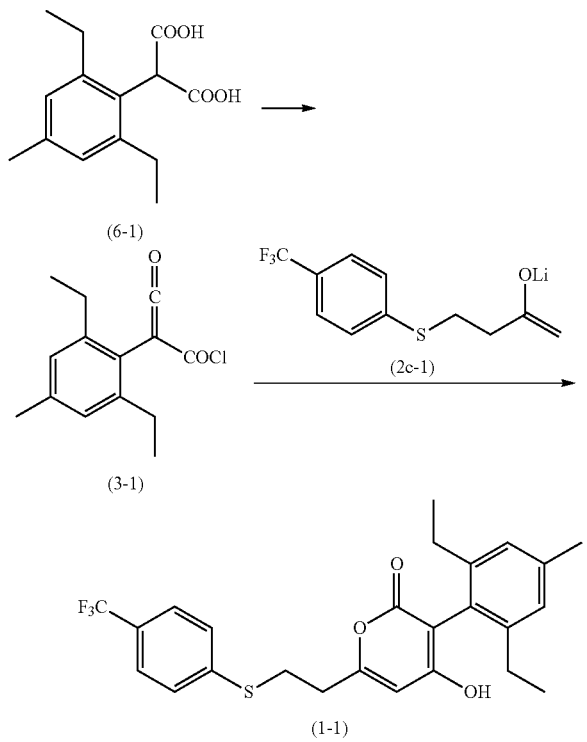

At RT, a compound of formula (6-1) 500 mg was dissolved in toluene 10 ml, and to the resulting solutions was added thionyl chloride 0.44 ml and the resulting mixtures were heated under reflux for about 1 hour. The resulting reaction solutions were then concentrated under reduced pressure to afford the crude compound of formula (3-1). Further, to the resulting crude compound of formula (3-1) was added xylene 10 ml and the resulting mixtures were cooled to −78° C. and thereto was then added a solution of the compound of formula (2c-1) in tetrahydrofuran slowly drop wise. The resulting reaction solutions were then raised to RT slowly and further heated under reflux at about 150° C. for 5 hours. The resulting reactions solutions were then concentrated under reduced pressure and the solvents were evaporated. The resulting oily residues were purified by column chromatography using (SiO$_2$) to afford the compound of formula (1-1) 86 mg.

$^1$H NMR (CDCl$_3$)

δ ppm: 7.55 (2H, d), 7.42 (2H, d), 7.01 (2H, s), 6.01 (1H, s), 3.33 (2H, t), 2.84 (2H, t), 2.49-2.25 (7H, m), 1.12-1.08 (6H, m)

Preparation Example 1-2: Preparation of a Compound of Formula (1-10)

<Preparation of a Compound of Formula 2a-10>

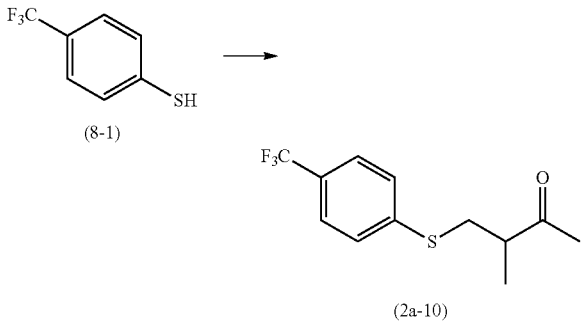

At RT, a compound of formula (8-1) 2 g and tetrahydrofuran 10 ml were mixed and then stirred. The resulting mixtures were cooled to 0° C. and thereto were then added 3-methyl-3-butene-2-one 1.5 ml and triethylamine 0.1 g drop wise. The resulting mixtures were stirred at RT for 3 hours. To the resulting mixtures were then added water. The resulting mixtures were extracted with tert-butyl methyl ether. The organic layer was washed with water and dried over anhydrous Na$_2$SO$_4$ and concentrated under reduced pressure, and purified by column chromatography using (SiO$_2$) to afford the compound of formula (2a-10) 1.8 g.

$^1$H NMR (CDCl$_3$)

δ ppm: 7.51 (2H, d), 7.36 (2H, d), 3.32 (1H, dd), 2.93 (1H, dd), 2.82 (1H, q), 2.19 (3H, s), 1.26 (3H, d)

<Preparation of a Compound of Formula 2b-10>

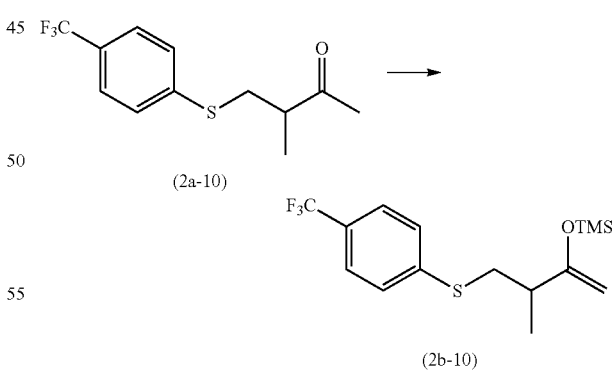

Under nitrogen atmosphere, at RT, diisopropyl amine 0.7 ml was dissolved in tetrahydrofuran 8 ml. The resulting solutions were cooled to 0° C. and thereto was added n-butyl lithium (1.63 M hexane solution) 3.0 ml under nitrogen atmosphere drop wise. The resulting solutions were cooled to −78° C. under nitrogen atmosphere and thereto was added a mixed solution of trimethylsilyl chloride 0.52 ml and tetrahydrofuran 3 ml, followed by a solution of a compound of formula (2a-10) 1.3 g dissolved in tetrahydrofuran 3 ml slowly, and the resulting mixtures were stirred for about 2 hours. The resulting reaction solutions were then raised to RT and the reaction solvent was evaporated by concentrating under reduced pressure to afford crude compound of formula (2b-10) 2.4 g. The resulting crude product was purified by column chromatography using (SiO$_2$) to afford to the compound of formula (2b-10) 1.0 g.

$^1$H NMR (CDCl$_3$)

δ ppm: 7.50 (2H, d), 7.37 (2H, d), 4.10 (1H, s), 4.07 (1H, s), 3.23 (1H, dd), 2.79 (1H, dd), 2.39 (1H, q), 1.17 (3H, d), 0.23 (9H, s)

<Preparation of a Compound of Formula 1-10>

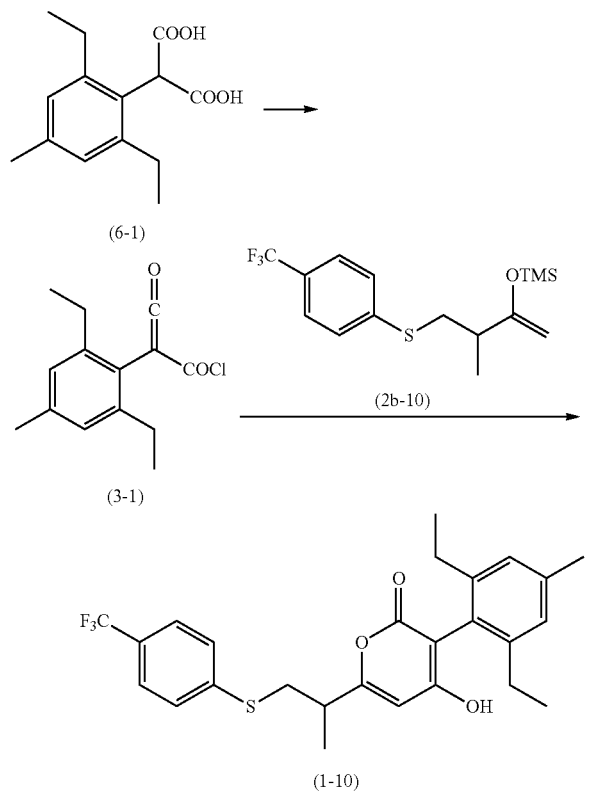

At RT, a compound of formula (6-1) 500 mg was dissolved in toluene 10 ml and to the resulting solutions was added thionyl chloride 0.44 ml. The resulting mixtures were heated under reflux for about 1 hour. The resulting reaction solutions were then concentrated under reduced pressure to afford crude compound of formula (3-1). Further, to the resulting crude compound of formula (3-1) was added xylene 5 ml at RT, followed by a solution of a compound of formula (2b-10) 630 mg in xylene 5 ml slowly drop wise. The resulting reaction solutions were then heated to about 150° C. and heated under reflux for 3 hours. The resulting reaction solutions were then concentrated under reduced pressure to evaporate the reaction solvent. The resulting oily materials were purified by column chromatography using (SiO$_2$) to afford the compound of formula (1-1) 340 mg.

$^1$H NMR (CDCl$_3$)

δ ppm: 7.54 (2H, d), 7.41 (2H, d), 7.02 (2H, s), 6.01 (1H, s), 3.43 (1H, dd), 3.15 (1H, dd), 2.91 (1H, q), 2.47-2.30 (7H, m), 1.43 (3H, d), 1.10 (6H, td)

Preparation Example 1-3: Preparation of a Compound of Formula (1-11)

<Preparation of a Compound of Formula 6-2>

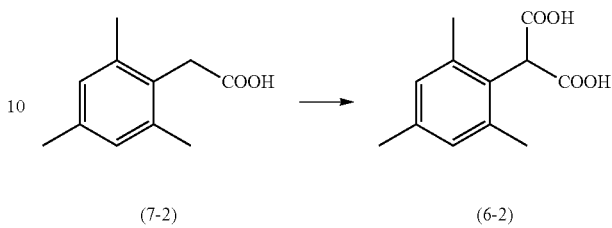

Under nitrogen atmosphere, at RT, a compound of formula (7-2) 5.0 g was dissolved in tetrahydrofuran 80 ml. The resulting solutions were cooled to −78° C. and thereto was added n-butyl lithium (1.63 M hexane solution) 40.3 ml drop wise under nitrogen atmosphere. The reaction solutions were then stirred at −30° C. under nitrogen atmosphere for about 1 hour and cooled to −78° C. again, and thereto was added dry ice 16 g under nitrogen atmosphere. The resulting solutions were raised to 0° C. under ice-cooling and stirred for about 2 hours. The resulting reaction solutions were then added to 2N aqueous hydrochloric acid solution under ice-cooling, and the organic layer were extracted with chloroform and washed with saturated saline and dried over anhydrous Mg$_2$SO$_4$. The resulting organic layer was concentrated under reduced pressure and then filtered. To the resulting residue was added hexane to precipitate some solids. The precipitated solids were washed with hexane and filtered under reduced pressure to afford the compound of formula (6-2) 5 g.

$^1$H NMR (d-DMSO)

δ ppm: 6.88 (2H, s), 3.69 (1H, s), 2.29 (6H, s), 2.26 (3H, s)

<Preparation of a Compound of Formula 1-11>

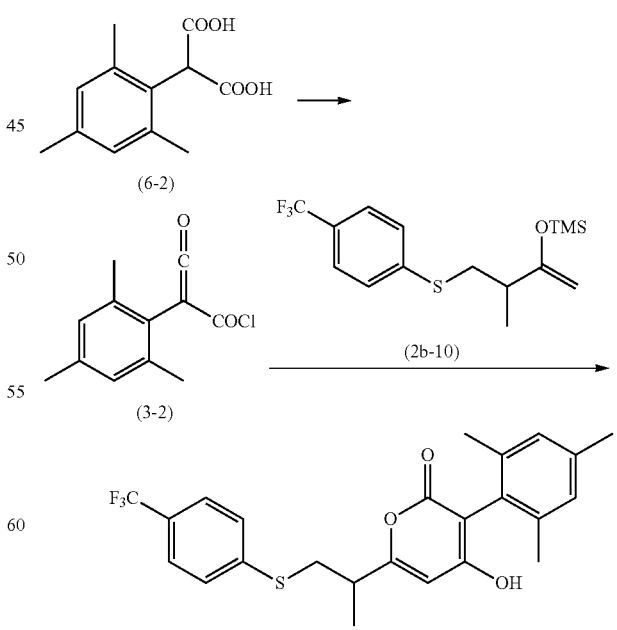

At RT, a compound of formula (6-2) 250 mg was dissolved in toluene 5 ml and to the resulting solutions was added thionyl chloride 0.25 ml and the resulting mixtures were heated under reflux for about 1 hour. The resulting reaction solutions were then concentrated under reduced pressure to afford crude compound of formula (3-2). Further, to the resulting crude compound of formula (3-2) was added xylene 3 ml at RT, followed by a solution of a compound of formula (2b-10) 370 mg in xylene 3 ml slowly drop wise. The resulting reaction solutions were then heated to 150° C. and heated under reflux for 3 hours. The resulting reaction solutions were then concentrated under reduced pressure to evaporate the reactions solvent. The resulting oily residues were purified by column chromatography using ($SiO_2$) to afford the compound of formula (1-1) 130 mg.

$^1$H NMR (CDCl$_3$)

δ ppm: 7.53 (2H, d), 7.41 (2H, d), 6.98 (2H, s), 6.01 (1H, s), 3.40 (1H, dd), 3.16 (1H, dd), 2.91 (1H, q), 2.30-2.07 (9H, m), 1.43 (3H, d)

A similar reaction to process 1-2 using 2-mercapto-5-trifluoromethylpyridine instead of the compound of formula (8-1) affords the following present compound.

<The Compound of the Formula 1-12>

$^1$H NMR (CDCl$_3$)

δ ppm: 8.66 (1H, s), 7.66 (1H, d), 7.26 (1H, d), 7.02 (2H, s), 6.01 (1H, s), 3.43 (1H, dd), 3.15 (1H, dd), 2.91 (1H, q), 2.47-2.30 (7H, m), 1.43 (3H, d), 1.10 (6H, td)

Preparation Example 1-4: Preparation of a Compound of Formula (1-5)

<Preparation of a Compound of Formula 2a-5>

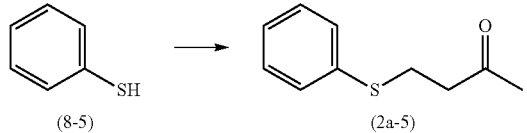

(8-5) → (2a-5)

To a solution of thiophenol (5 g, 45.45 mmol) in dry THF (20 Vols) was added TEA (12.22 mL, 90.50 mmol) followed by methyl vinyl ketone (4.46 mL, 54.54 mmol) at 0° C. and the resulting mixtures were stirred at RT for 2 hours. After completion, the solvent was poured into water (50 mL) and extracted with EtOAc (2×50 mL). The combined extracts were washed with water (50 mL), brine (50 mL), dried over anhydrous Na$_2$SO$_4$, filtered and evaporated and the obtained crude was purified by column chromatography using (SiO$_2$) by eluting with EtOAc:petether (2:98) to afford 4-(phenylthio)butan-2-one (2a-5) (6 g, 73.3%) as off white solid.

$^1$H NMR (d-DMSO)

δ ppm: 7.18-7.35 (m, 5H), 3.13 (t, 2H), 2.76 (t, 2H), 2.15 (S, 3H)

<Preparation of a Compound of Formula 2c-5>

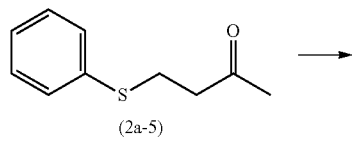

(2a-5)

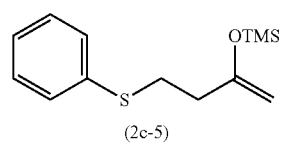

(2c-5)

To a solution of LDA (14.80 mL, 26.66 mmol) in dry THF (50 mL) at −78° C. was added a solution of 4-(phenylthio)butan-2-one (2a-5) (4 g, 11.11 mmol) in dry THF (10 mL) drop wise, and the resulting mixtures were stirred for 10 minutes, and thereto was then added quickly TMS-Cl (4.08 mL, 33.32 mmol) at −78° C. The reaction mixtures were slowly brought to room temperature and were stirred for 2.5 hours. The reaction mixtures were diluted with pentane 50 mL and washed with saturated NaHCO$_3$ (50 mL), dried over anhydrous Na$_2$SO$_4$ and concentrated to afford 4.2 g of crude trimethyl(4-(phenylthio)but-1-en-2-yloxy)silane (2c-5) as light yellow oils, which was used for next step without further purification.

<Preparation of a Compound of Formula 1-5>

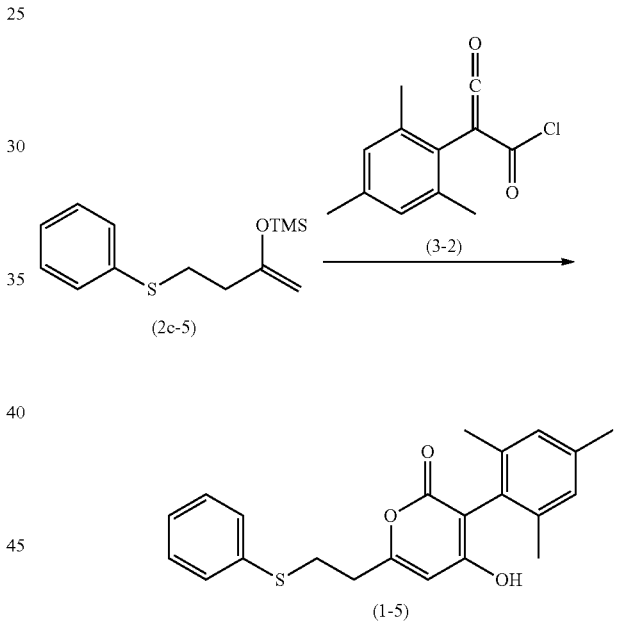

To a solution of 2-mesityl-3-oxoacryloyl chloride (3-2) (4.50 g, 20.27 mmol) in 20 mL of Xylene was added trimethyl(4-(phenylthio)but-1-en-2-yloxy)silane (2c-5) in xylene (4.40 g, crude) slowly at room temperature and the resulting mixtures were stirred at reflux for 8 hours. After completion, the reaction mixtures were concentrated to obtain 5 g of crude, which was purified by column chromatography to afford 4-hydroxy-3-mesityl-6-(2-(phenylthio)ethyl)-2H-pyran-2-one (1-5) (900 mg, 13.8%) as off white solid.

$^1$H NMR (CDCl$_3$)

δ ppm: 7.39 (2H, d), 7.32 (2H, t), 7.25-7.20 (1H, m), 6.98 (2H, s), 6.01 (H, s), 5.69 (1H, brs), 3.27 (2H, t), 2.82 (2H, t) 2.29 (3H, s), 2.11 (6H, s)

Preparation Example 1-5: Preparation of a Compound of Formula (1-9)

<Preparation of a Compound of Formula 2a-9>

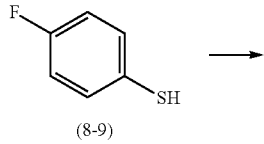
(8-9)

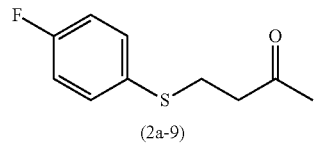
(2a-9)

To a solution of 4-fluoro thiophenol (500 mg, 3.9 mmol) in dry THF (20 vols) was added TEA (1.12 mL, 7.8 mmol) followed by methyl vinyl ketone (328 mg, 4.68 mmol) at 0° C., and the resulting mixtures were stirred for 2 hours. After completion, the reaction mixtures were poured into water (10 mL) and extracted with EtOAc (2×10 mL). The combined extracts were washed with water (5 mL), brine (5 mL), dried over anhydrous Na$_2$SO$_4$, filtered and evaporated to get the crude product. The crude product was purified by column chromatography using (SiO$_2$) by eluting with EtOAc:petether (4:96) to afford 4-(4-fluorophenylthio)butan-2-one (2a-9) (520 mg, 67.5%) as off white solid.

$^1$H NMR (CDCl$_3$)

δ ppm: 7.35 (2H, m), 7.0 (2H, m), 3.1 (2H, t), 2.72 (2H, t), 2.15 (3H, s)

<Preparation of a Compound of Formula 2c-9>

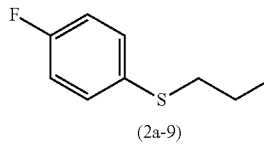
(2a-9)

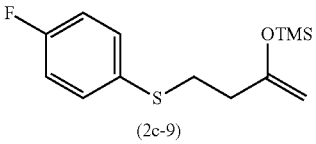
(2c-9)

To a solution of LDA (10.05 mL, 18.00 mmol) in dry THF (30 mL) at −78° C. was added a solution of 4-(4-fluorophenylthio)butan-2-one (2a-9) (3 g, 15.07 mmol) in dry THF (10 mL) drop wise and the resulting mixtures were stirred for 10 minutes, and thereto was then added quickly TMS-Cl (2.8 mL, 22.50 mmol) at −78° C. The reaction mixtures were slowly brought to room temperature and stirred for 2.5 hours. The reaction mixtures were diluted with pentane 50 mL and washed with saturated NaHCO$_3$ solution (30 mL), dried over sodium sulfate and concentrated to afford (4-(4-fluorophenylthio)but-1-en-2-yloxy)trimethylsilane (2c-9) (3.7 g) as light yellow oils, which was used for next step without further purification.

<Preparation of a Compound of Formula 1-9>

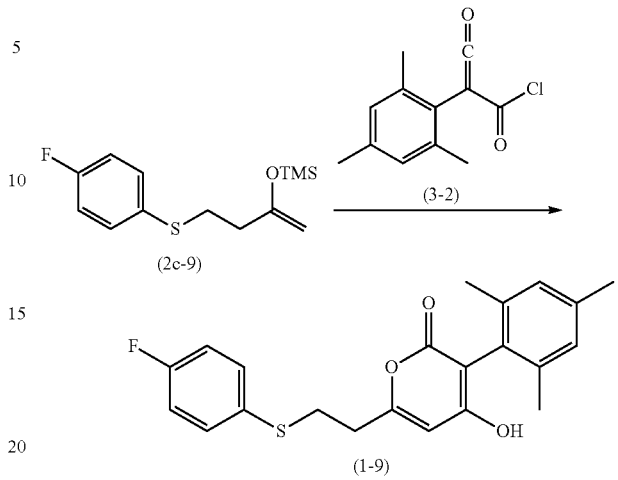

To a solution of (3-2) (6.5 g, crude) in xylene (50 mL) was added (4-(4-fluorophenylthio)but-1-en-2-yloxy)trimethylsilane (2c-9) in xylene (6 g, crude) slowly at room temperature, and the resulting mixtures were stirred at reflux for 8 hours. After completion, the reaction mixtures were filtered through Celite pad and the filtrates were concentrated to get the crude product. The crude product was purified by column chromatography using (SiO$_2$) by eluting EtOAc:petether (20:80) to afford 6-(2-(4-fluorophenylthio)ethyl)-4-hydroxy-3-mesityl-2H-pyran-2-one (1-9) (400 mg, 4.7%) as off white solid.

$^1$H NMR (CDCl$_3$)

δ ppm: 7.42 (2H, m), 7.05-6.94 (4H, m), 6.00 (1H, s), 5.57 (1H, brs), 3.21 (2H, t), 2.8 (2H, t), 2.3 (3H, s), 2.1 (6H, s)

Preparation Example 1-6: Preparation of a Compound of Formula (1-29)

<Preparation of a Compound of Formula 14g-1>

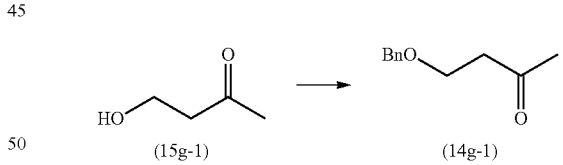

A mixture of 4-hydroxy butanone (200 g, 2.27 mol), benzyl bromide (299 mL, 2.49 mol) and DIPEA (800 mL, 4.52 mol) was heated to 150° C. for 2 hours. After completion, the reaction mixture were dissolved in 500 mL of sodium bi sulphate solution, and then extracted with EtOAc (2×1 L). The combined extracts were washed with water (1 L), brine (1 L), dried over anhydrous Na$_2$SO$_4$, filtered and evaporated. The crude residues were purified by column chromatography using (SiO$_2$) by eluting EtOAc:petether (6:94) to afford 4-(benzyloxy) butan-2-one (14g-1)(90 g, 22.2%) as brown color liquid.

$^1$H NMR (CDCl$_3$)

δ ppm: 7.35-7.25 (5H, m), 4.51 (2H, s), 3.72 (2H, t), 2.72 (2H, t); 2.18 (3H, s).

<Preparation of a Compound of Formula 13g-1>

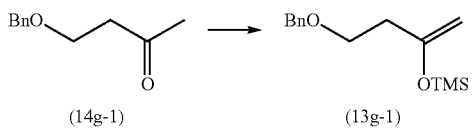

To a solution of LDA (117 mL, 210.4 mmol) in dry THF (250 mL) at −78° C. was added a solution of 4-(benzyloxy)butan-2-one (14g-1) (25 g, 140.4 mmol) in dry THF (100 mL) drop wise and the resulting mixtures were stirred for 20 minutes, and thereto was then added quickly trimethyl silyl chloride (26.2 mL, 210.4 mmol) at −78° C. The reaction mixtures were slowly brought to room temperature and stirred for 2.5 hours. The reaction mixtures were diluted with pentane 250 mL and washed with saturated sodium bicarbonate solution (250 mL), dried over sodium sulfate and concentrated to afford 33 g of crude (4-(benzyloxy)but-1-en-2-yloxy)trimethylsilane (13g-1) as light yellow oils, which was used for next step without further purification.

<Preparation of a Compound of Formula 12g-1>

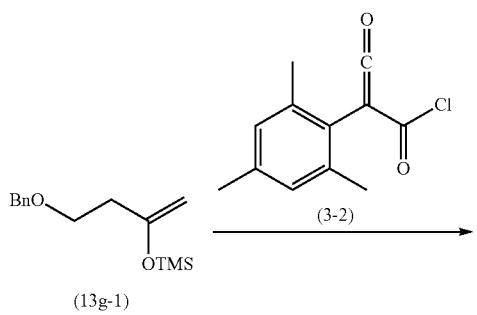

To a solution of (3-2) (27 g, crude) in xylene (250 mL) was added (4-(benzyloxy)but-1-en-2-yloxy)trimethylsilane (13g-1) (33 g, crude) in xylene (250 mL) slowly at room temperature and the resulting mixtures were stirred at reflux for 8 hours. After completion of the reaction, the reaction mixtures were concentrated. The crude product was purified by column chromatography using (SiO₂) by eluting EtOAc:petether (25:75) to afford 6-(2-(benzyloxy)ethyl)-4-hydroxy-3-mesityl-2H-pyran-2-one (12g-1) 7 g (13% overall 2 steps) as brown thick mass.

¹H NMR (CDCl₃)

δ ppm: 7.38-7.27 (5H, m), 7.0 (2H, s), 6.1 (1H, s), 4.55 (2H, s), 3.8 (2H, t), 2.85 (2H, t), 2.3 (3H, s), 2.15 (6H, s)

<Preparation of a Compound of Formula 11g-1>

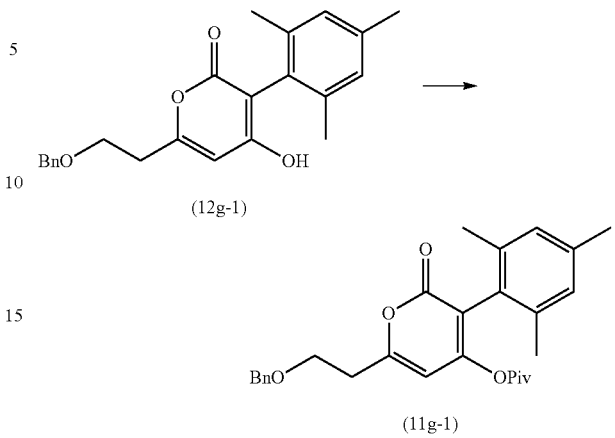

To a solution of pivaloyl chloride (4.6 mL, 38 mmol) in pyridine (20 mL) was added 6-(2-(benzyloxy)ethyl)-4-hydroxy-3-mesityl-2H-pyran-2-one (12g-1) (7 g, 19.2 mmol) slowly at RT, and the reaction was continued for 24 hours at same temperature. After completion, the reaction mixtures were poured into cold water (50 mL) and extracted with EtOAc (2×50 mL). The combined extracts were washed with water (70 mL), brine (70 mL), dried over anhydrous Na₂SO₄, filtered and evaporated. The crude product was purified by column chromatography using (SiO₂) by eluting EtOAc:petether (12:88) to afford 6-(2-hydroxyethyl)-3-mesityl-2-oxo-2H-pyran-4-yl pivalate (11g-1) (6 g, 69%) as light yellow oils.

¹H NMR (CDCl₃)

δ ppm: 7.36-7.28 (5H, m), 6.86 (2H, s), 6.14 (1H, s), 4.58 (2H, s) 3.82 (2H, t), 2.87 (2H, t); 2.25 (3H, s), 2.09 (6H, s), 0.94 (9H, s).

<Preparation of a Compound of Formula 10g-1>

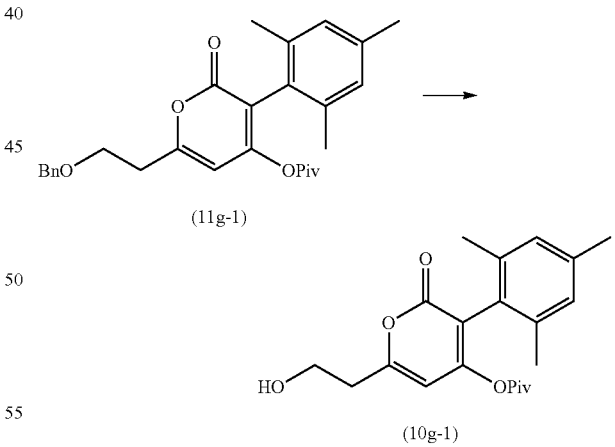

To a solution of 6-(2-hydroxyethyl)-3-mesityl-2-oxo-2H-pyran-4-yl pivalate (11g-1) (25 g, 55.8 mmol) in EtOH (250 mL) was added Darco KBB (20 g), and the resulting mixtures were stirred for 10 minutes and filtered through a pad of Celite, and thereto was then added 10% of Pd on carbon (5 g) and the resulting mixtures were hydrogenated at 20 psi. After completion, the reaction mixtures were filtered through a pad of Celite and the filtrates were concentrated to get the crude product. The crude product was purified by column chromatography using (SiO₂) by eluting with EtOAc:petether (15:85) to afford 6-(2-hydroxyethyl)-3-mesityl-2-oxo-2H-pyran-4-yl pivalate (10g-1) (10 g, 50%) as off white solid.

<Preparation of a Compound of Formula 9g-1>

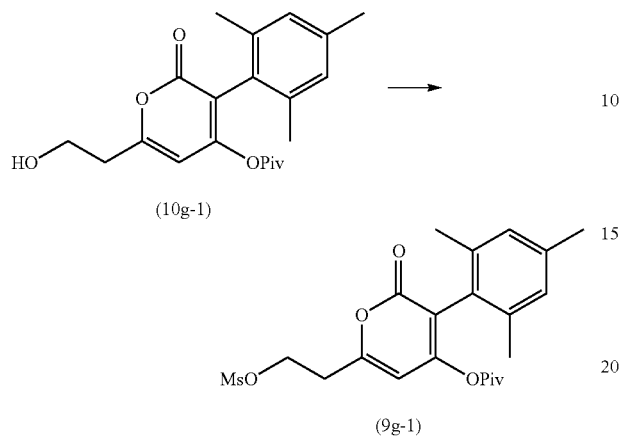

To a solution of 6-(2-hydroxyethyl)-3-mesityl-2-oxo-2H-pyran-4-yl pivalate (10g-1) (3 g, 8.37 mmol) in THF (30 mL) at 0° C. was added triethylamine (2.34 mL, 16.74 mmol) followed by mesyl chloride (0.68 mL, 10.02 mmol) and the resulting mixtures were stirred at 0° C. for 2 hours. After completion, the solvent was poured into ice water (30 mL) and extracted with EtOAc (2×50 mL). The combined extracts were washed with water (50 mL), brine (50 mL), dried over anhydrous $Na_2SO_4$, filtered and evaporated to afford 3-mesityl-6-(2-(methylsulfonyloxy)ethyl)-2-oxo-2H-pyran-4-yl pivalate (3-mesityl-6-(2-(methylsulfonyloxy) ethyl)-2-oxo-2H-pyran-4-yl pivalate (9g-1) (3.4 g, 94%) as off white solid. The product was used in next step without further purification.

$^1$H NMR ($CDCl_3$)

δ ppm: 6.87 (2H, s), 6.19 (1H, s), 4.57 (2H, t), 3.07-2.98 (5H, m), 2.26 (3H, s), 2.09 (6H, s), 0.94 (9H, s)

<Preparation of a Compound of Formula 1-29>

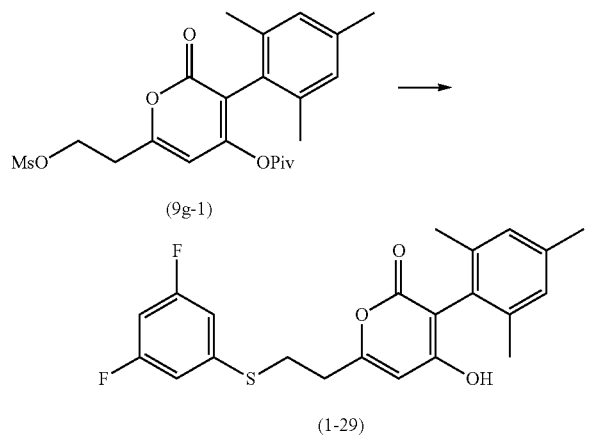

To a solution of 2-mesityl-3-oxoacryloyl chloride (3-mesityl-6-(2-(methylsulfonyloxy)ethyl)-2-oxo-2H-pyran-4-yl pivalate (9g-1) (170 mg, 0.389 mmol) and 3,5-difluoro thiophenol (62.68 mg, 0.428 mmol) in tetrahydrofuran (2 mL) was added $K_2CO_3$ (107 mg, 0.778 mmol) and the resulting mixtures were stirred at 50° C. for 2 hours. After completion, the reaction mixtures were poured into ice water (5 mL) and extracted with EtOAc (2×10 mL). The combined extracts were washed with water (2 mL), brine (2 mL), dried over anhydrous $Na_2SO_4$, filtered and evaporated. The crude was purified by column chromatography using ($SiO_2$) by eluting EtOAc:petether (18:82) to afford 6-(2-(3,5-difluorophenylthio)ethyl)-4-hydroxy-3-mesityl-2H-pyran-2-one (1-29) (80 mg, 10.8%) as off white solid.

$^1$H NMR ($CDCl_3$)

δ ppm: 7.0 (2H, m), 6.95 (2H, m), 6.65 (1H, m), 6.05 (1H, s), 5.55 (1H, brs) 3.3 (2H, t), 2.85 (2H, t), 2.3 (3H, s), 2.15 (6H, s)

Preparation Example 1-7: Preparation of a Compound of Formula (1-28)

<Preparation of a Compound of Formula 1-28>

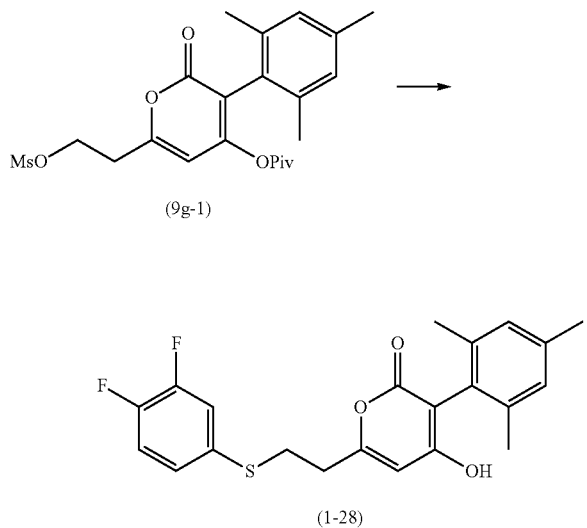

To a solution of 3-mesityl-6-(2-(methylsulfonyloxy) ethyl)-2-oxo-2H-pyran-4-yl pivalate (9g-1) (600 mg, 1.37 mmol) and 3,4-difluoro thiophenol (221.2 mg, 1.51 mmol) in tetrahydrofuran (6 mL) was added $K_2CO_3$ (379.7 mg, 2.75 mmol) and the resulting mixtures were stirred at 50° C. for 2 hours. After completion, the reaction mixtures were poured into ice water (10 mL) and extracted with EtOAc (2×10 mL). The combined extracts were washed with water (10 mL), brine (10 mL), dried over anhydrous $Na_2SO_4$, filtered and evaporated. The crude product was purified by column chromatography using ($SiO_2$) by eluting with EtOAc:petether (22:78) to afford 6-(2-(3,4-difluorophenylthio)ethyl)-4-hydroxy-3-mesityl-2H-pyran-2-one (1-28) (230 mg, 14%) as off-white solid.

$^1$H NMR ($CDCl_3$)

δ ppm: 7.22 (1H, m), 7.14 (2H, m), 6.98 (2H, s), 6.01 (1H, s), 5.59 (1H, s), 3.24 (2H, t), 2.82 (2H, t), 2.3 (3H, s), 2.11 (6H, s)

Preparation Example 1-8: Preparation of a Compound of Formula (1-27)

<Preparation of a Compound of Formula 1-27>

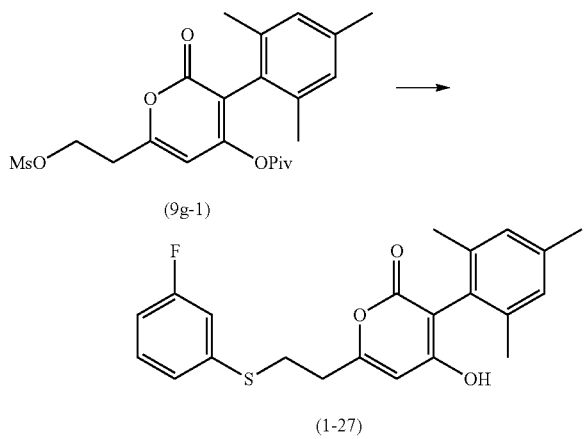

To a solution of 3-mesityl-6-(2-(methylsulfonyloxy) ethyl)-2-oxo-2H-pyran-4-yl pivalate (9g-1) (600 mg, 1.37 mmol) and 3-fluoro thiophenol (193 mg, 1.51 mmol) in tetrahydrofuran (6 mL) was added $K_2CO_3$ (379.7 mg, 2.75 mmol) and the resulting mixtures were stirred at 50° C. for 2 hours. After completion, the reaction mixtures were poured into ice water (10 mL) and extracted with EtOAc (2×10 mL). The combined extracts were washed with water (6 mL), brine (6 mL), dried over anhydrous $Na_2SO_4$, filtered and evaporated. The crude product was purified by column chromatography using ($SiO_2$) by eluting EtOAc:petether (20:80) to afford 6-(2-(3-fluorophenylthio)ethyl)-4-hydroxy-3-mesityl-2H-pyran-2-one (1-27) (270 mg, 11.2%) as off white solid.

$^1$H NMR (CDCl$_3$)

δ ppm: 7.28 (1H, m), 7.14 (1H, d), 7.08 (1H, d), 6.98 (2H, s), 6.91 (1H, t), 6.02 (1H, s), 5.6 (1H, s), 3.29 (2H, t) 2.85 (2H, t), 2.3 (3H, s), 2.11 (6H, s)

Preparation Example 1-9: Preparation of a Compound of Formula (1-4)

<Preparation of a Compound of Formula 1-4>

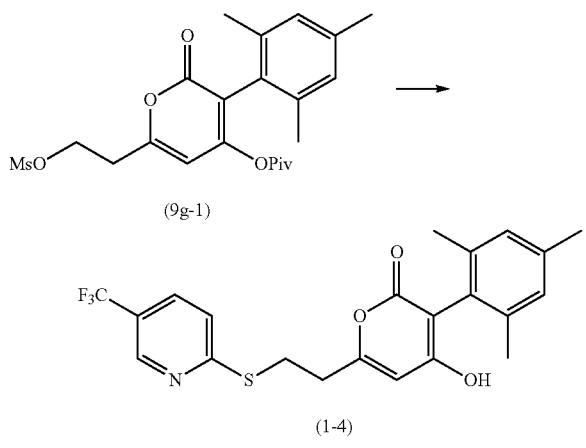

To a solution of 3-mesityl-6-(2-(methylsulfonyloxy) ethyl)-2-oxo-2H-pyran-4-yl pivalate (9g-1) (650 mg, 1.49 mmol) and 5-(trifluoromethyl)pyridine-2-thiol (293 mg, 1.63 mmol) in tetrahydrofuran (7 mL) was added $K_2CO_3$ (411 mg, 2.98 mmol) and the resulting mixtures were stirred at 50° C. for 2 hours. After completion, the reaction mixtures were poured into 1 N HCl and extracted with EtOAc (2×10 mL). The combined extracts were washed with water (7 mL), brine (7 mL), dried over anhydrous $Na_2SO_4$, filtered and evaporated. The crude product was purified by column chromatography using ($SiO_2$) by eluting EtOAc:petether (25:75) to afford to afford 4-hydroxy-3-mesityl-6-(2-(5-(trifluoromethyl)pyridin-2-ylthio)ethyl)-2H-pyran-2-one (1-4) (340 mg, 52%) as off white solid.

$^1$H NMR (CDCl$_3$)

δ ppm: 8.69 (1H, s), 7.68 (1H, d), 7.27 (1H, d), 6.98 (2H, s) 6.08 (1H, s), 5.57 (1H, s), 3.58 (2H, t), 2.99 (2H, t), 2.30 (3H, s), 2.12 (6H, s)

Preparation Example 1-10: Preparation of a Compound of Formula (1-31)

<Preparation of a Compound of Formula 1-31>

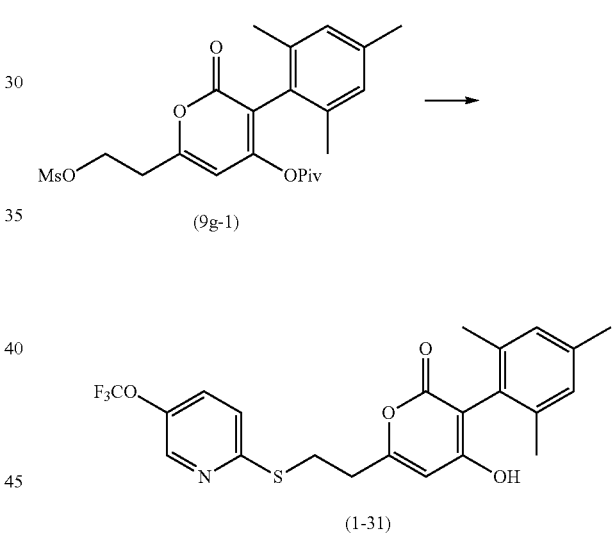

To a solution of 3-mesityl-6-(2-(methylsulfonyloxy) ethyl)-2-oxo-2H-pyran-4-yl pivalate (9g-1) (800 mg, 1.83 mmol) and 4-trifluoromethoxy thiophenol (0.30 mL, 2.01 mmol) in tetrahydrofuran (8 mL) was added $K_2CO_3$ (506 mg, 3.60 mmol) and the resulting mixtures were stirred at 50° C. for 2 hours. After completion, the reaction mixtures were poured into ice water (10 mL) and extracted with EtOAc (2×10 mL). The combined extracts were washed with water (10 mL), brine (10 mL), dried over anhydrous $Na_2SO_4$, filtered and evaporated. The crude product was purified by column chromatography using ($SiO_2$) by eluting EtOAc:petether (15:85) to afford 4-hydroxy-3-mesityl-6-(2-(4-(trifluoromethoxy)phenylthio)ethyl)-2H-pyran-2-one (1-31) (340 mg, 41%) as off white solid.

$^1$H NMR (CDCl$_3$)

δ ppm: 7.41 (2H, d), 7.17 (2H, d), 6.98 (2H, s), 6.02 (1H, s), 5.54 (1H, s), 3.27 (2H, t), 2.83 (2H, t), 2.3 (3H, s), 2.11 (6H, s)

Preparation Example 1-11: Preparation of a Compound of Formula (1-58)

<Preparation of a Compound of Formula 1-58>

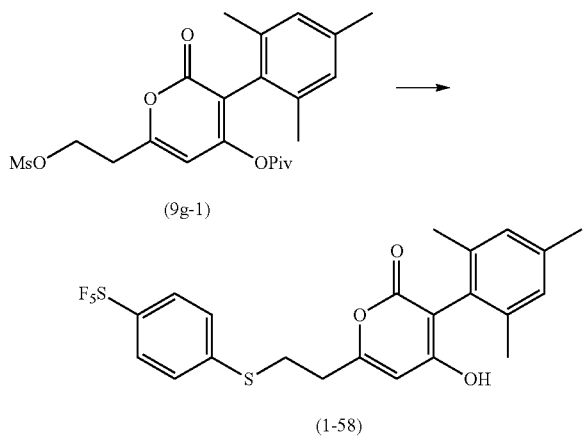

(9g-1)

(1-58)

To a solution of 3-mesityl-6-(2-(methylsulfonyloxy) ethyl)-2-oxo-2H-pyran-4-yl pivalate (9g-1) (1.7 g, 3.89 mmol) and 4-mercapto phenylsulphur pentafluoride (1.19 g, 5.06 mmol) in tetrahydrofuran (17 mL) was added $K_2CO_3$ (1.1 g, 7.75 mmol) and the resulting mixtures were stirred at 50° C. for 2 hours. After completion, the reaction mixtures were poured into 1 N HCl (10 mL) and extracted with EtOAc (2×10 mL). The combined extracts were washed with water (10 mL), brine (10 mL), dried over anhydrous $Na_2SO_4$, filtered and evaporated. The crude product was purified by column chromatography using ($SiO_2$) by eluting EtOAc:petether (12:88) to afford 6-(2-(4-mercapto pentafluoro phenylthio)ethyl)-4-hydroxy-3-mesityl-2H-pyran-2-one (1-58) (330 mg, 17.2%) as off white solid.

$^1H$ NMR ($CDCl_3$)

δ ppm: 7.67 (2H, d), 7.37 (2H, d), 6.98 (2H, s), 6.03 (1H, s), 5.65 (1H, s), 3.35 (2H, t), 2.88 (2H, t), 2.3 (3H, s), 2.11 (6H, s)

Preparation Example 1-12: Preparation of a Compound of Formula (1-8)

<Preparation of a Compound of Formula 1-8>

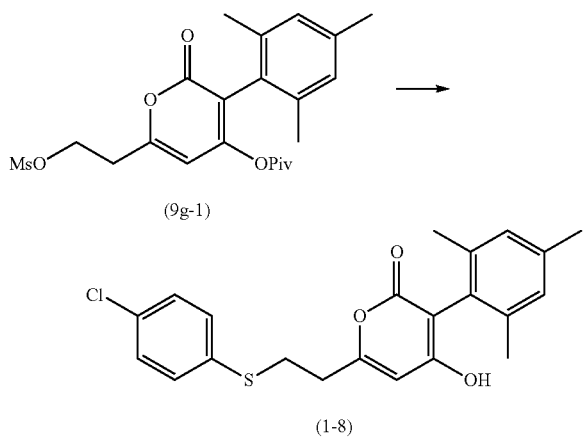

(9g-1)

(1-8)

To a solution of 3-mesityl-6-(2-(methylsulfonyloxy) ethyl)-2-oxo-2H-pyran-4-yl pivalate (9g-1) (650 mg, 1.49 mmol) and 4-chloro thiophenol (237 mg, 1.63 mmol) in tetrahydrofuran (7 mL) was added $K_2CO_3$ (411 mg, 2.98 mmol) and the resulting mixtures were stirred at 50° C. for 2 hours. After completion, the reaction mixtures were poured into 1 N HCl (10 mL) and extracted with EtOAc (2×10 mL). The combined extracts were washed with water (10 mL), brine (10 mL), dried over anhydrous $Na_2SO_4$, filtered and evaporated. The crude product was purified by prep HPLC to afford 6-(2-(4-chlorophenylthio)ethyl)-4-hydroxy-3-mesityl-2H-pyran-2-one (1-8) (340 mg, 56%) as off white solid.

$^1H$ NMR ($CDCl_3$)

δ ppm: 7.29 (4H, q), 6.98 (2H, s), 6.0 (1H, s), 5.6 (1H, s), 3.25 (2H, t), 2.82 (2H, t), 2.3 (3H, s), 2.11 (6H, s)

Preparation Example 1-13: Preparation of a Compound of Formula (1-60)

<Preparation of a Compound of Formula 1-60>

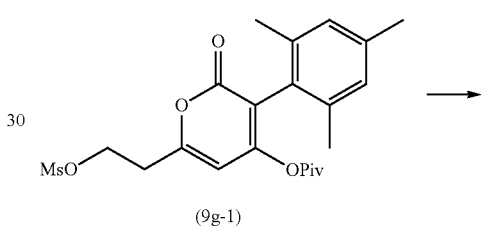

(9g-1)

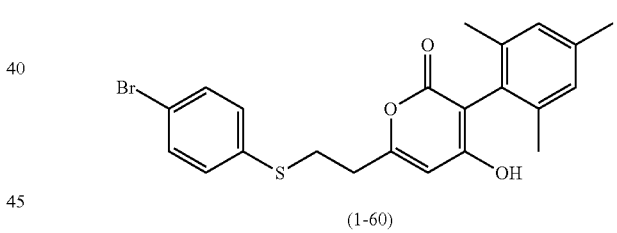

(1-60)

To a solution of 3-mesityl-6-(2-(methylsulfonyloxy) ethyl)-2-oxo-2H-pyran-4-yl pivalate (9g-1) (500 mg, 1.14 mmol) and 4-bromo thiophenol (238 mg, 1.26 mmol) in tetrahydrofuran (5 mL) was added $K_2CO_3$ (316 mg, 2.29 mmol) and the resulting mixtures were stirred at 50° C. for 2 hours. After completion, the reaction mixtures were poured into 1 N HCl (10 mL) and extracted with EtOAc (2×10 mL). The combined extracts were washed with water (10 mL), brine (10 mL), dried over anhydrous $Na_2SO_4$, filtered and evaporated. The crude product was purified by column chromatography using ($SiO_2$) by eluting EtOAc:petether (21:79) to afford 6-(2-(4-bromophenylthio)ethyl)-4-hydroxy-3-mesityl-2H-pyran-2-one (1-60)(310 mg, 30%) as off white solid.

$^1H$ NMR ($CDCl_3$)

δ ppm: 7.43 (2H, d), 7.26 (2H, d), 6.98 (2H, s), 6.0 (1H, s), 5.55 (1H, s), 3.26 (2H, t), 2.83 (2H, t), 2.3 (3H, s), 2.11 (6H, s)

Preparation Example 1-14: Preparation of a Compound of Formula (1-59)

<Preparation of a Compound of Formula 1-59>

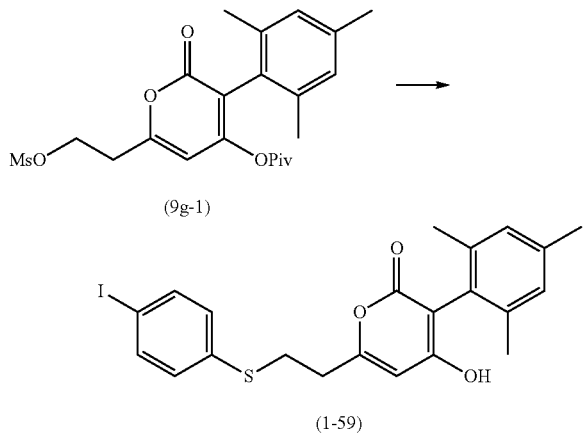

To a solution of 3-mesityl-6-(2-(methylsulfonyloxy) ethyl)-2-oxo-2H-pyran-4-yl pivalate (9g-1) (1.3 g, 2.98 mmol) and 4-iodothiophenol (774 mg, 3.27 mmol) in tetrahydrofuran (13 mL) was added K$_2$CO$_3$ (822 mg, 5.9 mmol) and the resulting mixtures were stirred at 50° C. for 2 hours. After completion, the reaction mixtures were poured Into 1 N HCl (10 mL) and extracted with EtOAc (2×10 mL). The combined extracts were washed with water (10 mL), brine (10 mL), dried over anhydrous Na$_2$SO$_4$, filtered and evaporated. The crude product was purified by column chromatography using (SiO$_2$) by eluting EtOAc:petether (16:84) to afford 4-hydroxy-6-(2-(4-iodophenylthio)ethyl)-3-mesityl-2H-pyran-2-one (1-59) (250 mg, 18%) as off-white solid.

$^1$H NMR (CDCl$_3$)

δ ppm: 7.62 (2H, d), 7.12 (2H, d), 6.98 (2H, s), 6.0 (1H, s), 5.5 (1H, s), 3.26 (2H, t), 2.82 (2H, t), 2.3 (3H, s), 2.11 (6H, s)

Preparation Example 1-15: Preparation of a Compound of Formula (1-102)

<Preparation of a Compound of Formula 1-84>

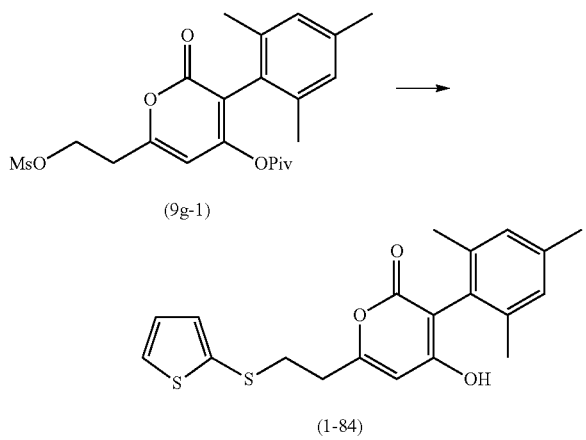

To a solution of 3-mesityl-6-(2-(methylsulfonyloxy) ethyl)-2-oxo-2H-pyran-4-yl pivalate (9g-1) (900 mg, 2.06 mmol) and thiophene-2-thiol (263 mg, 2.27 mmol) in tetrahydrofuran (9 mL) was added K$_2$CO$_3$ (569 mg, 4.12 mmol) and the resulting mixtures were stirred at 50° C. for 2 hours. After completion, the reaction mixtures were poured Into 1 N HCl (10 mL) and extracted with EtOAc (2×10 mL). The combined extracts were washed with water (10 mL), brine (10 mL), dried over anhydrous Na$_2$SO$_4$, filtered and evaporated. The crude product was purified by column chromatography using (SiO$_2$) by eluting with EtOAc:petether (20:80) to afford 4-hydroxy-3-mesityl-6-(2-(p-tolylthio)ethyl)-2H-pyran-2-one (1-84) (300 mg, 39%) as off-white solid.

$^1$H NMR (CDCl$_3$)

δ ppm: 7.38 (1H, d), 7.18 (1H, d), 7.0 (3H, m), 6.03 (1H, s), 5.6 (1H, s), 3.12 (2H, t), 2.82 (2H, t), 2.29 (3H, s), 2.12 (6H, s)

Preparation Example 1-16: Preparation of a Compound of Formula (1-85)

<Preparation of a Compound of Formula 1-85>

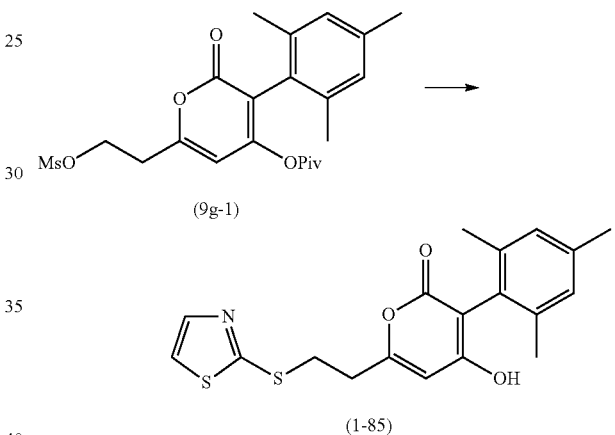

To a solution of 3-mesityl-6-(2-(methyl sulfonyloxy) ethyl)-2-oxo-2H-pyran-4-yl pivalate (9g-1) (650 mg, 1.49 mmol) and thiazole-2-thiol (191 mg, 1.63 mmol) in tetrahydrofuran (7 mL) was added K$_2$CO$_3$ (411 mg, 2.98 mmol) and the resulting mixtures were stirred at 50° C. for 2 hours. After completion, the reaction mixtures were poured into 1 N HCl (10 mL) and extracted with EtOAc (2×10 mL). The combined extracts were washed with water (10 mL), brine (10 mL), dried over anhydrous Na$_2$SO$_4$, filtered and evaporated. The crude product was purified by column chromatography using (SiO$_2$) by eluting EtOAc:petether (10:90) to afford 520 mg of semi pure compound. Further purification by prep HPLC gave 3-mesityl-2-oxo-6-(2-(thiazol-2-ylthio) ethyl)-2H-pyran-4-yl pivalate (450 mg, 18%) as off-white solid.

To a solution of 3-mesityl-2-oxo-6-(2-(thiazol-2-ylthio) ethyl)-2H-pyran-4-yl pivalate (450 mg, 0.98 mmol) in EtOH (10 mL) was added 0.5 N NaOH (5 mL) at 0° C. and the resulting mixtures were stirred at RT for 6 hours. After completion, the solvent was evaporated and the aqueous layer was acidified with 3N HCl and filtered to afford 4-hydroxy-3-mesityl-6-(2-(thiazol-2-ylthio)ethyl)-2H-pyran-2-one (1-85) (330 mg, 89%) as off-white solid.

$^1$H NMR (CDCl$_3$)

δ ppm: 7.0 (3H, m), 6.55 (1H, d), 6.05 (1H, s), 5.6 (1H, s), 4.55 (2H, t), 3.15 (2H, t), 2.3 (3H, s), 2.11 (6H, s)

Preparation Example 1-17: Preparation of a Compound of Formula (1-36)

<Preparation of a Compound of Formula 1-36>

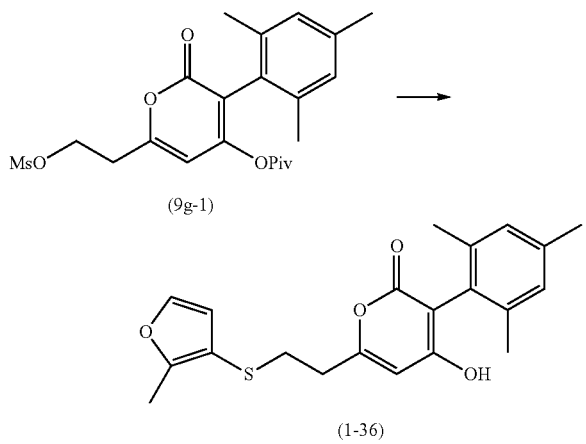

To a solution of 3-mesityl-6-(2-(methylsulfonyloxy) ethyl)-2-oxo-2H-pyran-4-yl pivalate (9g-1) (1.2 g, 2.75 mmol) and 2-methylfuran-3-thiol (345 mg, 3.63 mmol) in THF (15 mL) was added $K_2CO_3$ (759 mg, 5.50 mmol) and the resulting mixtures were stirred at 50° C. for 2 hours. After completion, the reaction mixtures were poured Into 1 N HCl (10 mL) and extracted with EtOAc (2×10 mL). The combined extracts were washed with water (10 mL), brine (10 mL), dried over anhydrous $Na_2SO_4$, filtered and evaporated. The crude product was purified by column chromatography using ($SiO_2$) by eluting with EtOAc:petether (23:77) to afford 4-hydroxy-3-mesityl-6-(2-(2-methylfuran-3-ylthio)ethyl)-2H-pyran-2-one (1-36) (270 mg, 26%) as off-white solid.

$^1$H NMR (CDCl$_3$)

δ ppm: 7.29 (1H, d), 6.99 (2H, s), 6.36 (1H, d), 6.0 (1H, s), 5.52 (1H, s), 2.97 (2H, t), 2.34 (3H, s), 2.29 (3H, s), 2.11 (6H, s)

Preparation Example 1-18: Preparation of a Compound of Formula (1-6)

<Preparation of a Compound of Formula 1-6>

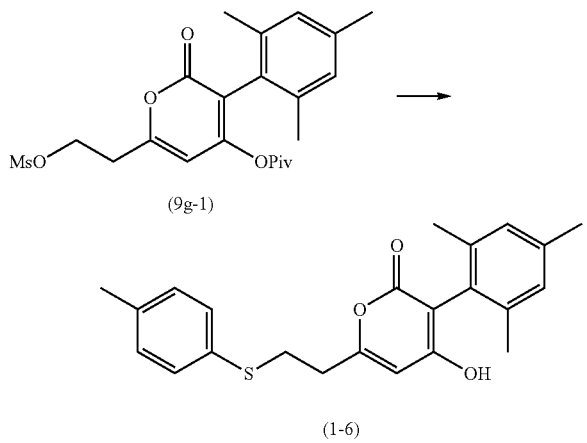

To a solution of 3-mesityl-6-(2-(methylsulfonyloxy) ethyl)-2-oxo-2H-pyran-4-yl pivalate (9g-1) (500 mg, 1.14 mmol) and 4-Methyl thiophenol (156.6 mg, 1.26 mmol) in tetrahydrofuran (5 mL) was added $K_2CO_3$ (316 mg, 2.29 mmol) and the resulting mixtures were stirred at 50° C. for 2 hours. After completion, the reaction mixtures were poured into 1 N HCl (10 mL) and extracted with EtOAc (2×10 mL). The combined extracts were washed with water (10 mL), brine (10 mL), dried over anhydrous $Na_2SO_4$, filtered and evaporated. The crude product was purified by column chromatography using ($SiO_2$) by eluting with EtOAc:petether (19:81) to afford 4-hydroxy-3-mesityl-6-(2-(p-tolylthio)ethyl)-2H-pyran-2-one (1-6) (310 mg, 71%) as off-white solid.

$^1$H NMR (CDCl$_3$)

δ ppm: 7.31 (2H, d), 7.13 (2H, d), 6.98 (2H, s), 6.00 (1H, s), 5.54 (1H, s), 3.21 (2H, t), 2.8 (2H, t), 2.33 (3H, s), 2.29 (3H, s), 2.11 (6H, s)

Preparation Example 1-19: Preparation of a Compound of Formula (1-103)

<Preparation of a Compound of Formula 1-103>

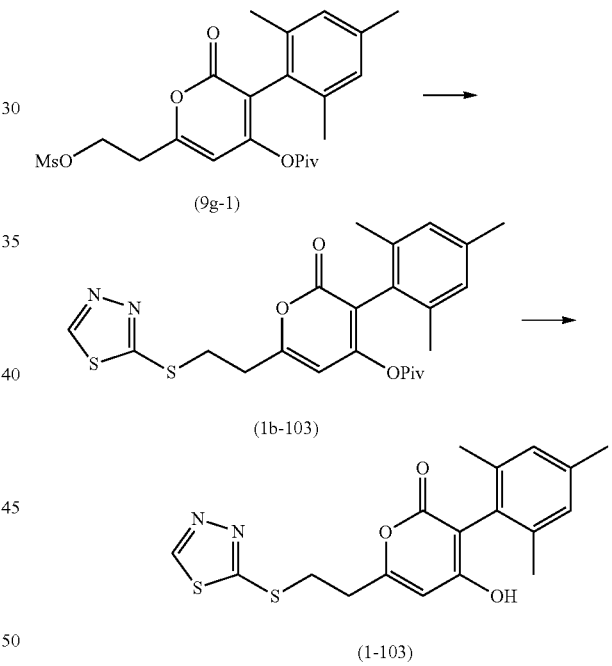

To a solution of a compound of formula (9g-1) (1.5 g, 3.44 mmol) and 1,3,4-thiadiazole-2-thiol (446 mg, 3.78 mmol) in tetrahydrofuran (15 mL) was added $K_2CO_3$ (950 mg, 6.88 mmol) and the resulting mixtures were stirred at 50° C. for 2 hours. After completion, the reaction mixtures were poured into 1 N HCl and extracted with EtOAc (2 times). The combined extracts were washed with water, brine, dried over anhydrous $Na_2SO_4$, filtered and evaporated. The crude product was purified by column chromatography to afford 510 mg (Yield—31.6%) of a compound of formula (1b-103).

To a solution of a compound of formula (1-103-a) (450 mg, 0.98 mmol) in EtOH (10 mL) was added 0.5 N NaOH (5 mL) at 0° C. and the resulting mixtures were stirred at RT for 6 hours. After completion, the solvent was evaporated and the aqueous layer was acidified with 3N HCl and filtered to afford a compound of formula (1-103).

¹H NMR (CDCl₃)

δ ppm: 9.02 (1H, s), 7.0 (2H, s), 6.09 (1H, s), 5.75 (1H, s), 3.73 (2H, t), 3.15 (2H, t), 2.3 (3H, s), 2.11 (6H, s)

Preparation Example 1-20: Preparation of a Compound of Formula (1-25)

<Preparation of a Compound of Formula 2a-25>

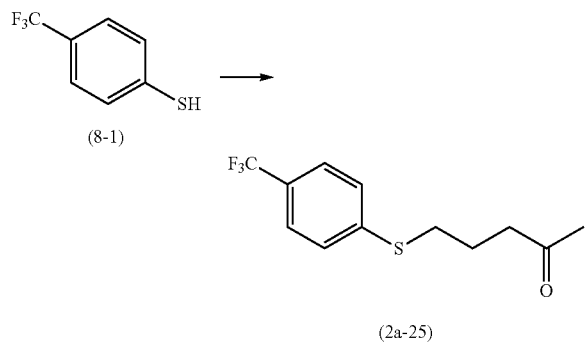

To a solution of 5-chloropentan-2-one (3.7 g, 30.8 mmol) in acetonitrile (75 mL) was added anhydrous triethylamine (7.8 mL, 56 mmol) followed by 4-(trifluoromethyl)benzenethiol (8-1) (5 g, 28 mmol) dropwise and the resulting mixtures were stirred at RT for 18 hours. After Completion, the reaction mixtures were poured into ice water (50 mL) and extracted with EtOAc (2×30 mL). The combined extracts were washed with water (30 mL), brine (30 mL), dried over anhydrous Na₂SO₄, filtered and evaporated. The crude product was purified by column chromatography (SiO₂) by eluting with EtOAc:petether (10:90) to afford 6-(2-(4-fluorophenylthio)ethyl)-4-hydroxy-3-mesityl-2H-pyran-2-one (2a-25) (5.3 g, 72.6%) as oil mass.

¹H NMR (CDCl₃)

δ ppm: 7.51 (2H, d), 7.37 (2H, d), 2.99 (2H, t), 2.61 (2H, t), 2.15 (3H, s), 1.93 (2H, m)

<Preparation of a Compound of Formula 2b-25>

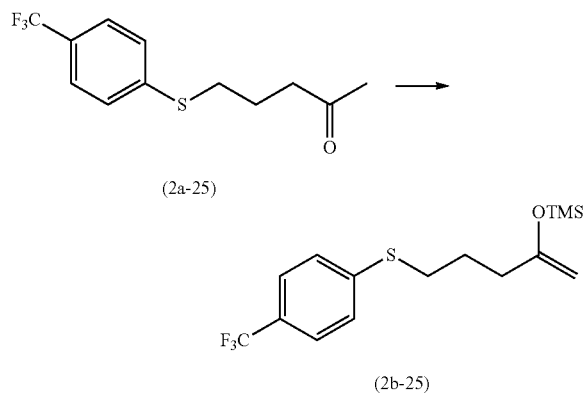

To a solution of LDA (17.15 mL, 34.3 mmol) in dry THF (90 mL) at −78° C. was added a solution of 6-(2-(4-fluorophenylthio)ethyl)-4-hydroxy-3-mesityl-2H-pyran-2-one (2a-25) (6 g, 22.9 mmol) in dry THF (60 mL) drop wise and the resulting mixtures were stirred for 30 minutes and thereto was then added quickly TMS-Cl (4.3 mL, 34.3 mmol) at −78° C. The reaction mixtures were slowly brought to room temperature and stirred for 2.5 hours. The reaction mixtures were diluted with pentane (100 mL) and washed with saturated NaHCO₃ (50 mL), dried over anhydrous Na₂SO₄ and concentrated to afford trimethyl(5-(4-(trifluoromethyl)phenylthio)pent-1-en-2-yloxy)silane (2b-25) (7g crude) as light yellow oils, which was used in next step without further purification.

<Preparation of a Compound of Formula 1-25>

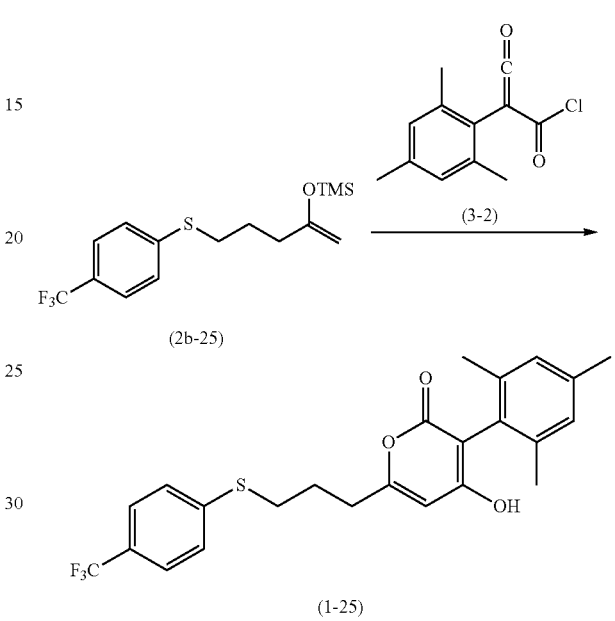

To a solution of 2-mesityl-3-oxoacryloyl chloride (3-2) (6.5 g, crude) in xylene (70 mL) was added trimethyl (5-(4-(trifluoromethyl)phenylthio)pent-1-en-2-yloxy) silane (2b-25) (7 g, crude) in xylene (30 mL) slowly at room temperature and the resulting mixtures were stirred at reflux for 8 hours. After completion, the solvent was evaporated and the residue was purified by column chromatography using (SiO₂) by eluting EtOAc:petether (24:76) to get semi pure (1-25). Further purification by prep-HPLC gave 4-hydroxy-3-mesityl-6-(3-(4-(trifluoromethyl)phenylthio) propyl)-2H-pyran-2-one (1-25) (350 mg, 3.7%) as off white solid.

¹H NMR (CDCl₃)

δ ppm: 7.53 (2H, d), 7.38 (2H, d), 6.98 (2H, s) 6.0 (1H, s), 5.52 (1H, s), 3.06 (2H, t), 2.7 (2H, t), 2.3 (3H, s), 2.11 (8H, m)

Preparation Example 1-21: Preparation of a Compound of Formula (1-19)

<Preparation of a Compound of Formula 17-19>

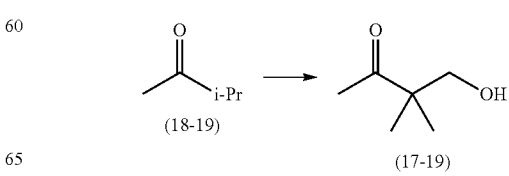

A solution of 3-methylbutan-2-one (18-19) (10 g, 0.11 mol) and paraformaldehyde (4.5 mg, 0.15 mol) in TFA (40 mL) was stirred at 80° C. for 18 hours. After completion, the solvent was evaporated, the residue was taken in MeOH (80 mL) and 2 N NaOH (40 mL) at 0° C. and the resulting mixtures were stirred for 1 hour. After completion, the solvent was evaporated, the residue was taken in ice water (100 mL) and extracted with EtOAc (2×100 mL). The combined extracts were washed with water (100 mL), brine (100 mL), dried over anhydrous Na₂SO₄, filtered and evaporated to afford 4-hydroxy-3,3-dimethylbutan-2-one (17-19) (6 g, 44.5%) as colorless oil.

<Preparation of a Compound of Formula 16-19>

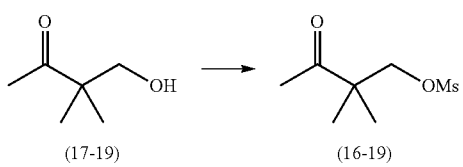

(17-19)    (16-19)

To a solution of 4-hydroxy-3,3-dimethylbutan-2-one (17-19) (6 g, 0.05 mol) in THF (60 mL) at 0° C. was added triethyl amine (14.3 mL, 0.1 mol) followed by mesyl chloride (4.76 mL, 0.062 mol) and the resulting mixtures were stirred at 0° C. for 1 hour. After completion, the solvent was poured into ice water (50 mL) and extracted with EtOAc (2×50 mL). The combined extracts were washed with water (50 mL), brine (50 mL), dried over anhydrous Na₂SO₄, filtered and evaporated to afford 2,2-dimethyl-3-oxobutyl methanesulfonate (16-19) (8 g, 79%) as pale yellow oil.

¹H NMR (CDCl₃)

δ ppm: 4.2 (2H, s), 3.02 (3H, s), 2.19 (3H, s), 1.24 (6H, s)

<Preparation of a Compound of Formula 2a-19>

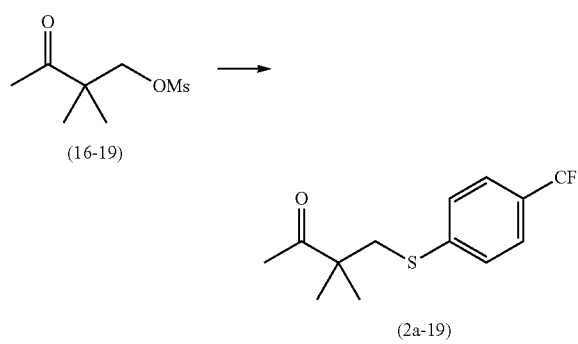

To a solution of 2,2-dimethyl-3-oxobutyl methanesulfonate (16-19) (800 mg, 4.12 mmol) and 4-trifluoromethyl thiophenol (807 mg, 4.53 mmol) in tetrahydrofuran (15 mL) was added K₂CO₃ (1.13 g, 8.24 mmol) and the resulting mixtures were stirred at 50° C. for 18 hours. After completion, the reaction mixtures were poured into ice water (10 mL) and extracted with EtOAc (2×10 mL). The combined extracts were washed with water (10 mL), brine (10 mL), dried over anhydrous Na₂SO₄, filtered and evaporated. The crude product was purified by column chromatography (SiO₂) by eluting with EtOAc:petether (10:90) to afford 3,3-dimethyl-4-(4-(trifluoromethyl)phenylthio)butan-2-one (2a-19) (600 mg, 52.2%) as color less oily mass.

¹H NMR (CDCl₃)

δ ppm: 7.5 (2H, d), 7.41 (2H, d), 3.19 (2H, s), 2.18 (3H, s), 1.28 (6H, s)

<Preparation of a Compound of Formula 2b-19>

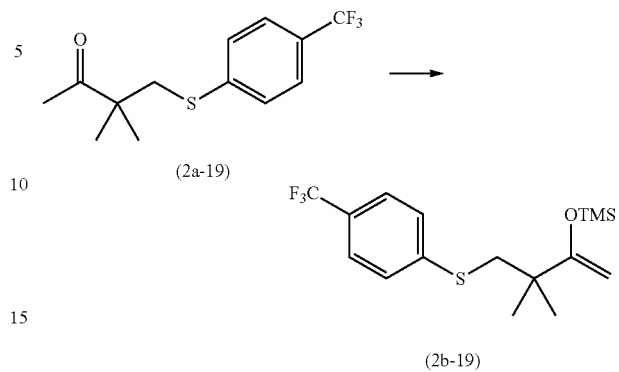

To a solution of LDA (0.6 mL, 1.08 mmol) in dry THF (2 mL) at −78° C. was added a solution of 3,3-dimethyl-4-(4-(trifluoromethyl)phenylthio)butan-2-one (2a-19) (200 mg, 0.72 mmol) in dry THF (2 mL) drop wise and the resulting mixtures were stirred for 20 minutes and thereto was then added quickly TMS-Cl (0.13 mL, 1.08 mmol) at −78° C., and the reaction mixtures were slowly brought to room temperature and stirred for 2.5 hours. The reaction mixtures were diluted with pentane (5 mL) and washed with saturated NaHCO₃, dried over anhydrous Na₂SO₄ and concentrated to afford (3,3-dimethyl-4-(4-(trifluoromethyl)phenylthio)but-1-en-2-yloxy)trimethylsilane (2b-19)(300 mg, Crude) as light yellow oil, which was used for next step without further purification.

<Preparation of a Compound of Formula 1-19>

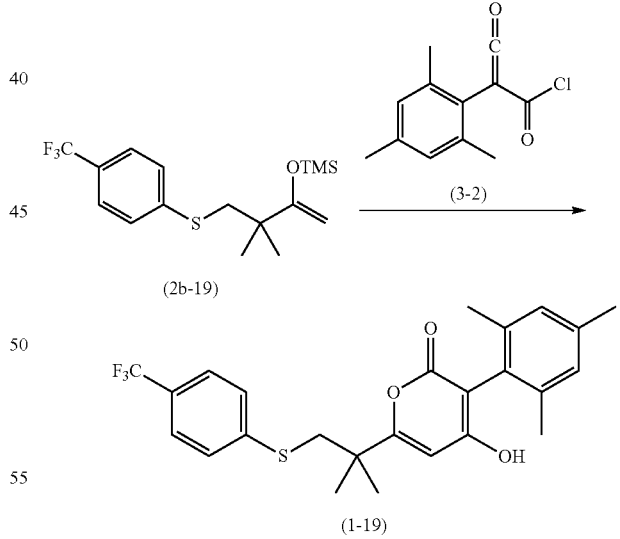

To a solution of 2-mesityl-3-oxoacryloyl chloride (3-2) (2.2 g, crude) in xylene (40 mL) was added (3,3-dimethyl-4-(4-(trifluoromethyl)phenylthio)but-1-en-2-yloxy)trimethylsilane (2b-19) (2.5 g, crude) in xylene slowly at room temperature and the resulting mixtures were stirred at reflux for 16 hours. After Completion, the solvent was evaporated and the crude product was purified by prep HPLC to afford 4-hydroxy-3- mesityl-6-(2-methyl-1-(4-(trifluoromethyl)

phenylthio)propan-2-yl)-2H-pyran-2-one (1-19) (600 mg, 18% over all 2 steps) as light brown solid.

¹H NMR (CDCl₃)

δ ppm: 7.48 (2H, d), 7.39 (2H, d), 6.97 (2H, s) 6.08 (1H, s), 5.55 (1H, s), 3.34 (2H, s), 2.29 (3H, s), 2.06 (6H, s), 1.44 (6H, s)

Preparation Example 1-22: Preparation of a Compound of Formula (1-91)

<Preparation of a Compound of Formula 2a-91>

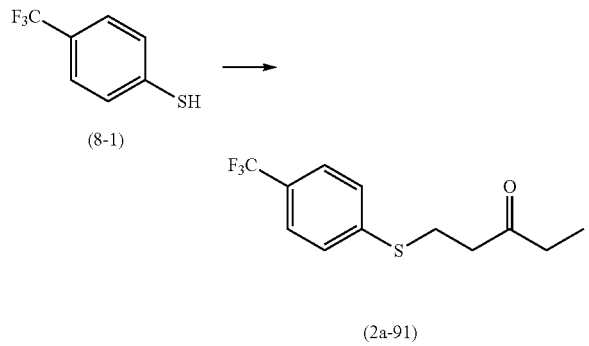

To a solution of 4-trifluoromethyl thiophenol (3 g, 16.8 mmol) in dry THF (6 mL) was added TEA (4.7 mL, 33.66 mmol) followed by ethyl vinyl ketone (1.69 g, 20.2 mmol) at 0° C. and the resulting mixtures were stirred for 2 hours at RT. After completion, the solvent was poured into water (30 mL) and extracted with EtOAc (2×20 mL). The combined extracts were washed with water (30 mL), brine (30 mL), dried over anhydrous Na₂SO₄, filtered and evaporated. The crude product was purified by column chromatography (SiO₂) using EtOAc:petether (10:90) as eluent to afford 1-(4-(trifluoromethyl)phenylthio)pentan-3-one (2a-91) (4.4 g, 65%) as brown liquid.

¹H NMR (CDCl₂)

δ ppm: 7.52 (2H, d), 7.36 (2H, d), 3.21 (2H, t), 2.77 (2H, t), 2.44 (2H, q), 1.07 (3H, t)

<Preparation of a Compound of Formula 2b-91>

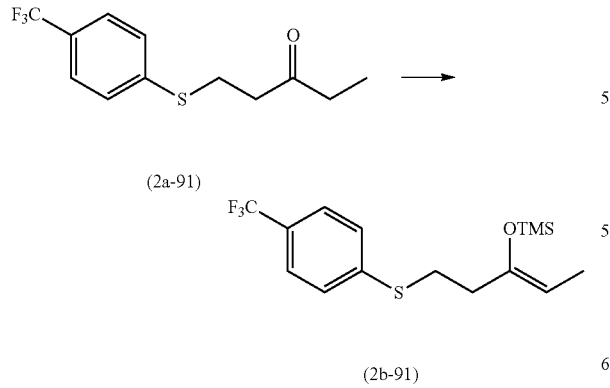

To a solution of LDA (12.6 mL, 25.19 mmol) in dry THF (50 mL) at −78° C. was added a solution of 1-(4-(trifluoromethyl)phenylthio)pentan-3-one (2a-91) (4.4 g, 16.79 mmol) in dry THF (20 mL) drop wise and the resulting mixtures were stirred for 10 minutes and thereto was then added quickly TMS-Cl (3.4 mL, 25.19 mmol) at −78° C., and the reaction mixtures were slowly brought to room temperature stirred for 2.5 hours. The reaction mixtures were diluted with pentane 10 mL and washed with saturated sodium bicarbonate, dried over anhydrous Na₂SO₄ and concentrated to afford 5 g of trimethyl(5-(4-(trifluoromethyl)phenylthio)pent-2-en-3-yloxy)silane (2b-91) as light yellow oils, which was used for next step without further purification.

<Preparation of a Compound of Formula 1-91>

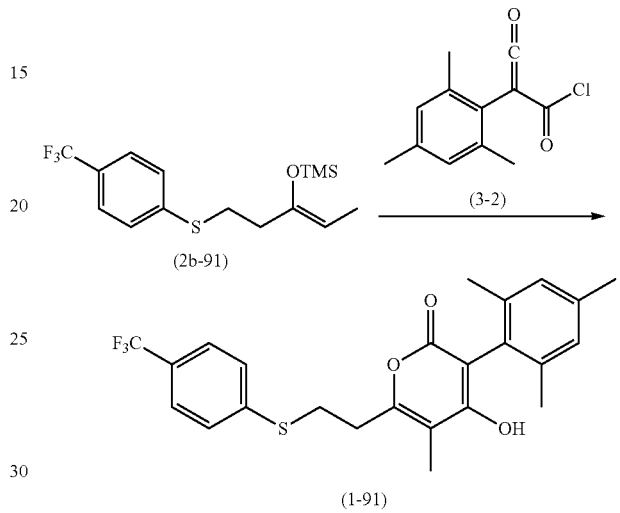

To a solution of 2-mesityl-3-oxoacryloyl chloride (3-2) (4.4 g, crude) in xylene (50 mL) was added trimethyl (5-(4-(trifluoromethyl)phenylthio)pent-2-en-3-yloxy) silane (2b-91) (5 g, crude) in xylene (50 mL) slowly at room temperature, and the resulting mixtures were stirred at reflux for 3 hours. After completion, the solvent was evaporated and the crude product was purified by column chromatography (SiO₂) by using EtOAc:petether (23:77) to afford 720 mg of semi pure (1-91). Further purification by Prep HPLC gave pure 4-hydroxy-3-mesityl-5-methyl-6-(2-(4-(trifluoromethyl)phenylthio)ethyl)-2H-pyran-2-one (1-91) (288 mg, 4.2%) as off white solid.

¹H NMR (CDCl₃)

δ ppm: 7.54 (2H, d), 7.42 (2H, d), 6.99 (2H, s), 5.61 (1H, s), 3.38 (2H, t), 2.95 (2H, t), 2.3 (3H, s), 2.10 (6H, s), 1.95 (3H, s)

Preparation Example 1-23: Preparation of a Compound of Formula (1-97)

<Preparation of a Compound of Formula 1-97>

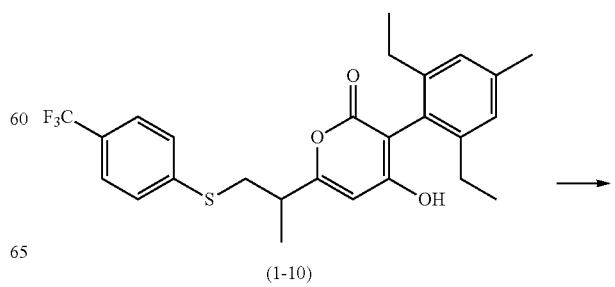

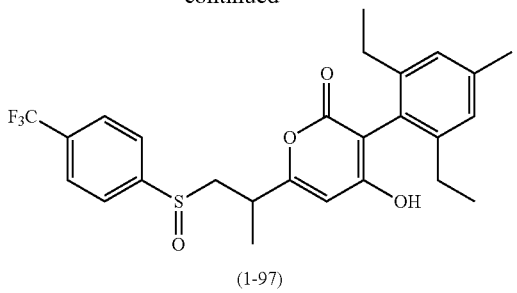

(1-97)

At RT, to a compound of formula (1-10) 160 mg was added chloroform 1 ml. The resulting mixtures were cooled to 0° C. with stirring and thereto was added a mixed solution of meta-chloroperoxybenzoic acid in chloroform 2 ml drop wise. The resulting mixtures were stirred for about 30 minutes. The resulting mixtures were then raised to RT and were stirred at RT for 3 hours. The reaction solutions were diluted with chloroform and washed with 10% aqueous sodium sulfite solution. The resulting chloroform layer was washed with saturated saline and dried over anhydrous $Na_2SO_4$ and filtered. The resulting filtrates were concentrated under reduced pressure to afford oily materials. The resulting materials were purified by column chromatography ($SiO_2$) to afford the compound of formula (1-97) 68 mg.

$^1$H NMR (CDCl$_3$)

δ ppm: 7.83-7.75 (4H, m), 7.00 (2H, s), 6.33-6.07 (1H, m), 3.39-3.18 (2H, m), 3.05-2.90 (1H, m), 2.52-2.32 (7H, m), 1.62-1.44 (3H, m), 1.15-1.06 (6H, m)

A similar reaction to process 1-4 using a compound of formula (1-11) instead of the compound of formula (1-10) afford the following present compound.

<The Compound of Formula 1-63>

$^1$H NMR (CDCl$_3$)

δ ppm: 7.83-7.75 (4H, m), 6.96 (2H, t), 6.31-6.04 (1H, m), 3.40-3.19 (2H, m), 3.05-2.89 (1H, m), 2.33-2.05 (9H, m), 1.62-1.60 (3H, m)

Next, the formulation examples are shown below. Here the present compound is expressed as the number of a structural formula.

| Formulation 1 Wettable powder | |
| --- | --- |
| Compound (1-1) | 50% by weight |
| Sodium ligninsulfonate | 5% by weight |
| Polyoxyethylene alkyl ether | 5% by weight |
| White carbon | 5% by weight |
| Clay | 35% by weight |

The ingredients shown above are mixed and ground to obtain a wettable powder.

The compound (1-1) is replaced with any of the compounds (1-2) to (1-107) to obtain respective formulations.

| Formulation 2 Granules | |
| --- | --- |
| Compound (1-1) | 1.5% by weight |
| Sodium ligninsulfonate | 2% by weight |
| Talc | 40% by weight |
| Bentonite | 56.5% by weight |

The ingredients shown above are mixed, and thereto is added water, and the resulting mixtures are fully kneaded, and were then subjected to granulation and drying to obtain a granule.

The compound (1-1) is replaced with any of the compounds (1-2) to (1-107) to obtain respective formulations.

| Formulation 3 Suspension concentrates | |
| --- | --- |
| Compound (1-1) | 10% by weight |
| Mixture of polyoxyethylene alkylether sulfate ammonium salt and white carbon (weight ratio 1:1) | 35% by weight |
| Water | 55% by weight |

The ingredients shown above are mixed, and the resulting mixtures are then subjected to fine grinding according to wet grinding method, to obtain a suspension concentrate.

The compound (1-1) is replaced with any of the compounds (1-2) to (1-107) to obtain respective formulations.

Next, test examples are shown below.

Here an efficacy for controlling weeds on the present compound was visually observed and evaluated in 11 criteria of 0 to 10 (0 represents no action, 10 represents complete death and the intermediate efficacy were evaluated in 1 to 9 criteria).

Test 1-1 Post-Emergence Treatment Test

Commercial soil for propagation was put in a pot measuring 8 cm in diameter and 6.5 cm in height, and in the pot, seeds of *Echinochloa crus-galli* were sown, and then covered with soil of about 0.5 cm thickness and the plants were grown in a greenhouse. When the plants were grown to 1-2 leaf stages, a predetermined amount of a chemical diluted solution containing a compound (1-1) was uniformly spayed on the whole plants. Here the chemical diluted solution was prepared by dissolving a predetermined amount of the compound (1-1) in dimethylformamide solution containing 2% of Tween 20 (polyoxyethylene sorbitan fatty acid ester) (manufactured by MP Biomedicals Inc.) and then diluting the solution with deionized water. After spraying, plants were grown in a greenhouse and after 20 days of the treatment, the efficacy for *Echinochloa crus-galli* was observed and the controlling effect was evaluated.

Similarly, the present compounds (1-4), (1-5), (1-8), (1-9), (1-10), (1-11), (1-12), (1-25), (1-27), (1-28), (1-29), (1-31), (1-58), (1-59), (1-60), (1-63), (1-84), (1-97) and (1-103) were also tested.

As a result, compounds (1-1), (1-4), (1-5), (1-8), (1-9), (1-10), (1-11), (1-12), (1-25), (1-27), (1-28), (1-29), (1-31), (1-58), (1-59), (1-60), (1-84), (1-97) and (1-103) were all shown an efficacy of 9 or more at a treatment amount of chemicals of 1,000g/10,000 m$^2$.

Test 1-2 Post-Emergence Treatment Test

Commercial soil for propagation was put in a pot measuring 8 cm in diameter and 6.5 cm in height, and in the pot, seeds of *Galium aparine* were sown, and then covered with soil of about 0.5 cm thickness and the plants were grown in a greenhouse. When the plants were grown to 1-2 leaf stages, a predetermined amount of a chemical diluted solution containing a compound (1-11) was uniformly spayed on the whole plants. Here the chemical diluted solution was prepared similarly to the test example 1-1. After spraying, plants were grown in a greenhouse and after 20 days of the treatment, the efficacy for *Galium aparine* was observed and evaluated.

Similarly, the present compound (1-63) was also tested.

As a result, compounds (1-11) and (1-63) were all shown an efficacy of 7 or more at a treatment amount of chemicals of 1,000g/10,000 m$^2$.

Test 2-1 Pre-Emergence Treatment Test

Steam sterilized field soil was put in a pot measuring 8 cm in diameter and 6.5 cm in height, and in the pot, seeds of *Echinochloa crus-galli* were sown, and then covered with soil of about 0.5 cm thickness. Then a predetermined amount of a chemical diluted solution containing a compound (1-1) was uniformly spayed on the soil surface. Here the chemical diluted solution was prepared similarly to the test example 1-1. After chemical treatment, plants were grown in a greenhouse, and after 3 weeks of the spraying, the efficacy for *Echinochloa crus-galli* was observed and evaluated.

Similarly, the present compounds (1-10), (1-11), (1-12), (1-63) and (1-97) were also tested.

As a result, compounds (1-1), (1-10), (1-11), (1-12), (1-63) and (1-97) were all shown an efficacy of 7 or more at a treatment amount of chemicals of 1,000g/10,000 m².

The invention claimed is:

1. A pyrone compound of formula (I):

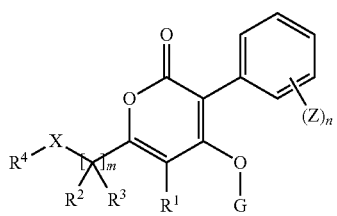

(I)

wherein:
- m is 2;
- n is an integer of any one of 1 to 3;
- X is O, S, S(O) or S(O)$_2$;
- $R^1$ is a hydrogen atom or a methyl group;
- $R^2$ and $R^3$ are each independently of each other a hydrogen atom, a methyl group, or an ethyl group, or alternatively $R^2$ and $R^3$ connect with each other to form an ethylene chain with the proviso that two $R^2$ may be the same or different to each other and two $R^3$ may be the same or different to each other;
- $R^4$ is a phenyl group, a 2-pyridyl group, a 3-furyl group, a 2-thienyl group, a 2-thiazolyl group or a 2-(1,3,4-triazolyl) group, wherein the phenyl group, the 2-pyridyl group, the 3-furyl group, the 2-thienyl group, the 2-thiazolyl group and the 2-(1,3,4-triazolyl) group each have at least one substituent selected from the group consisting of a chlorine atom, a bromine atom, an iodine atom, a fluorine atom, a methyl group, an ethyl group, an isopropyl group, a tert-butyl group, a methoxy group, a nitro group, an amino group, a cyano group, a hydroxyl group, an acetyl group, a methoxycarbonyl group, a pentafluorothio group, a pentafluoroethyl group, a difluoroethyl group, a heptafluoroisopropyl group, a trifluoromethylthio group, a trifluoromethoxy group and a trifluoromethyl group;
- G is a hydrogen atom, an acetyl group, a propionyl group, a butylcarbonyl group, a benzoyl group, a methylsulfonyl group, a methoxycarbonyl group, an ethoxycarbonyl group, an allyloxycarbonyl group, a phenoxycarbonyl group, a methoxymethyl group or an ethoxymethyl group; and
- Z is a methyl group, an ethyl group, a phenyl group, a vinyl group, a cyclopropyl group, a nitro group, a fluorine atom, a chlorine atom, a bromine atom, a methoxy group, a trifluoromethyl group, a 5-trifluoromethyl-2-chloropyridyloxy group or an ethynyl group, or an agronomically acceptable salt thereof.

2. The pyrone compound of claim 1 wherein G is a hydrogen atom, or an agronomically acceptable salt thereof.

3. A herbicide comprising the pyrone compound of claim 1, or an agronomically acceptable salt thereof, as an active ingredient and an inert carrier.

4. A method for controlling a weed, which comprises applying an effective amount of the pyrone compound of claim 1, or an agronomically acceptable salt thereof, to a weed or to a soil where the weed grows.

5. A herbicide comprising the pyrone compound of claim 2, or an agronomically acceptable salt thereof, as an active ingredient and an inert carrier.

6. A method for controlling a weed, which comprises applying an effective amount of the pyrone compound of claim 2, or an agronomically acceptable salt thereof, to a weed or a soil where the weed grows.

* * * * *

UNITED STATES PATENT AND TRADEMARK OFFICE
CERTIFICATE OF CORRECTION

PATENT NO. : 9,868,714 B2
APPLICATION NO. : 14/433722
DATED : January 16, 2018
INVENTOR(S) : Yosuke Nakashima et al.

It is certified that error appears in the above-identified patent and that said Letters Patent is hereby corrected as shown below:

On the Title Page

"(73) Assignee: SUMITOMO CHEMICAL COMPANY, Tokyo (JP)", should read
--(73) Assignee: SUMITOMO CHEMICAL COMPANY, LIMITED, Tokyo (JP)--.

Signed and Sealed this
Twenty-ninth Day of May, 2018

Andrei Iancu
*Director of the United States Patent and Trademark Office*